(12) United States Patent  
Hoelder et al.

(10) Patent No.: US 7,968,546 B2  
(45) Date of Patent: Jun. 28, 2011

(54) PYRIDAZINONE KINASE INHIBITORS

(75) Inventors: Swen Hoelder, Constance (DE); Gunter Muller, Sulzbach (DE); Karl Schoenafinger, Alzenau (DE); David William Will, Kriftel (DE); Hans Matter, Langenselbold (DE); Martin Bossart, Frankfurt (DE); Cecile Combeau, Fontenay aux Roses (FR); Christine Delaisi, Saint Maur (FR); Ingrid Sassoon, Villejuif (FR); Anke Steinmetz, Vitry sur Seine (FR); Didier Benard, Lyons (FR)

(73) Assignee: Sanofi-Aventis Deutschland GmbH, Frankfurt Am-Main (DE)

( * ) Notice: Subject to any disclaimer, the term of this patent is extended or adjusted under 35 U.S.C. 154(b) by 0 days.

(21) Appl. No.: 12/359,754

(22) Filed: Jan. 26, 2009

(65) Prior Publication Data

US 2009/0130209 A1 May 21, 2009

Related U.S. Application Data

(60) Division of application No. 11/560,620, filed on Nov. 16, 2006, now Pat. No. 7,507,734, which is a continuation of application No. PCT/EP2005/006046, filed on May 17, 2005.

(30) Foreign Application Priority Data

May 18, 2004 (EP) .................... 04011735

(51) Int. Cl.
- C07D 401/04 (2006.01)
- A61K 31/501 (2006.01)
- A61P 29/00 (2006.01)
- A61P 7/12 (2006.01)
- A61P 3/10 (2006.01)
- A61P 25/28 (2006.01)
- A61P 35/00 (2006.01)

(52) U.S. Cl. .................. 514/252.03; 544/238
(58) Field of Classification Search .............. 544/238; 514/252.06, 252.03
See application file for complete search history.

(56) References Cited

U.S. PATENT DOCUMENTS

| | | | |
|---|---|---|---|
| 4,353,905 | A | 10/1982 | Sircar et al. |
| 4,734,415 | A | 3/1988 | Sircar et al. |
| 5,607,944 | A | 3/1997 | Linz et al. |
| 2009/0035267 | A1* | 2/2009 | Moore et al. ............ 424/85.4 |

FOREIGN PATENT DOCUMENTS

| | | |
|---|---|---|
| EP | 0 075 436 | 3/1983 |
| EP | 0 639 575 | 2/1995 |
| JP | 9216883 | 8/1997 |
| JP | 09216883 | * 8/1997 |
| WO | WO 01/29025 | 4/2001 |
| WO | WO 02/22605 | 3/2002 |
| WO | WO 02/092593 | 11/2002 |
| WO | WO03/028721 | 4/2003 |
| WO | WO 03/059891 | 7/2003 |
| WO | WO 2004/046130 | 6/2004 |
| WO | WO 2005/085230 | 9/2005 |
| WO | WO 2005/085231 | 9/2005 |

OTHER PUBLICATIONS

Griesser Chapter 8, The Importance of Solvates (pp. 211-230), in the text, Polymorphism: In the Pharmaceutical Industry, Hilfiker, 2006.*
Sayed, et al., Molecules (2003), 8(3), 322-332.*
Griesser, Polymorphism: In the Pharmaceutical Industry, Chapter 8, The Importance of Solvates, 2006, pp. 126-127.
Huwe et al, Small Molecules As Inhibitors of Cyclin-Dependent Kinases, Ange. Chem. Int. Ed. 2003, 42, pp. 2122-2138.
Lee et al, Regulators of G1 Cyclin-Dependent Kinases and Cancers, Cancer and Metastasis Reviews 22: 435-449, 2003.

* cited by examiner

*Primary Examiner* — James O Wilson
*Assistant Examiner* — Cecilia M Jaisle
(74) *Attorney, Agent, or Firm* — Scully, Scott, Murphy & Presser, P.C.

(57) ABSTRACT

Disclosed are compounds of Formula I

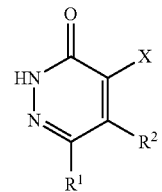

wherein X is

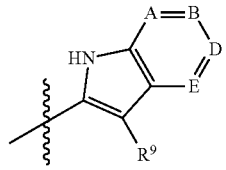

and $R^2$, $R^1$, A, B, D, E, $R^9$ are as defined herein useful for treating cancers.

10 Claims, No Drawings

PYRIDAZINONE KINASE INHIBITORS

This application is a division of U.S. application Ser. No. 11/560,620, filed Nov. 16, 2006, now allowed, which is a continuation of International Application PCT/EP2005/006046, filed May 17, 2005.

The present invention relates to compounds according to the general formula (I), with the definitions of the substituents X, $R^1$ and $R^2$ given below in the text, as well as their physiologically acceptable salts, methods for producing these compounds and their use as pharmaceuticals.

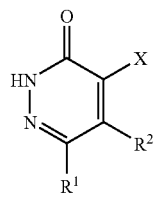
(I)

These compounds are kinase inhibitors, in particular inhibitors of the kinase CDK2 (cyclin-dependent kinase 2).

It is known from literature that in the case of neoplastic diseases such as cancer, there is a connection between the therapy of said diseases and the inhibition of CDK2. There are many compounds available, which can be employed as inhibitors of CDK2 and/or other cyclin-dependent kinases such as CDK4 or CDK6 (M. H. Lee et al., Cancer and Metastasis review 22 (2003), 435-449; A. Huwe et al., Angew. Chem. Int. Ed. 42 (2003), 2122-2138; WO 03/028721).

The international application PCT/EP 03/12949 discloses pyridazinone derivatives, which can be employed for the inhibition of CDK2. They differ from the compounds of the present invention in the substitution of the pyridazinone cycle, since at position 4 of the cycle there is an amido group defined as substituent instead of a heteroaryl substituent such as pyrrole or indole.

Furthermore, there are many pyridazinone derivatives described in literature, which differ from those of the present invention due to a different substitution pattern and (partially) different indications.

WO 03/059891 discloses pyridazinone derivatives that are useful for treating diseases and conditions caused or exacerbated by unregulated p38 MAP Kinase activity and/or TNF activity. The compounds described therein can be used, for example, for the treatment of inflammatory conditions, diabetes, Alzheimer's disease or cancer. They differ from the compounds of the present invention in the substitution of the pyridazinone cycle, since the nitrogen at position 2 of the cycle is mostly substituted with alky, aryl or heteroaryl and at position 4 of the cycle there is no heteroaryl group (such as pyrrole or indole) defined as substituent.

Bicyclic heterocycles, having an inhibiting effect on aggregation, are described in EP-A 0 639 575. Therein, it is a general formula (I) disclosed having a bicyclus containing the substituent A, from which an indole-derivative can be derived having at least one additional nitrogen atom in the cycle which contains the substituent A. Furthermore, a pyridazinone derivative can theoretically be derived from the substituent B having in turn a multimembered substituent, which mandatorily contains a 1,4-cyclohexylen or 1,4-cyclohex-3-enylen group and a carbonyl group. Therefore, it is evident, that the compounds of the present invention are not disclosed by EP-A 0 639 575. Compounds explicitly disclosed by EP-A 0 639 575 are no subject of the present invention.

The documents EP-A 075 436, U.S. Pat. No. 4,734,415 and U.S. Pat. No. 4,353,905 describe pyridazinone derivatives as antihypertensive agents and as agents which increase cardiac contractibility. These pyridazinone derivatives have a phenyl residue at position 6 of the pyridazinone cycle, said phenyl residue is additionally substituted with a heterocycle containing at least one nitrogen atom. Whereas the pyridazinone derivatives described in the documents EP-A 075 436 and U.S. Pat. No. 4,353,905 do not have a substituent at position 4 of the pyridazinone cycle, those disclosed in U.S. Pat. No. 4,734,415 may have an amido group substituted with lower alkyl at this position.

Thus, there exists a strong need for compounds having an inhibitory effect for CDK2. The object of the present invention is to provide compounds showing this ability.

This object is attained by pyridazinone derivatives according to the below-mentioned formula (I)

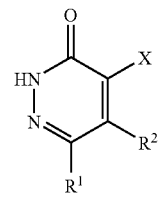
(I)

wherein:
X is a residue selected from the group consisting of:

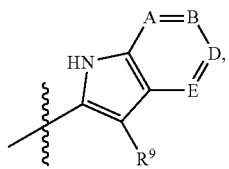
(II)

tetrazolyl and unsubstituted and at least monosubstituted triazolyl, imidazolyl, pyrrolyl and pyrazolyl,
where the substituents are selected from the group consisting of: halogen, —CN, —NO$_2$, $R^{10}$, —OR$^8$, —C(O)R$^8$, —C(O)OR$^8$, —O—C(O)R$^8$, —NR$^7$R$^8$, —NR$^7$C(O)R$^8$, —C(O)NR$^7$R$^8$, —NR$^7$C(S)R$^8$, —C(S)NR$^7$R$^8$, —SR$^8$, —S(O)R$^8$, —SO$_2$R$^8$, —NR$^7$SO$_2$R$^8$, —SO$_2$NR$^7$R$^8$, —O—SO$_2$R$^8$, —SO$_2$—O—R$^8$, aryl, heteroaryl, heterocyclyl, trifluoromethyl and trifluoromethoxy,
and aryl, heterocyclyl and heteroaryl may in turn be at least monosubstituted with C$_1$-C$_6$-alkyl, C$_1$-C$_6$-alkoxy, oxo, halogen, trifluoromethyl, trifluoromethoxy or —OH;
and each of said residues is bound to the pyridazinone fragment via the carbon atom being in α-position to the NH-fragment of said residue;
A is CR$^3$ or N;
B is CR$^4$ or N;
D is CR$^5$ or N;
E is CR$^6$ or N;
where not more than three of the substituents A, B, D and E may be N;
R$^1$ is halogen;

unsubstituted or at least monosubstituted $C_1$-$C_{10}$-alkyl,
where the substituents are selected from the group consisting of: halogen, CN, $NO_2$, $-OR^7$, $-C(O)R^7$, $-C(O)OR^7$, $-O-C(O)R^7$, $-NR^7R^8$, $-NR^8C(O)R^7$—$C(O)NR^7R^8$, $-NR^8C(S)R^7$, $-C(S)NR^7R^8$, $-SR^7$, $-S(O)R^7$, $-SO_2R^7$, $-NR^8SO_2R^7$, $-SO_2NR^7R^8$, $-O-SO_2R^7$, $-SO_2-O-R^7$, aryl, heteroaryl, heterocyclyl, trifluoromethyl and trifluoromethoxy, and aryl, heterocyclyl and heteroaryl may in turn be at least monosubstituted with $C_1$-$C_6$-alkyl, $C_1$-$C_6$-alkoxy, halogen, trifluoromethyl, trifluoromethoxy or —OH;

or unsubstituted or at least monosubstituted aryl or heteroaryl,
where the substituents are selected from the group consisting of: halogen, —CN, —$NO_2$, $R^{10}$, $-OR^7$, $-C(O)R^7$, $-C(O)OR^7$, $-O-C(O)R^7$, $-NR^7R^8$, $-NR^8C(O)R^7$, $-C(O)NR^7R^8$, $-NR^8C(S)R^7$, $-C(S)NR^7R^8$, $-SR^7$, $-S(O)R^7$, $-SO_2R^7$, $-NR^8SO_2R^7$, $-SO_2NR^7R^8$, $-O-SO_2R^7$, $-SO_2-O-R^7$, aryl, heteroaryl, trifluoromethyl and trifluoromethoxy, and aryl and heteroaryl may in turn be at least monosubstituted with $C_1$-$C_6$-alkyl, $C_1$-$C_6$-alkoxy, halogen, trifluoromethyl, trifluoromethoxy or —OH;

$R^2$ is hydrogen or $C_1$-$C_{10}$-alkyl;

$R^3$ is selected from the group consisting of:
hydrogen, halogen, —CN, —$NO_2$, $R^{10}$, $-OR^8$, $-C(O)R^8$, $-C(O)OR^8$, $-O-C(O)R^8$, $-NR^7R^8$, $-NR^7C(O)R^8$, $-C(O)NR^7R^8$, $-NR^7C(S)R^8$, $-C(S)NR^7R^8$, $-SR^8$, $-S(O)R^8$, $-SO_2R^8$, $-NR^7SO_2R^8$, $-SO_2NR^7R^8$, $-O-SO_2R^8$, $-SO_2-O-R^8$, aryl, heteroaryl, heterocyclyl, difluoromethyl, trifluoromethyl and trifluoromethoxy, and aryl, heterocyclyl and heteroaryl may in turn be at least monosubstituted with $C_1$-$C_6$-alkyl, $C_1$-$C_6$-alkoxy, oxo, halogen, trifluoromethyl, trifluoromethoxy or —OH;

$R^4$ is selected from the group consisting of:
hydrogen, halogen, —CN, —$NO_2$, $R^{10}$, $-OR^8$, $-C(O)R^8$, $-C(O)OR^8$, $-O-C(O)R^8$, $-NR^7R^8$, $-NR^7C(O)R^8$, $-C(O)NR^7R^8$, $-NR^7C(S)R^8$, $-C(S)NR^7R^8$, $-SR^8$, $-S(O)R^8$, $-SO_2R^8$, $-NR^7SO_2R^8$, $-SO_2NR^7R^8$, $-O-SO_2R^8$, $-SO_2-O-R^8$, aryl, heteroaryl, heterocyclyl, difluoromethyl, trifluoromethyl and trifluoromethoxy, and aryl, heterocyclyl and heteroaryl may in turn be at least monosubstituted with $C_1$-$C_6$-alkyl, $C_1$-$C_6$-alkoxy, oxo, halogen, trifluoromethyl, trifluoromethoxy or —OH;

$R^5$ is selected from the group consisting of:
hydrogen, halogen, —CN, —$NO_2$, $R^{10}$, $-OR^8$, $-C(O)R^8$, $-C(O)OR^8$, $-O-C(O)R^8$, $-NR^7R^8$, $-NR^7C(O)R^8$, $-C(O)NR^7R^8$, $-NR^7C(S)R^8$, $-C(S)NR^7R^8$, $-SR^8$, $-S(O)R^8$, $-SO_2R^8$, $-NR^7SO_2R^8$, $-SO_2NR^7R^8$, $-O-SO_2R^8$, $-SO_2-O-R^8$, aryl, heteroaryl, heterocyclyl, difluoromethyl, trifluoromethyl and trifluoromethoxy, and aryl, heterocyclyl and heteroaryl may in turn be at least monosubstituted with $C_1$-$C_6$-alkyl, $C_1$-$C_6$-alkoxy, oxo, halogen, trifluoromethyl, trifluoromethoxy or —OH;

$R^6$ is selected from the group consisting of:
hydrogen, halogen, —CN, —$NO_2$, $R^{10}$, $-OR^8$, $-C(O)R^8$, $-C(O)OR^8$, $-O-C(O)R^8$, $-NR^7R^8$, $-NR^7C(O)R^8$, $-C(O)NR^7R^8$, $-NR^7C(S)R^8$, $-C(S)$ $NR^7R^8$, $-SR^8$, $-S(O)R^8$, $-SO_2R^8$, $-NR^7SO_2R^8$, $-SO_2NR^7R^8$, $-O-SO_2R^8$, $-SO_2-O-R^8$, aryl, heteroaryl, heterocyclyl, difluoromethyl, trifluoromethyl and trifluoromethoxy, and aryl, heterocyclyl and heteroaryl may in turn be at least monosubstituted with $C_1$-$C_6$-alkyl, $C_1$-$C_6$-alkoxy, oxo, halogen, trifluoromethyl, trifluoromethoxy or —OH;

$R^7$ is H;
or unsubstituted or at least monosubstituted $C_1$-$C_{10}$-alkyl, $C_2$-$C_{10}$-alkenyl, $C_2$-$C_{10}$-alkynyl, heterocyclyl, aryl or heteroaryl,
where the substituents are selected from the group consisting of: heteroaryl, heterocyclyl, aryl, oxo, halogen, —OH, $C_1$-$C_{10}$-alkyl, $C_1$-$C_{10}$-alkoxy, ($C_1$-$C_{10}$-alkyl)thio-, —C(O)OH, —C(O)O—($C_1$-$C_6$-alkyl), —C(O)$NH_2$, trifluoromethyl, trifluoromethoxy, —CN, —$NH_2$, —NH($C_1$-$C_{10}$-alkyl) and —N($C_1$-$C_{10}$-alkyl)$_2$, and aryl, heterocyclyl and heteroaryl may in turn be at least monosubstituted with $C_1$-$C_6$-alkyl, $C_1$-$C_6$-alkoxy, oxo, halogen, trifluoromethyl, trifluoromethoxy or —OH;

$R^8$ is H;
or unsubstituted or at least monosubstituted $C_1$-$C_{10}$-alkyl, $C_2$-$C_{10}$-alkenyl, $C_2$-$C_{10}$-alkynyl, heterocyclyl, aryl or heteroaryl,
where the substituents are selected from the group consisting of: heteroaryl, heterocyclyl, aryl, halogen, —OH, oxo, $C_1$-$C_{10}$-alkyl, $C_1$-$C_{10}$-alkoxy, ($C_1$-$C_{10}$-alkyl)thio-, —C(O)OH, —C(O)O—($C_1$-$C_6$-alkyl), —C(O)$NH_2$, trifluoromethyl, trifluoromethoxy, —CN, —$NH_2$, —NH($C_1$-$C_{10}$-alkyl) and —N($C_1$-$C_{10}$-alkyl)$_2$, and aryl, heterocyclyl and heteroaryl may in turn be at least monosubstituted with $C_1$-$C_6$-alkyl, $C_1$-$C_6$-alkoxy, oxo, halogen, trifluoromethyl, trifluoromethoxy or —OH;

$R^9$ is selected from the group consisting of:
hydrogen, halogen, —CN, —$NO_2$, $R^{10}$, $-OR^8$, $-C(O)R^8$, $-C(O)OR^8$, $-O-C(O)R^8$, $-NR^7R^8$, $-NR^7C(O)R^8$, $-C(O)NR^7R^8$, $-NR^7C(S)R^8$, $-C(S)NR^7R^8$, $-SR^8$, $-S(O)R^8$, $-SO_2R^8$, $-NR^7SO_2R^8$, $-SO_2NR^7R^8$, $-O-SO_2R^8$, $-SO_2-O-R^8$, aryl, heteroaryl, heterocyclyl, trifluoromethyl and trifluoromethoxy, and aryl, heterocyclyl and heteroaryl may in turn be at least monosubstituted with $C_1$-$C_6$-alkyl, $C_1$-$C_6$-alkoxy, oxo, halogen, trifluoromethyl, trifluoromethoxy or —OH;

$R^{10}$ is unsubstituted or at least monosubstituted $C_1$-$C_{10}$-alkyl, $C_2$-$C_{10}$-alkenyl or $C_2$-$C_{10}$-alkynyl,
where the substituents are selected from the group consisting of: heteroaryl, heterocyclyl, aryl, halogen, —OH, oxo, $C_1$-$C_{10}$-alkoxy, ($C_1$-$C_{10}$-alkyl)thio-, —C(O)OH, —C(O)O—($C_1$-$C_6$-alkyl), —C(O)$NH_2$, trifluoromethyl, trifluoromethoxy, —CN, —$NH_2$, —NH($C_1$-$C_{10}$-alkyl) and —N($C_1$-$C_{10}$-alkyl)$_2$.

and aryl, heterocyclyl and heteroaryl may in turn be at least monosubstituted with $C_1$-$C_6$-alkyl, $C_1$-$C_6$-alkoxy, —C(O)—($C_1$-$C_6$-alkyl), oxo, halogen, trifluoromethyl, trifluoromethoxy or —OH;

Heteroaryl is a 5 to 10-membered, aromatic, mono- or bicyclic heterocycle containing one or more heteroatoms selected from the group consisting of N, O and S;

Aryl is a 6 to 10-membered, aromatic mono- or bicyclus;

Heterocyclyl is a 4- to 10-membered, non-aromatic, mono- or bicyclic heterocycle containing one or more heteroatoms selected from the group consisting of N, O and S, or a physiologically acceptable salt thereof.

The above mentioned meanings of the substituents $R^1$ to $R^{10}$, A, B, D, E, X, aryl, heteroaryl and heterocyclyl are the basic meanings (definitions) of the respective substituents.

If in the compounds of formula (I) groups, fragments, residues or substituents such as, for example, aryl, heteroaryl, alkyl etc., are present several times, they all independently from each other have the meanings indicated and may hence, in each individual case, be identical with or different from each other. The following comments apply to (for example) aryl as well as to any other residue independently from its classification as aryl group, -substituent, -fragment or -residue. Another example is the —$N(C_1$-$C_3$-alkyl$)_2$ group in which the alkyl substituents may be identical or different (for instance 2× ethyl or 1× propyl and 1× methyl). If in the above-mentioned definitions of compounds according to formula (I) a substituent, for example aryl, is unsubstituted or at least mono-substituted with a group of further substituents, for example, $C_1$-$C_3$-alkyl, $C_1$-$C_3$-alkoxy, halogen etc., it applies in such cases, where there is a poly-substitution of aryl, that the selection from the group of further substituents is independently from each other. Thus, all combinations of further substituents are comprised in the case of, for example, a double-substitution of aryl. Therefore, aryl may be substituted twice with ethyl, aryl may be mono-substituted with methyl or ethoxy, respectively, aryl may be mono-substituted with ethyl or fluoro, respectively, aryl may be substituted twice with methoxy, etc.

Alkyl, alkenyl and alkynyl residues may be linear or branched, acyclic or cyclic. This also applies when they are part of other groups, for example in alkoxy groups ($C_1$-$C_{10}$-alkyl-O—), alkoxycarbonyl groups or amino groups, or when they are substituted.

Examples for alkyl groups are: methyl, ethyl, propyl, butyl, pentyl, hexyl, heptyl, octyl, nonyl, decyl. This comprises both the n-isomers of these residues and isopropyl, isobutyl, isopentyl, sec-butyl, tert-butyl, neopentyl, 3,3-dimethylbutyl etc. Furthermore, unless stated otherwise, the term alkyl here also includes unsubstituted alkyl residues as well as alkyl residues which are substituted by one or more, for example one, two, three or four, identical or different residues, for example aryl, heteroaryl, alkoxy or halogen. The substituents may be present in any desired position of the alkyl group. The term alkyl here also expressly includes cycloalkyl residues and cycloalkyl-alkyl-residues (alkyl substituted by cycloalkyl), where cycloalkyl contains at least three carbon atoms. Examples for such cycloalkyl residues are cyclopropyl, cyclobutyl, cyclopentyl, cyclohexyl, cycloheptyl and cyclooctyl. All cycloalkyl groups may be unsubstituted or optionally substituted by one or more further residues, as exemplified above in the case of the alkyl groups.

Examples for alkenyl and alkynyl groups are the vinyl residue, the 1-propenyl residue, the 2-propenyl residue (allyl residue), the 2-butenyl residue, the 2-methyl-2-propenyl residue, the 3-methyl-2-butenyl residue, the ethynyl residue, the 2-propynyl residue (propargyl residue), the 2-butynyl residue or the 3-butynyl residue. The term alkenyl here also expressly includes cycloalkenyl residues and cycloalkenyl-alkyl-residues (alkyl substituted by cycloalkenyl) containing at least three carbon atoms. Examples for cycloalkenyl residues are cyclopentenyl, cyclohexenyl, cycloheptenyl and cyclooctenyl.

The alkenyl residues may have 1 to 3 conjugated or unconjugated double bonds (thus also alk-dienyl- as well as alk-trienyl-residues), preferably one double bond in a straight or branched chain; the same applies to alkynyl residues in respect of triple bonds. The alkenyl and alkynyl residues may be unsubstituted or optionally substituted by one or more further residues, as exemplified above in the case of the alkyl groups.

Unless stated otherwise, the above-mentioned aryl, heteroaryl and heterocyclic residues may be unsubstituted or may carry one or more, for example one, two, three or four of the substituents indicated in the above definition, which substituents may be in any desired position. In monosubstituted phenyl residues, for example, the substituent may be in the 2-position, the 3-position or the 4-position, in disubstituted phenyl residues the substituents may be in 2,3-position, 2,4-position, 2,5-position, 2,6-position, 3,4-position or 3,5-position. In trisubstituted phenyl residues the substituents may be in 2,3,4-position, 2,3,5-position, 2,3,6-position, 2,4,5-position, 2,4,6-position or 3,4,5-position. In fourfold substituted phenyl residues, the substituents may be in the 2,3,4,5-position, the 2,3,4,6-position, or the 2,3,5,6-position.

The above definitions as well as the following definitions relating to monovalent residues equally apply to the divalent residues phenylene, naphthylene and heteroarylene. Those divalent residues (fragments) may be attached to the adjacent groups by any ring carbon atom. In the case of a phenylene residue, these may be in 1,2-position (ortho-phenylene), 1,3-position (meta-phenylene) or 1,4-position (para-phenylene). In the case of 5-membered ring aromatics containing one heteroatom such as, for example, thiophene or furan, the two free bonds may be in 2,3-position, 2,4-position, 2,5-position or 3,4-position. A divalent residue derived from pyridine may be a 2,3-, 2,4-, 2,5-, 2,6-, 3,4- or 3,5-pyridinediyl residue. In the case of unsymmetrical divalent residues the present invention includes all positional isomers, i.e., in the case of a 2,3-pyridinediyl residue, for example, it includes the compound in which the one adjacent group is present in the 2-position and the other adjacent group is present in the 3-position as well as the compound in which the one adjacent group is present in the 3-position and the other adjacent group is present in the 2-position.

Unless stated otherwise, heteroaryl residues, heteroarylene residues, heterocyclyl residues, heterocyclylene residues and rings which are formed by two groups bonded to a nitrogen are preferably derived from completely saturated, partially unsaturated or completely unsaturated heterocycles (i.e. heterocycloalkanes, heterocycloalkenes, heteroaromatics), which contain one, two, three or four heteroatoms, which may be identical or different; more preferably they are derived from heterocycles which contain one, two, or three, in particular one or two, heteroatoms, which may be identical or different. Unless stated otherwise, the heterocycles may be monocyclic or polycyclic, for example monocyclic, bicyclic or tricyclic. Preferably they are monocyclic or bicyclic. The rings preferably are 5-membered rings, 6-membered rings or 7-membered rings. In the case of polycyclic heterocycles containing two or more heteroatoms, they may all be within the same cycle or within different cycles.

According to the present invention, heteroaryl is a residue derived from mono- or bicyclic aromatic heterocycles. Examples of heteroaryl are: pyrrolyl, furanyl (=furyl), thiophenyl (=thienyl), imidazolyl, pyrazolyl, 1,2,3-triazolyl, 1,2,4-triazolyl, 1,3-oxazolyl (=Oxazolyl), 1,2-oxazolyl (=isoxazolyl), oxadiazolyl, 1,3-thiazolyl (=thiazolyl), 1,2-thiazolyl (=isothiazolyl), tetrazolyl, pyridinyl (=pyridyl)pyridazinyl, pyrimidinyl, pyrazinyl, 1,2,3-triazinyl, 1,2,4-triazinyl, 1,3,5-triazinyl, 1,2,4,5-tetrazinyl, indazolyl, indolyl, benzothienyl, benzofuranyl, benzothiazolyl, benzimidazolyl, quinolinyl (=quinolyl), isoquinolinyl (=isoquinolyl), quinazolinyl, quinoxalinyl, phthalazinyl, thienothiophenyl, 1,8-naphthyridinyl, other naphthyridinyl, pteridinyl or thiazolo[3,2-b][1,2,4]-triazolyl. In case it is not a monocycle, each of the above heteroaryls includes for its second cycle also its saturated form (perhydro form) or its partially unsaturated form (for example in the dihydro form or the tetrahydro form) in case the respective forms are known and stable. The term "heteroaryl" as used herein comprises therefore, for example, bicyclic residues in which both cycles are aromatic as well as bicyclic residues in which only one cycle is aromatic. Such examples for heteroaryl are: 3H-indolinyl, 2(1H)-quinolinonyl, 4-oxo-1,4-dihydroquinolinyl, 2H-1-oxoisoquinolyl, 1,2-dihydroquinolinyl, 3,4-dihydroquinolinyl, 1,2-dihydroisoquinolinyl, 3,4-dihydroisoquinolinyl, chromonyl, chromanyl, 1,3-benzodioxolyl, oxindolyl, 1,2,3,4-tetrahydroisoquinolinyl, 1,2,3,4-tetrahydroquinolinyl, 5,6-dihydroquinolyl, 5,6-dihydroisoquinolyl, 5,6,7,8-tetrahydroquinolinyl or 5,6,7,8-tetrahydroisoquinolyl.

According to the present invention, heterocyclyl is a residue derived from mono- or bicyclic non-aromatic heterocycles. Non-aromatic heterocycles comprise in the following especially heterocycloalkanes (completely saturated heterocycles) as well as heterocycloalkenes (partially unsaturated heterocycles). In the case of heterocycloalkenes there are also included compounds having two or more double bonds, which may optionally be conjugated. Examples of heterocyclyl are: pyrrolidinyl, piperidinyl, piperazinyl, imidazolidinyl, pyrazolidinyl, isothiazolidinyl, thiazolidinyl, isoxazolidinyl, oxazolidinyl, tetrahydrofuranyl, tetrahydrothiophenyl 1,3-dioxolanyl, 1,4-dioxinyl, pyranyl, thiopyranyl, tetrahydro-1,2-oxazinyl, tetrahydro-1,3-oxazinyl, morpholinyl, thiomorpholinyl, 1,2-thiazinyl, 1,3-thiazinyl, 1,4-thiazinyl, azepinyl, 1,2-diazepinyl, 1,3-diazepinyl, 1,4-diazepinyl, 1,3-oxazepinyl, 1,3-thiazepinyl, azepanyl, 2-oxo-azepanyl, 1,2,3,4-tetrahydropyridinyl, 1,2-dihydropyridinyl, 1,4-dihydropyridinyl, 1,2,3,6-tetrahydropyridinyl, 4(3H)-pyrimidonyl, 1,4,5,6-tetrahydropyrimidinyl, 2-pyrrolinyl, 3-pyrrolinyl, 2-imidazolinyl, 2-pyrazolinyl, 3,4-dihydro-2H-pyranyl, dihydrofuranyl, 7-oxabicyclo[2.2.1]heptenyl, dihydrothienyl or dihydrothiopyranyl. The degree of saturation of heterocyclic groups is indicated in their individual definitions.

Substituents which may be derived from these heterocycles may be attached via any suitable carbon atom. Residues derived from nitrogen heterocycles may carry a hydrogen atom or a substituent on a ring nitrogen atom, and examples include pyrrole, imidazole, pyrrolidine, morpholine, piperazine residues, etc. Those nitrogen heterocyclic residues may also be attached via a ring nitrogen atom, in particular if the respective heterocyclic residue is bonded to a carbon atom. For example, a thienyl residue may be present as 2-thienyl or 3-thienyl, a piperidinyl residue as 1-piperidinyl (=piperidino), 2-piperidinyl, 3-piperidinyl or 4-piperidinyl. Suitable nitrogen heterocycles may also be present as N-oxides or as quaternary salts containing a counterion which is derived from a physiologically acceptable acid. Pyridyl residues, for example, may be present as pyridine-N-oxides. Suitable sulfur-containing heterocycles may be present as S-oxide or S—S-dioxide.

According to the present invention, aryl is a residue derived from mono- or bicyclic aromatics, where the cycle does not contain any heteroatoms. In case it is not a monocycle, the term aryl includes for its second cycle also its saturated form (perhydro form) or its partially unsaturated form (for example in the dihydro form or the tetrahydro form) in case the respective forms are known and stable. The term aryl as used herein comprises therefore, for example, bicyclic residues in which both cycles are aromatic as well as bicyclic residues in which only one cycle is aromatic. Such examples for heteroaryl are: phenyl, naphthyl, indanyl, 1,2-dihydronaphthenyl, 1,4-dihydronaphthenyl, indenyl or 1,2,3,4-tetrahydronaphthyl. Arylalkyl (such as aryl-($C_1$-$C_6$-alkyl)-) means an alkyl residue (such as $C_1$-$C_6$-alkyl), which in turn is substituted by an aryl residue. Heteroarylalkyl (such as heteroaryl-($C_1$-$C_6$-alkyl)-) means an alkyl residue (such as $C_1$-$C_6$-alkyl), which in turn is substituted by a heteroaryl residue. Heterocyclylalkyl (such as heterocyclyl-($C_1$-$C_6$-alkyl)-) means an alkyl residue (such as $C_1$-$C_6$-alkyl), which in turn is substituted by a heterocyclyl residue. Such arylalkyl, heteroarylalkyl or heterocyclylalkyl residues may themselves be a substituent of another substituent or fragment (such as heterocyclyl-($C_1$-$C_6$-alkyl)-NH—), which means that a substituent or fragment (such as —NH—) in turn is substituted by a heterocyclylalkyl residue (such as heterocyclyl-($C_1$-$C_6$-alkyl)-). Further possible substitutions of an alkyl residue include examples such as $H_2N$—($C_1$-$C_6$-alkyl)-, ($C_1$-$C_6$-alkyl)HN—($C_1$-$C_6$-alkyl)- or ($C_1$-$C_6$-alkyl)$_2$N—($C_1$-$C_6$-alkyl)-, which means an alkyl residue (such as $C_1$-$C_6$-alkyl), which in turn is substituted by —$NH_2$, —NH($C_1$-$C_6$-alkyl) or —N($C_1$-$C_6$-alkyl)$_2$, respectively. Additionally, a residue such as ($C_1$-$C_6$-alkyl)HN—($C_1$-$C_6$-alkyl) may itself be a substituent of another substituent or fragment (such as ($C_1$-$C_6$-alkyl)HN—($C_1$-$C_6$-alkyl)-O—), which means that a substituent or fragment (such as —O—) in turn is substituted by a substituted alkyl residue (such as ($C_1$-$C_6$-alkyl)HN—($C_1$-$C_6$-alkyl)-). For the definitions and possible substitutions of alkyl, heteroaryl, heterocyclyl and aryl it is referred to the above-mentioned definitions.

Halogen is fluorine, chlorine, bromine or iodine, preferably fluorine, chlorine or bromine, most preferably fluorine or chlorine.

The present invention includes all stereoisomeric forms of the compounds of the formula (I). Centers of asymmetry that are present in the compounds of formula (I) all independently of one another have S configuration or R configuration. The invention includes all possible enantiomers and diastereomers and mixtures of two or more stereoisomers, for example mixtures of enantiomers and/or diastereomers, in all ratios. Thus, compounds according to the present invention which may exist as enantiomers may be present in enantiomerically pure form, both as levorotatory and as dextrorotatory antipodes, in the form of racemates and in the form of mixtures of the two enantiomers in all ratios. In the case of a cis/trans isomerism the invention includes both: the cis form and the trans form as well as mixtures of these forms in all ratios. All these forms are an object of the present invention. The preparation of individual stereoisomers may be carried out, if desired, by separation of a mixture by customary methods, for example by chromatography or crystallization, by the use of stereochemically uniform starting materials for the synthesis or by stereoselective synthesis. Optionally, a derivatization may be carried out before a separation of stereoisomers. The separation of a mixture of stereoisomers may be carried out at the stage of the compounds of the formula (I) or at the stage of an intermediate during the synthesis. The present invention also includes all tautomeric forms of the compounds of formula (I), in particular keto-enol tautomerism, i.e. the respective compounds may be present either in their keto form or in their enol form or in mixtures thereof in all ratios.

In case the compounds according to formula (I) contain one or more acidic or basic groups, the invention also comprises their corresponding physiologically or toxicologically acceptable salts.

Physiologically acceptable salts are particularly suitable for medical applications, due to their greater solubility in water compared with the starting or base compounds. Said salts must have a physiologically acceptable anion or cation. Suitable physiologically acceptable acid addition salts of the compounds of the invention are salts of inorganic acids such as hydrochloric acid, hydrobromic acid, phosphoric acid, metaphosphoric acid, nitric acid, sulfonic acid and sulfuric acid and also of organic acids such as, for example, acetic acid, theophyllinacetic acid, methylene-bis-b-oxynaphthoic acid, benzenesulfonic acid, benzoic acid, citric acid, ethanesulfonic acid, salicylic acid, fumaric acid, gluconic acid, glycolic acid, isethionic acid, lactic acid, lactobionic acid, maleic acid, malic acid, methanesulfonic acid, succinic acid, p-toluenesulfonic acid, tartaric acid and trifluoroacetic acid. Suitable pharmaceutically acceptable basic salts are ammonium salts, alkali metal salts (such as sodium salts and potassium salts) and alkaline earth metal salts (such as magnesium salts and calcium salts).

Salts having a pharmaceutically unacceptable anion are likewise included within the scope of the present invention as useful intermediates for preparing or purifying pharmaceutically acceptable salts and/or for use in nontherapeutic applications, for example in-vitro applications.

If the compounds of the formula (I) simultaneously contain acidic and basic groups in the molecule, the invention also includes, in addition to the salt forms mentioned, inner salts or betaines (zwitterions).

The respective salts according to the formula (I) may be obtained by customary methods which are known to the person skilled in the art like, for example by contacting these with an organic or inorganic acid or base in a solvent or dispersant, or by anion exchange or cation exchange with other salts.

The present invention furthermore includes all solvates of compounds of the formula (I), for example hydrates or adducts with alcohols, active metabolites of the compounds of the formula (I), and also derivatives, which contain physiologically tolerable and cleavable groups, for example esters or amides.

The term "physiologically functional derivative" used herein relates to any physiologically acceptable derivative of an inventive compound of the formula I, for example an ester which on administration to a mammal, for example humans, is capable of forming (directly or indirectly) a compound of the formula I or an active metabolite thereof.

The physiologically functional derivatives also include prodrugs of the compounds of the invention. Such prodrugs may be metabolized in vivo to a compound of the invention. These prodrugs may or may not be active themselves and are also an object of the present invention.

The compounds of the invention may also be present in various polymorphous forms, for example as amorphous and crystalline polymorphous forms. All polymorphous forms of the compounds of the invention are included within the scope of the invention and are another aspect of the invention.

Preferred compounds of the formula (I) are those compounds in which one or more, including all, of the above-mentioned substituents $R^1$ to $R^{10}$, A, B, D, E, X, aryl, heteroaryl and heterocyclyl of the formula (I) independently from each other have the following meanings (definitions), with all possible (if defined) combinations of the preferred meanings, the more preferred meanings, the much more preferred meanings, the particularly preferred meanings or the exceptionally preferred meanings, also in combination with substituents having their basic meanings, being a subject of the present invention.

X is preferably a residue selected from the group consisting of:

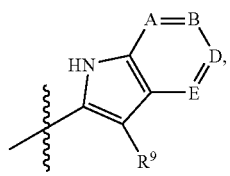

(II)

and unsubstituted and at least monosubstituted pyrrolyl,
where the substituents are selected from the group consisting of: halogen, —CN, $R^{10}$, —$OR^8$, —$C(O)R^8$, —$C(O)OR^8$, —$NR^8H$, —$NR^8(C_1-C_6\text{-alkyl})$, —$C(O)NR^8H$, —$SR^8$, —$SO_2NR^8H$, —$SO_2R^8$, aryl, heteroaryl, heterocyclyl, difluoromethyl, trifluoromethyl and trifluoromethoxy,
and aryl, heterocyclyl and heteroaryl may in turn be at least monosubstituted with $C_1$-$C_6$-alkyl, $C_1$-$C_6$-alkoxy, oxo, halogen, trifluoromethyl, trifluoromethoxy or —OH;
and each of said residues is bound to the pyridazinone fragment via the carbon atom being in α-position to the NH-fragment of said residue;

X is more preferably a residue selected from the group consisting of:

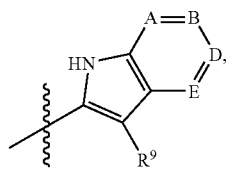

(II)

and unsubstituted and at least monosubstituted pyrrolyl,
where the substituents are selected from the group consisting of: halogen, $R^{10}$, —$OR^8$, —$C(O)R^8$, —$C(O)NR^8H$, phenyl, heteroaryl, heterocyclyl, trifluoromethyl and trifluoromethoxy,
and phenyl, heterocyclyl and heteroaryl may in turn be at least monosubstituted with $C_1$-$C_6$-alkyl, $C_1$-$C_6$-alkoxy, oxo, halogen, trifluoromethyl, trifluoromethoxy or —OH;
and each of said residues is bound to the pyridazinone fragment via the carbon atom being in α-position to the NH-fragment of said residue;

X is much more preferably a residue selected from the group consisting of:

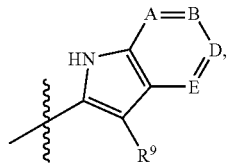

(II)

and unsubstituted and at least monosubstituted pyrrolyl,
where the substituents are selected from the group consisting of: halogen, $R^{10}$, —$OR^8$, —$C(O)$—$(C_1$-$C_6$-alkyl), —$C(O)NR^8H$, phenyl, pyridinyl, imidazolyl, trifluoromethyl and trifluoromethoxy, and phenyl, pyridinyl and imidazolyl may in turn be at least monosubstituted with $C_1$-$C_6$-alkyl, $C_1$-$C_6$-alkoxy, halogen, trifluoromethyl, trifluoromethoxy or —OH;

and each of said residues is bound to the pyridazinone fragment via the carbon atom being in α-position to the NH-fragment of said residue;

X is particularly preferred a residue selected from the group consisting of:

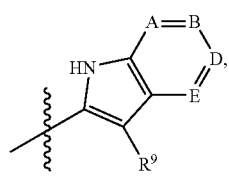

(II)

and unsubstituted and at least monosubstituted pyrrolyl,
where the substituents are selected from the group consisting of: fluoro; chloro; bromo; trifluoromethyl; trifluoromethoxy;
unsubstituted and at least monosubstituted phenoxy, phenyl and pyridinyl,
where the substituents are selected from the group consisting of:
$C_1$-$C_6$-alkyl, $C_1$-$C_6$-alkoxy, fluoro, chloro, trifluoromethyl, trifluoromethoxy and —OH;
and unsubstituted and at least monosubstituted $C_1$-$C_6$-alkyl and $C_1$-$C_6$-alkoxy,
where the substituents are selected from the group consisting of: phenyl, pyridinyl, morpholinyl, piperazinyl, piperidinyl, imidazolyl, pyrrolidinyl, —$NH_2$, —NH($C_1$-$C_6$-alkyl) and —N($C_1$-$C_6$-alkyl)$_2$,
and phenyl, azetidinyl, pyridinyl, morpholinyl, piperazinyl, piperidinyl, imidazolyl and pyrrolidinyl may in turn be monosubstituted with $C_1$-$C_3$-alkyl, $C_1$-$C_3$-alkoxy, trifluoromethyl, trifluoromethoxy, fluoro, chloro or —OH;
and each of said residues is bound to the pyridazinone fragment via the carbon atom being in α-position to the NH-fragment of said residue;

A is preferably $CR^3$;
B is preferably $CR^4$;
D is preferably $CR^5$;
E is preferably $CR^6$;

Unless each of the substituents A, B, D and E has its preferred meaning, preferably only two of the substituents A, B, D and E are N; more preferably only one of the substituents A, B, D and E is N;

$R^1$ is preferably:
unsubstituted or at least monosubstituted $C_1$-$C_6$-alkyl,
where the substituents are selected from the group consisting of: fluoro, chloro, —OH, $C_1$-$C_6$-alkoxy, —$NH_2$, —NH($C_1$-$C_6$-alkyl), —N($C_1$-$C_6$-alkyl)$_2$, heterocyclyl-($C_1$-$C_6$-alkyl)-NH—, aryl-($C_1$-$C_6$-alkyl)-NH—, heterocyclyl, aryl and heteroaryl,
and the aryl-, heterocyclyl- and heteroaryl-fragments of said substituents may in turn be at least monosubstituted with $C_1$-$C_4$-alkyl, $C_1$-$C_4$-alkoxy, fluoro, chloro, trifluoromethyl, trifluoromethoxy or —OH;
or unsubstituted or at least monosubstituted aryl or heteroaryl,
where the substituents are selected from the group consisting of: halogen, $R^{10}$, —$OR^7$, —$C(O)R^7$, —$C(O)OR^7$, —$NR^7H$, —$NR^7(C_1$-$C_6$-Alkyl), —$C(O)NR^7H$, —$SR^7$, aryl, heteroaryl, trifluoromethyl and trifluoromethoxy,
and aryl and heteroaryl may in turn be at least monosubstituted with $C_1$-$C_6$-alkyl, $C_1$-$C_6$-alkoxy, halogen, trifluoromethyl, trifluoromethoxy or —OH;

$R^1$ is more preferably:
unsubstituted or at least monosubstituted phenyl, pyridinyl, pyrimidinyl, pyrazolyl, thienyl, oxazolyl, isoxazolyl, 1H-pyrrolo[2,3-b]pyridinyl, benzo[b]thienyl, benzodioxolyl or thiazolo[3,2-b][1,2,4]-triazolyl,
where the substituents are selected from the group consisting of: halogen, $R^{10}$, —$OR^7$, —$C(O)R^7$, —$C(O)OR^7$, —$NR^7H$, —$NR^7(C_1$-$C_6$-Alkyl), —$C(O)NR^7H$, —$SR^7$, aryl, heteroaryl, trifluoromethyl and trifluoromethoxy,
and aryl and heteroaryl may in turn be at least monosubstituted with $C_1$-$C_6$-alkyl, $C_1$-$C_6$-alkoxy, halogen, trifluoromethyl, trifluoromethoxy or —OH;

$R^1$ is much more preferably:
unsubstituted or at least monosubstituted phenyl, pyridinyl, pyrimidinyl, pyrazolyl, thienyl, oxazolyl, isoxazolyl, 1H-pyrrolo[2,3-b]pyridinyl, benzo[b]thienyl, benzodioxolyl or thiazolo[3,2-b][1,2,4]-triazolyl,
where the substituents are selected from the group consisting of: halogen, $C_1$-$C_6$-alkyl, phenyl-($C_1$-$C_6$-alkyl)-, —OH, $C_1$-$C_6$-alkoxy, ($C_1$-$C_6$-alkyl)thio-, —O-phenyl, —$NH_2$, —N($C_1$-$C_6$-alkyl)$_2$, —NH($C_1$-$C_6$-alkyl), $H_2N$—($C_1$-$C_6$-alkyl)-NH—, ($C_1$-$C_6$-alkyl)HN—($C_1$-$C_6$-alkyl)-NH—, ($C_1$-$C_6$-alkyl)$_2$N—($C_1$-$C_6$-alkyl)-NH—, heterocyclyl-($C_1$-$C_6$-alkyl)-NH—, heteroaryl-($C_1$-$C_6$-alkyl)-NH—, phenyl-($C_1$-$C_6$-alkyl)-NH—, trifluoromethyl, trifluoromethoxy, phenyl and heteroaryl,
and the phenyl-, heterocyclyl- and heteroaryl-fragments of said substituents may in turn be at least monosubstituted with $C_1$-$C_3$-alkyl, $C_1$-$C_3$-alkoxy, fluoro, chloro, trifluoromethyl, trifluoromethoxy or —OH;

$R^1$ is particularly preferred:
unsubstituted or at least monosubstituted phenyl, thienyl, pyrazolyl, pyridinyl or pyrimidinyl,
where the substituents are selected from the group consisting of: $C_1$-$C_4$-alkyl, —OH, $C_1$-$C_4$-alkoxy, ($C_1$-$C_4$-alkyl)thio-, trifluoromethyl, trifluoromethoxy and —NH($C_1$-$C_4$-alkyl),
and —NH($C_1$-$C_4$-alkyl) may in turn be at least monosubstituted with phenyl, piperazinyl, piperidinyl or morpholinyl.

$R^1$ is exceptionally preferred:
pyridin-4-yl, 2-ethylamino-pyridin-4-yl, 2-methylamino-pyrimidin-4-yl, 2-ethylamino-pyrimidin-4-yl, 2-butylamino-pyrimidin-4-yl, 2-(2-morpholin-4-ylethylamino-)pyrimidin-4-yl, pyrazol-4-yl, 3-methoxy-4-hydroxy-phenyl, 4-hydroxy-phenyl or 3-fluoro-4-hydroxy-phenyl, $R^2$ is preferably hydrogen or $C_1$-$C_6$-alkyl; $R^2$ is particularly preferred hydrogen.

$R^3$ is preferably selected from the group consisting of:
hydrogen, halogen, —CN, $R^{10}$, —$OR^8$, —$C(O)R^8$, —$C(O)OR^8$, —$NR^8H$, —$NR^8(C_1$-$C_6$-alkyl), —$C(O)NR^8H$, —$SR^8$, —$SO_2NR^8H$, —$SO_2R^8$, aryl, heteroaryl, heterocyclyl, difluoromethyl, trifluoromethyl and trifluoromethoxy,
and aryl, heterocyclyl and heteroaryl may in turn be at least monosubstituted with $C_1$-$C_6$-alkyl, $C_1$-$C_6$-alkoxy, oxo, halogen, trifluoromethyl, trifluoromethoxy or —OH;

$R^3$ is more preferably selected from the group consisting of:
hydrogen, fluoro, chloro, bromo, $R^{10}$, —$OR^8$, —$C(O)NR^8H$, trifluoromethyl and trifluoromethoxy, R³ is much more preferably selected from the group consisting of:
- hydrogen, fluoro, chloro, bromo, $C_1$-$C_6$-alkyl, heterocyclyl-($C_1$-$C_6$-alkyl)-, $H_2N$—($C_1$-$C_6$-alkyl)-, ($C_1$-$C_6$-alkyl)HN—($C_1$-$C_6$-alkyl)-, ($C_1$-$C_6$-alkyl)$_2$N—($C_1$-$C_6$-alkyl)-, —OH, $C_1$-$C_6$-alkoxy, heterocyclyl-($C_1$-$C_6$-alkyl)-O—, $H_2N$—($C_1$-$C_6$-alkyl)-O—, ($C_1$-$C_6$-alkyl)HN—($C_1$-$C_6$-alkyl)-O—, ($C_1$-$C_6$-alkyl)$_2$N—($C_1$-$C_6$-alkyl)-O—, —C(O)N($C_1$-$C_6$-alkyl)$_2$, —C(O)NH($C_1$-$C_6$-alkyl), $H_2N$—($C_1$-$C_6$-alkyl)-NHC(O)—, HO—($C_1$-$C_6$-alkyl)-NHC(O)—, ($C_1$-$C_6$-alkyl)HN—($C_1$-$C_6$-alkyl)-NHC(O)—, ($C_1$-$C_6$-alkyl)$_2$N—($C_1$-$C_6$-alkyl)-NHC(O)—, heterocyclyl-($C_1$-$C_6$-alkyl)-NHC(O)—, trifluoromethyl and trifluoromethoxy,
- and the heterocyclyl-fragments of said substituents may in turn be at least monosubstituted with $C_1$-$C_3$-alkyl, $C_1$-$C_3$-alkoxy, fluoro, chloro, trifluoromethyl, trifluoromethoxy or —OH;

R³ is particularly preferred selected from the group consisting of:
- hydrogen, fluoro, chloro, 2-dimethylamino-ethoxy, 2-diethylamino-ethoxy, 3-dimethylamino-propoxy, 3-diethylamino-propoxy, dimethylamino-methyl, diethylamino-methyl, methoxy, ethoxy, piperidin-1-ylmethyl, 2-piperidin-1-yl-ethoxy, 4-methyl-piperazin-1-ylmethyl, morpholin-4-ylmethyl, 2-(4-methyl-piperazin-1-yl)-ethoxy, methyl, ethyl, trifluoromethyl and trifluoromethoxy;

R³ is exceptionally preferred selected from the group consisting of:
- hydrogen;

R⁴ is preferably selected from the group consisting of:
- hydrogen, halogen, —CN, $R^{10}$, —$OR^8$, —C(O)$R^8$, —C(O)$OR^8$, —$NR^8H$, —$NR^8$($C_1$-$C_6$-alkyl), —C(O)$NR^8H$, —$SR^8$, —$SO_2NR^8H$, —$SO_2R^8$, aryl, heteroaryl, heterocyclyl, difluoromethyl, trifluoromethyl and trifluoromethoxy,
- and aryl, heterocyclyl and heteroaryl may in turn be at least monosubstituted with $C_1$-$C_6$-alkyl, $C_1$-$C_6$-alkoxy, oxo, halogen, trifluoromethyl, trifluoromethoxy or —OH;

R⁴ is more preferably selected from the group consisting of:
- hydrogen, fluoro, chloro, bromo, $R^{10}$, —$OR^8$, —C(O)$NR^8H$, trifluoromethyl and trifluoromethoxy, R⁴ is much more preferably selected from the group consisting of:
- hydrogen, fluoro, chloro, bromo, $C_1$-$C_6$-alkyl, heterocyclyl-($C_1$-$C_6$-alkyl)-, $H_2N$—($C_1$-$C_6$-alkyl)-, ($C_1$-$C_6$-alkyl)HN—($C_1$-$C_6$-alkyl)-, ($C_1$-$C_6$-alkyl)$_2$N—($C_1$-$C_6$-alkyl)-, —OH, $C_1$-$C_6$-alkoxy, heterocyclyl-($C_1$-$C_6$-alkyl)-O—, $H_2N$—($C_1$-$C_6$-alkyl)-O—, ($C_1$-$C_6$-alkyl)HN—($C_1$-$C_6$-alkyl)-O—, ($C_1$-$C_6$-alkyl)$_2$N—($C_1$-$C_6$-alkyl)-O—, —C(O)N($C_1$-$C_6$-alkyl)$_2$, —C(O)NH($C_1$-$C_6$-alkyl), $H_2N$—($C_1$-$C_6$-alkyl)-NHC(O)—, HO—($C_1$-$C_6$-alkyl)-NHC(O)—, ($C_1$-$C_6$-alkyl)HN—($C_1$-$C_6$-alkyl)-NHC(O)—, ($C_1$-$C_6$-alkyl)$_2$N—($C_1$-$C_6$-alkyl)-NHC(O)—, heterocyclyl-($C_1$-$C_6$-alkyl)-NHC(O)—, trifluoromethyl and trifluoromethoxy,
- and the heterocyclyl-fragments of said substituents may in turn be at least monosubstituted with $C_1$-$C_3$-alkyl, $C_1$-$C_3$-alkoxy, fluoro, chloro, trifluoromethyl, trifluoromethoxy or —OH;

R⁴ is particularly preferred selected from the group consisting of:
- hydrogen, fluoro, chloro, 2-dimethylamino-ethoxy, 2-diethylamino-ethoxy, 3-dimethylamino-propoxy, 3-diethylamino-propoxy, dimethylamino-methyl, diethylamino-methyl, methoxy, ethoxy, piperidin-1-ylmethyl, 2-piperidin-1-yl-ethoxy, 4-methyl-piperazin-1-ylmethyl, morpholin-4-ylmethyl, 2-(4-methyl-piperazin-1-yl)-ethoxy, methyl, ethyl, trifluoromethyl and trifluoromethoxy;

R⁵ is preferably selected from the group consisting of:
- hydrogen, halogen, —CN, $R^{10}$, —$OR^8$, —C(O)$R^8$, —C(O)$OR^8$, —$NR^8H$, —$NR^8$($C_1$-$C_6$-alkyl), —C(O)$NR^8H$, —$SR^8$, —$SO_2NR^8H$, —$SO_2R^8$, aryl, heteroaryl, heterocyclyl, difluoromethyl, trifluoromethyl and trifluoromethoxy,
- and aryl, heterocyclyl and heteroaryl may in turn be at least monosubstituted with $C_1$-$C_6$-alkyl, $C_1$-$C_6$-alkoxy, oxo, halogen, trifluoromethyl, trifluoromethoxy or —OH;

R⁵ is more preferably selected from the group consisting of:
- hydrogen, fluoro, chloro, bromo, $R^{10}$, —$OR^8$, —C(O)$NR^8H$, trifluoromethyl and trifluoromethoxy, R⁵ is much more preferably selected from the group consisting of:
- hydrogen, fluoro, chloro, bromo, $C_1$-$C_6$-alkyl, heterocyclyl-($C_1$-$C_6$-alkyl)-, $H_2N$—($C_1$-$C_6$-alkyl)-, ($C_1$-$C_6$-alkyl)HN—($C_1$-$C_6$-alkyl)-, ($C_1$-$C_6$-alkyl)$_2$N—($C_1$-$C_6$-alkyl)-, —OH, $C_1$-$C_6$-alkoxy, heterocyclyl-($C_1$-$C_6$-alkyl)-O—, $H_2N$—($C_1$-$C_6$-alkyl)-O—, ($C_1$-$C_6$-alkyl)HN—($C_1$-$C_6$-alkyl)-O—, ($C_1$-$C_6$-alkyl)$_2$N—($C_1$-$C_6$-alkyl)-O—, —C(O)N($C_1$-$C_6$-alkyl)$_2$, —C(O)NH($C_1$-$C_6$-alkyl), $H_2N$—($C_1$-$C_6$-alkyl)-NHC(O)—, HO—($C_1$-$C_6$-alkyl)-NHC(O)—, ($C_1$-$C_6$-alkyl)HN—($C_1$-$C_6$-alkyl)-NHC(O)—, ($C_1$-$C_6$-alkyl)$_2$N—($C_1$-$C_6$-alkyl)-NHC(O)—, heterocyclyl-($C_1$-$C_6$-alkyl)-NHC(O)—, trifluoromethyl and trifluoromethoxy,
- and the heterocyclyl-fragments of said substituents may in turn be at least monosubstituted with $C_1$-$C_3$-alkyl, $C_1$-$C_3$-alkoxy, fluoro, chloro, trifluoromethyl, trifluoromethoxy or —OH;

R⁵ is particularly preferred selected from the group consisting of:
- hydrogen, fluoro, chloro, 2-dimethylamino-ethoxy, 2-diethylamino-ethoxy, 3-dimethylamino-propoxy, 3-diethylamino-propoxy, dimethylamino-methyl, diethylamino-methyl, methoxy, ethoxy, piperidin-1-ylmethyl, 2-piperidin-1-yl-ethoxy, 4-methyl-piperazin-1-ylmethyl, morpholin-4-ylmethyl, 2-(4-methyl-piperazin-1-yl)-ethoxy, methyl, ethyl, trifluoromethyl and trifluoromethoxy;

R⁶ is preferably selected from the group consisting of:
- hydrogen, halogen, —CN, $R^{10}$, —$OR^8$, —C(O)$R^8$, —C(O)$OR^8$, —$NR^8H$, —$NR^8$($C_1$-$C_6$-alkyl), —C(O)$NR^8H$, —$SR^8$, —$SO_2NR^8H$, —$SO_2R^8$, aryl, heteroaryl, heterocyclyl, difluoromethyl, trifluoromethyl and trifluoromethoxy,
- and aryl, heterocyclyl and heteroaryl may in turn be at least monosubstituted with $C_1$-$C_6$-alkyl, $C_1$-$C_6$-alkoxy, oxo, halogen, trifluoromethyl, trifluoromethoxy or —OH;

R⁶ is more preferably selected from the group consisting of:
- hydrogen, fluoro, chloro, bromo, $R^{10}$, —$OR^8$, —C(O)$NR^8H$, trifluoromethyl and trifluoromethoxy, R⁶ is much more preferably selected from the group consisting of:
- hydrogen, fluoro, chloro, bromo, $C_1$-$C_6$-alkyl, heterocyclyl-($C_1$-$C_6$-alkyl)-, $H_2N$—($C_1$-$C_6$-alkyl)-, ($C_1$-$C_6$-alkyl)HN—($C_1$-$C_6$-alkyl)-, ($C_1$-$C_6$-alkyl)$_2$N—($C_1$-$C_6$-alkyl)-, —OH, $C_1$-$C_6$-alkoxy, heterocyclyl-($C_1$-$C_6$-alkyl)-O—, $H_2N$—($C_1$-$C_6$-alkyl)-O—, ($C_1$-$C_6$-alkyl)HN—($C_1$-$C_6$-alkyl)-O—, ($C_1$-$C_6$-alkyl)$_2$N—($C_1$-$C_6$- alkyl)-O—, —C(O)N($C_1$-$C_6$-alkyl)$_2$, —C(O)NH($C_1$-$C_6$-alkyl), $H_2$N—($C_1$-$C_6$-alkyl)-NHC(O)—, HO—($C_1$-$C_6$-alkyl)-NHC(O)—, ($C_1$-$C_6$-alkyl)HN—($C_1$-$C_6$-alkyl)-NHC(O)—, ($C_1$-$C_6$-alkyl)$_2$N—($C_1$-$C_6$-alkyl)-NHC(O)—, heterocyclyl-($C_1$-$C_6$-alkyl)-NHC(O)—, trifluoromethyl and trifluoromethoxy, and the heterocyclyl-fragments of said substituents may in turn be at least monosubstituted with $C_1$-$C_3$-alkyl, $C_1$-$C_3$-alkoxy, fluoro, chloro, trifluoromethyl, trifluoromethoxy or —OH;

$R^6$ is particularly preferred selected from the group consisting of:

hydrogen, fluoro, chloro, 2-dimethylamino-ethoxy, 2-diethylamino-ethoxy, 3-dimethylamino-propoxy, 3-diethylamino-propoxy, dimethylamino-methyl, diethylamino-methyl, methoxy, ethoxy, piperidin-1-ylmethyl, 2-piperidin-1-yl-ethoxy, 4-methyl-piperazin-1-yl methyl, morpholin-4-ylmethyl, 2-(4-methyl-piperazin-1-yl)-ethoxy, methyl, ethyl, trifluoromethyl and trifluoromethoxy;

$R^6$ is exceptionally preferred hydrogen;

$R^7$ is preferably:

H;

or unsubstituted or at least monosubstituted $C_1$-$C_6$-alkyl, heterocyclyl, phenyl or heteroaryl, where the substituents are selected from the group consisting of: heteroaryl, heterocyclyl, phenyl, fluoro, chloro, —OH, $C_1$-$C_6$-alkyl, $C_1$-$C_6$-alkoxy, trifluoromethyl, trifluoromethoxy, —$NH_2$, —NH($C_1$-$C_6$-alkyl) and —N($C_1$-$C_6$-alkyl)$_2$, and heterocyclyl, phenyl and heteroaryl may in turn be at least monosubstituted with $C_1$-$C_3$-alkyl, $C_1$-$C_3$-alkoxy, oxo, trifluoromethyl, trifluoromethoxy, fluoro, chloro or —OH;

$R^7$ is more preferably:

unsubstituted or at least monosubstituted $C_1$-$C_6$-alkyl, where the substituents are selected from the group consisting of: heteroaryl, heterocyclyl, —OH, —$NH_2$, —NH($C_1$-$C_6$-alkyl) and —N($C_1$-$C_6$-alkyl)$_2$, and heterocyclyl and heteroaryl may in turn be at least monosubstituted with $C_1$-$C_3$-alkyl, $C_1$-$C_3$-alkoxy, trifluoromethyl, trifluoromethoxy, fluoro, chloro or —OH;

$R^7$ is particularly preferred:

unsubstituted or at least monosubstituted $C_1$-$C_4$-alkyl, where the substituents are selected from the group consisting of: morpholinyl, piperazinyl, piperidinyl, imidazolyl, pyrrolidinyl, —$NH_2$, —NH($C_1$-$C_6$-alkyl) and —N($C_1$-$C_6$-alkyl)$_2$, and morpholinyl, piperazinyl, piperidinyl, imidazolyl and pyrrolidinyl may in turn be monosubstituted with $C_1$-$C_3$-alkyl, $C_1$-$C_3$-alkoxy, trifluoromethyl, trifluoromethoxy, fluoro, chloro or —OH;

$R^8$ is preferably:

H;

or unsubstituted or at least monosubstituted $C_1$-$C_6$-alkyl, heterocyclyl, phenyl or heteroaryl, where the substituents are selected from the group consisting of: heteroaryl, heterocyclyl, phenyl, fluoro, chloro, —OH, $C_1$-$C_6$-alkyl, $C_1$-$C_6$-alkoxy, trifluoromethyl, trifluoromethoxy, —$NH_2$, —NH($C_1$-$C_6$-alkyl) and —N($C_1$-$C_6$-alkyl)$_2$, and heterocyclyl, phenyl and heteroaryl may in turn be at least monosubstituted with $C_1$-$C_3$-alkyl, $C_1$-$C_3$-alkoxy, oxo, trifluoromethyl, trifluoromethoxy, fluoro, chloro or —OH;

$R^8$ is more preferably:

unsubstituted or at least monosubstituted $C_1$-$C_6$-alkyl, where the substituents are selected from the group consisting of: heteroaryl, heterocyclyl, —OH, —$NH_2$, —NH($C_1$-$C_6$-alkyl) and —N($C_1$-$C_6$-alkyl)$_2$, and heterocyclyl and heteroaryl may in turn be at least monosubstituted with $C_1$-$C_3$-alkyl, $C_1$-$C_3$-alkoxy, trifluoromethyl, trifluoromethoxy, fluoro, chloro or —OH;

$R^8$ is particularly preferred:

unsubstituted or at least monosubstituted $C_1$-$C_4$-alkyl, where the substituents are selected from the group consisting of: morpholinyl, piperazinyl, piperidinyl, imidazolyl, pyrrolidinyl, —$NH_2$, —NH($C_1$-$C_6$-alkyl) and —N($C_1$-$C_6$-alkyl)$_2$, and morpholinyl, piperazinyl, piperidinyl, imidazolyl and pyrrolidinyl may in turn be monosubstituted with $C_1$-$C_3$-alkyl, $C_1$-$C_3$-alkoxy, trifluoromethyl, trifluoromethoxy, fluoro, chloro or —OH;

$R^9$ is preferably selected from the group consisting of:

hydrogen, halogen, —CN, $R^{10}$, —$OR^8$, —C(O)O—($C_1$-$C_6$-alkyl), —C(O)—($C_1$-$C_6$-alkyl), —$SR^8$, —C(O)$NR^8$H, aryl, heteroaryl, heterocyclyl, trifluoromethyl and trifluoromethoxy, and aryl, heterocyclyl and heteroaryl may in turn be at least monosubstituted with $C_1$-$C_6$-alkyl, $C_1$-$C_6$-alkoxy, oxo, halogen, trifluoromethyl, trifluoromethoxy or —OH;

$R^9$ is more preferably selected from the group consisting of:

hydrogen; halogen; —C(O)—($C_1$-$C_3$-alkyl); trifluoromethyl; trifluoromethoxy;

unsubstituted and at least monosubstituted $C_1$-$C_6$-alkyl and $C_2$-$C_6$-alkenyl, where the substituents are selected from the group consisting of: heteroaryl, heterocyclyl, phenyl, —OH, $C_1$-$C_6$-alkoxy, —$NH_2$, —NH($C_1$-$C_6$-alkyl) and —N($C_1$-$C_6$-alkyl)$_2$, and phenyl, heterocyclyl and heteroaryl may in turn be at least monosubstituted with $C_1$-$C_3$-alkyl, $C_1$-$C_3$-alkoxy, —CO—($C_1$-$C_3$-alkyl), fluoro, chloro, trifluoromethyl, trifluoromethoxy or —OH;

and heteroaryl and phenyl, which in turn may be at least monosubstituted with $C_1$-$C_6$-alkyl, $C_1$-$C_6$-alkoxy, halogen, trifluoromethyl, trifluoromethoxy or —OH $R^9$ is much more preferably selected from the group consisting of:

hydrogen; chloro; iodo; bromo; —C(O)—($C_1$-$C_3$-alkyl); unsubstituted and at least monosubstituted $C_1$-$C_4$-alkyl and $C_2$-$C_4$-alkenyl, where the substituents are selected from the group consisting of: phenyl azetidinyl, pyridinyl, morpholinyl, piperazinyl, piperidinyl, imidazolyl, pyrrolidinyl, —$NH_2$, —NH($C_1$-$C_6$-alkyl) and —N($C_1$-$C_6$-alkyl)$_2$, and phenyl, azetidinyl, pyridinyl, morpholinyl, piperazinyl, piperidinyl, imidazolyl and pyrrolidinyl may in turn be monosubstituted with $C_1$-$C_3$-alkyl, $C_1$-$C_3$-alkoxy, trifluoromethyl, trifluoromethoxy, fluoro, chloro or —OH;

and phenyl, imidazolyl and pyridinyl, which may in turn be at least monosubstituted with $C_1$-$C_6$-alkyl, $C_1$-$C_6$-alkoxy, halogen, trifluoromethyl, trifluoromethoxy or —OH $R^9$ is particularly preferred:

hydrogen, chloro, iodo, bromo, methyl, ethyl, vinyl, pyridinyl and phenyl;

$R^{10}$ is preferably:

unsubstituted or at least monosubstituted $C_1$-$C_6$-alkyl or $C_2$-$C_6$-alkenyl, where the substituents are selected from the group consisting of: phenyl, heteroaryl, heterocyclyl, —OH, —$NH_2$, —NH($C_1$-$C_6$-alkyl) and —N($C_1$-$C_6$-alkyl)$_2$, and phenyl, heterocyclyl and heteroaryl may in turn be at least monosubstituted with $C_1$-$C_3$-alkyl, $C_1$-$C_3$-alkoxy, —CO—($C_1$-$C_3$-alkyl), trifluoromethyl, trifluoromethoxy, fluoro, chloro or —OH;

$R^{10}$ is particularly preferred:

unsubstituted or at least monosubstituted $C_1$-$C_4$-alkyl or $C_2$-$C_4$-alkenyl, where the substituents are selected from the group consisting of: phenyl, azetidinyl, pyridinyl, pyrimidinyl, morpholinyl, piperazinyl, piperidinyl, imidazolyl, pyrrolidinyl, —$NH_2$, —$NH(C_1$-$C_3$-alkyl) and —$N(C_1$-$C_3$-alkyl)_2$, and phenyl, azetidinyl, pyridinyl, pyrimidinyl, morpholinyl, piperazinyl, piperidinyl, imidazolyl and pyrrolidinyl may in turn be monosubstituted with $C_1$-$C_3$-alkyl, $C_1$-$C_3$-alkoxy, trifluoromethyl, trifluoromethoxy, fluoro, chloro or —OH;

Heteroaryl is preferably imidazolyl, thienyl, furanyl, oxazolyl, isoxazolyl, pyridinyl, pyrimidinyl, pyrazolyl, benzo[b]thienyl, thiazolo[3,2-b][1,2,4]-triazolyl, pyrrolyl, quinolinyl, isoquinolinyl, 1,2,3,4-tetrahydroquinolinyl, benzoimidazolyl, indolyl or 1,3-benzodioxolyl; heteroaryl is particularly preferred pyridinyl, thienyl or pyrimidinyl;

Aryl is preferably naphthyl, indanyl or phenyl; aryl is particularly preferred phenyl.

Heterocyclyl is preferably azetidinyl, azepanyl, 4-oxoazepanyl, 1,4-diazepanyl, tetrahydrofuranyl, 1,3-dioxolanyl, morpholinyl, pyrrolidinyl, piperazinyl or piperidinyl; heterocyclyl is particularly preferred piperidinyl, morpholinyl or piperazinyl;

Examples for embodiments of preferred compounds of the formula (I) in reference to the above described definitions are:

i) $R^1$ to $R^{10}$, A, B, D, E, X heteroaryl, heterocyclyl and aryl have each its preferred meaning; or ii) $R^1$ has its preferred meaning and all other substituents have their basic meaning; or iii) $R^2$ has its particularly preferred meaning and all other substituents have their basic meaning; or iv) $R^3$ to $R^6$ have each its preferred meaning and all other substituents have their basic meaning; or v) $R^7$ and $R^8$ have each its preferred meaning and all other substituents have their basic meaning; or vi) $R^9$ has its preferred meaning and all other substituents have their basic meaning; or vii) $R^{10}$ has its preferred meaning and all other substituents have their basic meaning; or viii) A has its preferred meaning and all other substituents have their basic meaning; or ix) B has its preferred meaning and all other substituents have their basic meaning; or x) D has its preferred meaning and all other substituents have their basic meaning; or xi) E has its preferred meaning and all other substituents have their basic meaning; or xii) X has its preferred meaning and all other substituents have their basic meaning; or xiii) A, B, D and E have each its preferred meaning and all other substituents have their basic meaning; or xiv) A, B, D, E and X have each its preferred meaning and all other substituents have their basic meaning; or xv) Heteroaryl has its preferred meaning and all other substituents have their basic meaning; or xvi) Heterocyclyl has its preferred meaning and all other substituents have their basic meaning; or xvii) Aryl has its preferred meaning and all other substituents have their basic meaning; or xviii) $R^1$ to $R^{10}$, X heteroaryl, heterocyclyl and aryl have each its preferred meaning and A, B, D and E have their basic meaning, where only two of them may be N; or xix) $R^1$, $R^3$, $R^4$, $R^5$, $R^6$, $R^9$ and X have each its more preferred meaning, $R^7$, $R^8$, $R^{10}$, heteroaryl, heterocyclyl and aryl have each its preferred meaning, $R^2$ has its particularly preferred meaning and A, B, D and E have their basic meaning, where only one of them may be N; or xx) $R^1$, $R^3$, $R^4$, $R^5$, $R^6$ and $R^9$ have each its much more preferred meaning, heterocyclyl and heteroaryl have each its preferred meaning, $R^2$ and X have each its particularly preferred meaning and A, B, D and E have their basic meaning, where only one of them may be N; or xxi) $R^2$, $R^3$, $R^4$, $R^5$, $R^6$, $R^9$ and X have each its particularly preferred meaning, $R^1$ has its exceptionally preferred meaning and A, B, D and E have each its preferred meaning; or xxii) $R^2$, $R^4$, $R^5$, $R^9$ and X have each its particularly preferred meaning, $R^1$, $R^8$ and $R^6$ have each its exceptionally preferred meaning and A, B, D and E have each its preferred meaning; or xxiii) $R^2$, $R^3$, $R^4$, $R^5$, $R^6$, $R^9$ and X have each its particularly preferred meaning, $R^1$ has its exceptionally preferred meaning and A, B, D and E have their basic meaning, where only two of them may be N; or xxiv) $R^2$, $R^3$, $R^4$, $R^5$, $R^6$, $R^9$ and X have each its particularly preferred meaning, $R^1$ has its much more preferred meaning and A, B, D, E, heteroaryl and heterocyclyl have each its preferred meaning; or xxv) $R^2$, $R^9$ and X have each its particularly preferred meaning, $R^3$, $R^4$, $R^5$ and $R^6$ have each its much more preferred meaning, $R^1$ has its exceptionally preferred meaning and A, B, D, E, heteroaryl and heterocyclyl have each its preferred meaning; or xxvi) $R^2$, $R^3$, $R^4$, $R^5$, $R^6$ and X have each its particularly preferred meaning, $R^9$ has its much more preferred meaning, $R^1$ has its exceptionally preferred meaning and A, B, D, E, heteroaryl and heterocyclyl have each its preferred meaning; or xxvii) $R^2$, $R^3$, $R^4$, $R^5$, $R^6$, $R^8$ and $R^{10}$ have each its particularly preferred meaning, $R^9$ has its much more preferred meaning, X has its more preferred meaning, $R^1$ has its exceptionally preferred meaning and A, B, D, E, heteroaryl and heterocyclyl have each its preferred meaning; or xxviii) $R^1$ and $R^9$ have each its much more preferred meaning, $R^8$ and $R^6$ have each its exceptionally preferred meaning, $R^2$, $R^4$, $R^5$ and X have each its particularly preferred meaning and A, B, D, E, heterocyclyl and heteroaryl have each its preferred meaning; or xxix) $R^1$, $R^9$ and X have each its much more preferred meaning, $R^3$, $R^4$, $R^5$, $R^6$, aryl, heterocyclyl and heteroaryl have each its preferred meaning, $R^2$, $R^8$ and $R^{10}$ have each its particularly preferred meaning and A, B, D and E have their basic meaning, where only two of them may be N; or xxx) $R^3$, $R^4$, $R^5$, $R^6$ and $R^9$ have each its much more preferred meaning, heterocyclyl has its preferred meaning, $R^1$, $R^2$ and X have each its particularly preferred meaning and A, B, D and E have their basic meaning, where only one of them may be N; or xxxi) $R^1$, $R^3$, $R^4$, $R^5$, $R^6$ and $R^9$ have each its much more preferred meaning, aryl, heterocyclyl and heteroaryl have each its preferred meaning, $R^2$, $R^7$, $R^{10}$ and X have each its particularly preferred meaning and A, B, D and E have their basic meaning, where only one of them may be N; or xxxii) $R^1$, $R^3$, $R^4$, $R^5$, $R^6$, $R^7$, $R^8$, $R^9$ and X have each its more preferred meaning, $R^2$, $R^{10}$, heteroaryl, heterocyclyl and aryl have each its preferred meaning and A, B, D and E have their basic meaning, where only one of them may be N; or xxxiii) $R^1$ has its more preferred meaning, $R^9$ and X have each its much more preferred meaning, $R^7$, $R^8$, $R^{10}$, heteroaryl, heterocyclyl and aryl have each its preferred meaning, $R^3$ and $R^6$ have each its exceptionally preferred meaning, $R^2$, $R^4$ and $R^5$ have each its particularly preferred meaning and A, B, D and E have their basic meaning, where only one of them may be N; or xxxiv) $R^2$ to $R^{10}$, X heteroaryl, heterocyclyl and aryl have each its preferred meaning and $R^1$, A, B, D and E have their basic meaning, where only two of them may be N; or xxxv) $R^1$, $R^2$, $R^7$ to $R^{10}$, X heteroaryl, heterocyclyl and aryl have each its preferred meaning and $R^3$ to $R^6$, A, B, D and E have their basic meaning, where only two of them may be N; or As indicated before, the preferred compounds according to formula (I) are not limited to the above examples. Furthermore, all combinations of each substituent in its basic meaning with the preferred meanings, the more preferred meanings, the much more preferred meanings, the particularly preferred meanings or the exceptionally preferred meanings of the other substituents or all combinations of the preferred meanings, the more preferred meanings, the much more preferred meanings, the particularly preferred meanings or the exceptionally preferred meanings of the respective substituents, which are not exemplified above, are also a subject of the present invention. It is self-evident, that this is only the case, if the definitions of the respective substituents allow such a combination.

Most preferred compounds according to the general formula (I) are selected from the group consisting of:
4-(3-phenyl-1H-indol-2-yl)-6-pyridin-4-yl-2H-pyridazin-3-one, 4-(3-ethyl-1H-indol-2-yl)-6-pyridin-4-yl-2H-pyridazin-3-one, 4-(3-bromo-1H-indol-2-yl)-6-pyridin-4-yl-2H-pyridazin-3-one, 4-(5-isopropyl-1H-indol-2-yl)-6-pyridin-4-yl-2H-pyridazin-3-one, 4-[6-(2-diethylaminoethoxy)-1H-indol-2-yl]-6-pyridin-4-yl-2H-pyridazin-3-one, 4-(3-iodo-1H-indol-2-yl)-6-pyridin-4-yl-2H-pyridazin-3-one, 4-(3-chloro-1H-indol-2-yl)-6-pyridin-4-yl-2H-pyridazin-3-one, 6-pyridin-4-yl-4-(3-vinyl-1H-indol-2-yl)-2H-pyridazin-3-one, 4-[5-(3-dimethylaminopropoxy)-1H-indol-2-yl]-6-pyridin-4-yl-2H-pyridazin-3-one, 4-[6-(2-piperidin-1-yl-ethoxy)-1H-indol-2-yl]-6-pyridin-4-yl-2H-pyridazin-3-one, 4-(6-piperidin-1-ylmethyl-1H-indol-2-yl)-6-pyridin-4-yl-2H-pyridazin-3-one, 6-pyridin-4-yl-4-(1H-pyrrol-2-yl)-2H-pyridazin-3-one, 4-(6-dimethylaminomethyl-1H-indol-2-yl)-6-pyridin-4-yl-2H-pyridazin-3-one and 4-(6-diethylaminomethyl-1H-indol-2-yl)-6-pyridin-4-yl-2H-pyridazin-3-one.

Compounds of this invention may be prepared by known methods or in accordance with the reaction sequences described below. The starting materials used in the preparation of compounds of the invention are known or commercially available, or can be prepared by known methods or by specific reaction schemes described herein.

The below schemes illustrate some important routes for preparing compounds according to formula (I)

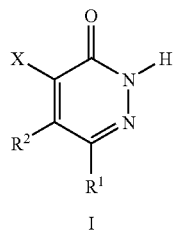

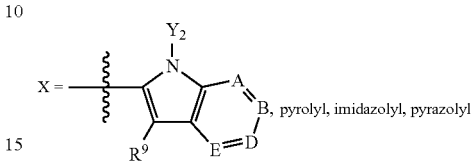

$Y_1$=Cl, Br or I
$Y_2$=H or a suitable protecting group, preferably tert-butoxycarbonyl (Boc)

Thus, for example a compound of the formula I is obtained from intermediates II by metal catalysed coupling and elimination of the methyl group.

M may be for example $B(OH)_2$, $B(OC_1\text{-}C_{10}\text{-alkyl})_2$, $Sn(C_1\text{-}C_{10}\text{-alkyl})_3$, $Zn(C_1\text{-}C_{10}\text{-alkyl})$. Intermediates II and M-X are either commercially available or are prepared by procedures known to a person skilled in the art.

In case $Y_2$ is a protecting group, said group is removed using methods known by a person skilled in the art.

Elimination of the methyl group in step b) from compounds of the formula III can be carried out using any suitable reagent known by a person skilled in the art.

Optionally A, B, D, E, $R^1$ and $R^9$ can be modified after the metal catalysed coupling. For example, if $R^1$=Cl, Br, I, it can be exchanged by palladium Suzuki or Stille coupling. (I. Parrot et al., Synthesis; 7, 1999; 1163-1168)

If $R^9$=H, it can be converted to Cl, Br or I by procedures know to a person skilled in the art. Furthermore, Cl, Br and I may in turn be exchanged with other substituents being defined for $R^9$ by standard metal catalysed procedures known to a person skilled in the art.

Through a different process according to scheme II, compounds of the formula I are obtained from intermediates IV and V by palladium catalysed indol synthesis and elimination of the methyl group in step b). (C. Chen, D. Lieberman, R. D. Larsen, T. R. Verhoeven, P. J. Reider, *J. Org. Chem.* 1997, 62, 2676-2677)

Scheme 2

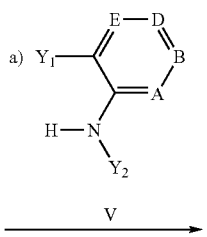

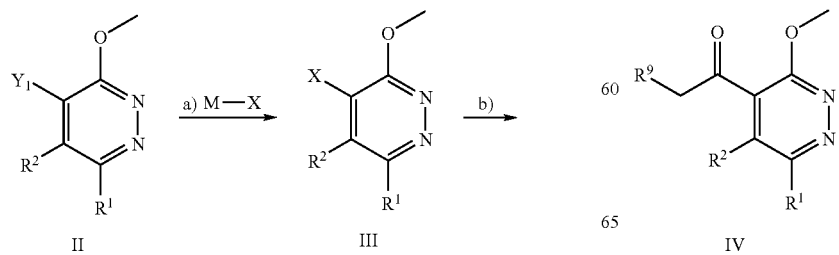

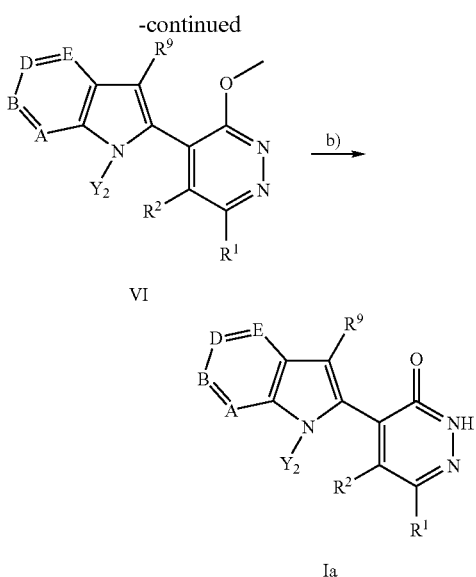

VI

Ia $Y_1$=Cl, Br or I
$Y_2$=H or a suitable protecting groups, preferably tert-butoxycarbonyl (Boc)

Optionally, A, B, D, E, $R^1$ and $R^9$ can be modified after the metal catalysed coupling. For example, if $R^1$=Cl, Br, I it can be exchanged by palladium Suzuki or Stille coupling.

If $R^9$=H, it can be converted to Cl, Br or I by procedures know to a person skilled in the art. Cl, Br and I may in turn be exchanged with other substituents being defined for $R^9$ by standard metal catalysed procedures known to a person skilled in the art.

Yet another process to compounds of the formula 1, where X is a substituted triazolyl and R has the same definition as $R^3$, is outlined in the following scheme 3.

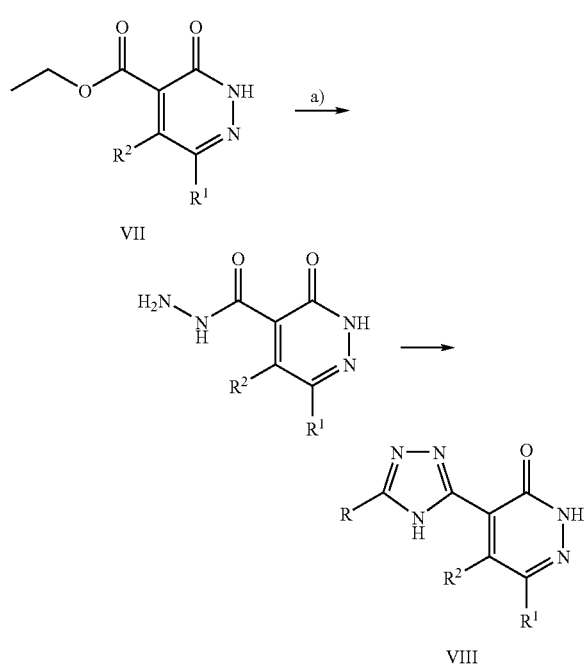

Compounds of the formula VIII can be obtained as outlined in the scheme from intermediates VII by procedures known to a person skilled in the art. In step a) compound VII is reacted with a suitable hydrazine, followed by conversion with a suitable acetimidic acid ester in step b) to obtain a compound of formula (VIII).

Intermediates VII are either commercially available or synthesized by procedures known to a person skilled in the art.

All reactions for the synthesis of the compounds of the formula (I) are per se well-known to the skilled person and can be carried out under standard conditions according to or analogously to procedures described in the literature, for example in Houben-Weyl, Methoden der Organischen Chemie (Methods of Organic Chemistry), Thieme-Verlag, Stuttgart, or Organic Reactions, John Wiley & Sons, New York. Depending on the circumstances of the individual case, in order to avoid side reactions during the synthesis of a compound of the formula (I), it can be necessary or advantageous to temporarily block functional groups by introducing protective groups and to deprotect them in a later stage of the synthesis, or introduce functional groups in the form of precursor groups which in a later reaction step are converted into the desired functional groups. Such synthesis strategies and protective groups and precursor groups which are suitable in an individual case are known to the skilled person. If desired, the compounds of the formula (I) can be purified by customary purification procedures, for example by recrystallization or chromatography. The starting compounds for the preparation of the compounds of the formula (I) are commercially available or can be prepared according to or analogously to literature procedures. The compounds obtained with the above-mentioned synthesis methods are a further object of the present invention.

Subject of the present invention is also the use of compounds according to the general formula (I) as pharmaceuticals or medicaments, respectively. With respect to the definition of the substituents X, $R^1$ and $R^2$ (as well as all further substituents defined by the before-mentioned substituents) the same explanations as laid out above in the context with the compounds as such apply.

Compounds of the formula (I) for use as pharmaceutical, in which one or more, including all, of the above-mentioned substituents have the preferred meanings, the more preferred meanings, the much more preferred meanings, the particularly preferred meanings or the exceptionally preferred meanings defined above, including all possible combinations, are also a subject of the present invention.

The compounds of general formula (I) are kinase inhibitors and can therefore be employed for the treatment of diseases, which may result from an abnormal activity of kinases. As abnormal kinase activity, there may be mentioned, for example, that of CDK2 and the like. In particular, compounds according to the present invention can be used for the inhibition of the kinase CDK2. Since CDK2 is usually part of a complex, such as CDK2/cyclin A or CDK2/cyclin E complexes, the compounds of the present invention can also used as inhibitors of CDK2/cyclin A or CDK2/cyclin E. This effect is particularly relevant for the treatment of neoplastic diseases such cancer.

Examples of diseases, which can be treated with the compounds according to the present invention, include: neoplastic diseases, preferably cancer, in particular a solid tumor or leukemia.

Within the present invention a solid tumor is defined as a tumor, which does not affect the hematopoietic or lymphatic system. An example of a solid tumor is an epithelial tumor. In the above-mentioned explanation the item treatment also includes prophylaxis, therapy or curing of the above-mentioned diseases.

All references to "compound(s) according to formula (I)" refer hereinbelow to a compound/compounds of the formula (I) as described above and also to their salts, solvates and physiologically functional derivatives as described herein.

The compounds of the formula (I) can be administered to animals, preferably to mammals, and in particular to humans. The compounds of the formula (I) can be administered as pharmaceuticals by themselves, in mixtures with one another or in mixtures with other pharmaceuticals or in the form of pharmaceutical preparations. Further subjects of the present invention therefore also are the use of the compounds of the formula (I) for preparing one or more medicaments for prophylaxis and/or treatment of the before-mentioned diseases, pharmaceutical preparations (or pharmaceutical compositions) comprising an effective dose of at least one compound of the formula (I) as well as pharmaceutical preparations comprising an effective dose of at least one compound of the formula (I) for prophylaxis and/or treatment of the before-mentioned diseases The amount of a compound according to formula (I) which is required in order to attain the desired biological effect depends on a number of factors, for example the specific compound selected, the intended use, the type of administration and the clinical state of the patient. In general, the daily dose is in the range from 0.3 mg to 100 mg (typically from 3 mg to 50 mg) per day per kilogram of body weight, for example 3-10 mg/kg/day. An intravenous dose can be, for example, in the range from 0.3 mg to 1.0 mg/kg and can be administered in a suitable manner as an infusion of 10 ng to 100 ng per kilogram per minute. Suitable infusion solutions for these purposes may contain, for example, from 0.1 ng to 10 mg, typically from 1 ng to 10 mg per milliliter. Individual doses may contain, for example, from 1 mg to 10 g of the active compound. Thus, ampoules for injections can contain, for example, from 1 mg to 100 mg, and orally administrable individual dose formulations such as, for example, tablets or capsules can contain, for example, from 1.0 to 1000 mg, typically from 10 to 600 mg. In the case of pharmaceutically acceptable salts, the above-mentioned masses relate to the mass of the free compound on which the salt is based. The compound used for the prophylaxis or therapy of the above-mentioned conditions may be the compounds according to formula (I) themselves, but they are preferably present in the form of a pharmaceutical composition together with an acceptable carrier. The carrier must be naturally acceptable, in the sense that it is compatible with the other ingredients of said composition and is not harmful to the patient's health. The carrier may be a solid or a liquid or both and is preferably formulated with the compound as an individual dose, for example as a tablet which may contain from 0.05% to 95% by weight of the active compound. Further pharmaceutically active substances may also be present, including further compounds according to formula (I). The pharmaceutical compositions of the invention may be prepared according to any of the known pharmaceutical methods which essentially comprise mixing the ingredients with pharmacologically acceptable carriers and/or excipients.

Besides at least one compound according to formula (I) as well as one or more carriers, the pharmaceutical preparations can also contain additives. As additives can be employed, for example: fillers, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The pharmaceutical compositions of the invention may be in form of a pill, tablet, lozenge, coated tablet, granule, capsule, hard or soft gelatin capsule, aqueous solution, alcoholic solution, oily solution, syrup, emulsion suspension pastille suppository, solution for injection or infusion, ointment, tincture, cream, lotion, powder, spray, transdermal therapeutic systems, nasal spray, aerosol mixture, microcapsule, implant, rod or plaster.

Pharmaceutical compositions of the invention are those which are suitable for oral, rectal, topical, peroral (e.g. sublingual) and parenteral (e.g. subcutaneous, intramuscular, intradermal or intravenous) administration, although the most suitable manner of administration depends in each individual case on the nature and severity of the condition to be treated and on the nature of the compound according to formula (I) used in each case. Sugar-coated formulations and sugar-coated delayed-release formulations, too, are included within the scope of the invention. Preference is given to acid-resistant and enteric formulations. Suitable enteric coatings include cellulose acetate phthalate, polyvinyl acetate phthalate, hydroxypropyl-methylcellulose phthalate and anionic polymers of methacrylic acid and methyl methacrylate.

Suitable pharmaceutical compounds for oral administration may be present in separate units as, for example, capsules, cachets, lozenges or tablets, which in each case contain a particular amount of the compound according to formula (I); as powders (gelatin capsules or cachets) or granules; as solution or suspension in an aqueous or nonaqueous liquid; or as an oil-in-water or water-in-oil emulsion. As already mentioned, said compositions can be prepared according to any suitable pharmaceutical method which includes a step in which the active compound and the carrier (which may comprise one or more additional components) are contacted. In general, the compositions are prepared by uniform and homogeneous mixing of the active compound with a liquid and/or finely dispersed solid carrier, after which the product is shaped, if necessary. Thus a tablet, for example, may be prepared by pressing or shaping a powder or granules of the compound, where appropriate with one or more additional components. Pressed tablets can be prepared by tableting the compound in free-flowing form, for example a powder or granules, mixed, where appropriate, with a binder, lubricant, inert diluent and/or one or more surface active/dispersing agents in a suitable machine. Shaped tablets can be prepared by shaping the pulverulent compound, moistened with an inert liquid diluent, in a suitable machine. As diluents can be used, for example, starch, cellulose, saccharose, lactose or silica. The pharmaceutical compositions of the invention may also comprise substances other than diluents, for example one or more lubricants such as magnesium stearate or talc, a coloring, a coating (sugar-coated tablets) or a varnish.

Pharmaceutical compositions which are suitable for peroral (sublingual) administration include lozenges which contain a compound according to formula (I) with a flavoring, usually sucrose and gum arabic or tragacanth, and pastilles which comprise the compound in an inert base such as gelatin and glycerol or sucrose and gum arabic.

Suitable pharmaceutical compositions for parenteral administration preferably comprise sterile aqueous preparations of a compound according to formula (I) which are preferably isotonic with the blood of the intended recipient. These preparations are preferably administered intravenously, although they may also be administered subcutaneously, intramuscularly or intradermally as an injection. Said preparations may preferably be prepared by mixing the compound with water and rendering the obtained solution sterile and isotonic with the blood. Injectable compositions of the invention generally contain from 0.1 to 5% by weight of the active compound.

These sterile compositions for parenteral administration may be preferably solutions which are aqueous or non aqueous, suspensions or emulsions. As solvent or vehicle, there may be used water, propylene glycol, polyethylene glycol, vegetable oils, in particular olive oil, organic esters for injection, for example ethyl oleate or other suitable organic solvents. These compositions may also contain adjuvants, in particular wetting, isotonizing, emulsifying, dispersing and stabilizing mediums. The sterilization may be carried out in several ways, for example by an aseptic filtration, by incorporating sterilizing agents into the composition, by irradiation or by heating. They may also be prepared in the form of sterile solid compositions which may be dissolved at the time of use in sterile water or in any other sterile medium for injection.

Suitable pharmaceutical compositions for rectal administration are preferably present as individual dose suppositories. These may be prepared by mixing a compound according to formula (I) with one or more conventional solid carriers, for example cocoa butter, and shaping the resulting mixture.

Suitable pharmaceutical compositions for topical application to the skin are preferably present as ointment, cream, lotion, paste, spray, aerosol or oil. Carriers which may be used are petroleum jelly, lanolin, polyethylene glycols, alcohols and combinations of two or more of these substances. In general, the active compound is present at a concentration of from 0.1 to 15%, for example from 0.5 to 2%, by weight of the composition.

Transdermal administration is also possible. Suitable pharmaceutical compositions for transdermal administration may be present as individual patches which are suitable for long-term close contact with the epidermis of the patient. Such patches suitably contain the active compound in an optionally buffered aqueous solution, dissolved and/or dispersed in an adhesive or dispersed in a polymer. A suitable active compound concentration is from approx. 1% to 35%, preferably approx. 3% to 15%. A particular possibility is the release of the active compound by electrotransport or iontophoresis, as described, for example, in Pharmaceutical Research, 2(6): 318 (1986).

The following examples illustrate compositions according to the invention:

EXAMPLE A

Gelatin capsules containing a dose of 50 mg of active product and having the following composition are prepared according to the usual technique:

| | |
|---|---|
| Compound of formula (I) | 50 mg |
| Cellulose | 18 mg |
| Lactose | 55 mg |
| Colloidal silica | 1 mg |
| Sodium carboxymethylstarch | 10 mg |
| Talc | 10 mg |
| Magnesium stearate | 1 mg |

EXAMPLE B

Tablets containing a dose of 50 mg of active product and having the following composition are prepared according to the usual technique:

| | |
|---|---|
| Compound of formula (I) | 50 mg |
| Lactose | 104 mg |
| Cellulose | 40 mg |
| Polyvidone | 10 mg |
| Sodium carboxymethylstarch | 22 mg |
| Talc | 10 mg |
| Magnesium stearate | 2 mg |
| Colloidal silica | 2 mg |

Mixture of hydroxymethylcellulose, glycerin, titanium oxide (72-3.5-24.5) qs 1 finished film-coated tablet of 245 mg

EXAMPLE C

A solution for injection containing 10 mg of active product and having the following composition is prepared:

| | |
|---|---|
| Compound of formula (I) | 10 mg |
| Benzoic acid | 80 mg |
| Benzyl alcohol | 0.06 ml |
| Sodium benzoate | 80 mg |
| Ethanol at 95% | 0.4 ml |
| Sodium hydroxide | 24 mg |
| Propylene glycol | 1.6 ml |
| Water | qs 4 ml |

Another subject of the present invention is the combination of compounds of the formula (I) with other pharmaceutically active substances not covered by formula (I).

The compounds of the present invention may be administered alone or mixed with other anticancer agents. Among the possible combinations, there may be mentioned:

alkylating agents and in particular cyclophosphamide, melphalan, ifosfamide, chlorambucil, busulfan, thiotepa, prednimustine, carmustine, lomustine, semustine, streptozotocin, decarbazine, temozolomide, procarbazine and hexamethylmelamine;

platinum derivatives such as in particular cisplatin, carboplatin or oxaliplatin;

antibiotic agents such as in particular bleomycin, mitomycin or dactinomycin;

antimicrotubule agents such as in particular vinblastine, vincristine, vindesine, vinorelbine or taxoids (paclitaxel and docetaxel);

anthracyclines such as in particular doxorubicin, daunorubicin, idarubicin, epirubicin, mitoxantrone or losoxantrone;

group I and II topoisomerases such as etoposide, teniposide, amsacrine, irinotecan, topotecan or tomudex;

fluoropyrimidines such as 5-fluorouracil, UFT or floxuridine;

cytidine analogues such as 5-azacytidine, cytarabine, gemcitabine, 6-mercaptomurine or 6-thioguanine;

adenosine analogues such as pentostatin, cytarabine or fludarabine phosphate;

methotrexate and folinic acid;

various enzymes and compounds such as L-asparaginase, hydroxyurea, trans-retinoic acid, suramine, dexrazoxane, amifostine, herceptin as well as oestrogenic and androgenic hormones.

It is also possible to combine a radiation treatment with the compounds of the present invention. This treatment may be administered simultaneously, separately or sequentially. The treatment will be adapted to the patient to be treated by the practitioner.

The following examples illustrate the invention without limitation.

EXAMPLE 1

4-(1H-Indol-2-yl)-6-pyridin-4-yl-2H-pyridazin-3-one

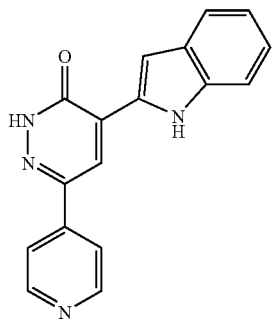

a) 6-Pyridin-4-yl-2H-pyridazin-3-one 99.5 g 4-Acetylpyridine is added to a cold (10° C.) solution of 222.4 potassium carbonate and 76.3 glyoxylic acid monohydrate in 1 L of water and the solution stirred at room temperature for 2.5 h. After cooling to 0° C., 325 ml of acetic acid are added followed by 58.8 ml hydrazine hydrate, and the resulting solution stirred under reflux for 1.5 h. The solution is then cooled to 0° C., the pH adjusted to 7 with solid $K_2CO_3$, the precipitate collected and washed with water and i-PrOH to give 89.27 g (64%) of 6-Pyridin-4-yl-2H-pyridazin-3-one.
MS: (M+1)=174 b) 3-Chloro-6-pyridin-4-yl-pyridazine 75.6 g 6-Pyridin-4-yl-2H-pyridazin-3-one is added in small portions to 234.5 g phosphorus oxychloride and the resulting mixture is stirred for 1 h at 100° C. Diluting into ice cold water, adjusting the pH 7 with aqueous sodium hydroxide and extraction with dichloromethane yielded 54 g 3-Chloro-6-pyridin-4-yl-pyridazine which is used without further purification.
MS: (M+1)=191 c) 3-Methoxy-6-pyridin-4-yl-pyridazine 63 ml of a 32% sodium methoxide solution in methanol are added to a solution of 57 g 3-Chloro-6-pyridin-4-yl-pyridazine in methanol, and the reaction mixture is stirred under reflux for 1.5 h. The solvent is removed under reduced pressure, the residue suspended in 0.7 L water and the pH adjusted to 7. Extraction with dichloromethane yielded 57 g 3-Methoxy-6-pyridin-4-yl-pyridazine, which is used without further purification.

d) 4-Iodo-3-methoxy-6-pyridin-4-yl-pyridazine 45 ml 1.6M solution of n-Butyllithium in hexane are added at −30° C. to a 10.2 g 2,2,6,6-tetramethylpiperidine in 100 ml THF, and the mixture is stirred at 0° C. for 30 min. After cooling to −75° C., 11.2 g 3-Methoxy-6-pyridin-4-yl-pyridazine dissolved 300 ml THF are added, and the solution is stirred at −75° C. for 35 min. The cold (−75° C.) reaction mixture is subsequently added to a cold (−75° C.) solution of 18.3 g iodine in 400 ml THF and stirred at −75° C. for 1.5 h. The reaction is quenched by adding 80 ml methanol/THF (1:1) at −75° C. and 300 ml saturated aqueous $NaHCO_3$ at room temperature and extracted with dichloromethane. The organic layer is washed with 5% aqueous $Na_2S_2O_3$ and saturated sodium chloride solution, dried ($MgSO_4$) and the solvent removed. The crude product is purified by chromatography on silica gel to yield 14.4 g of 4-Iodo-3-methoxy-6-pyridin-4-yl-pyridazine.
MS: (M+1)=313.95 e) 2-(3-Methoxy-6-pyridin-4-yl-pyridazin-4-yl)-indole-1-carboxylic acid tert-butyl ester Argon is passed for 30 min through a suspension of 55 mg 4-Iodo-3-methoxy-6-pyridin-4-yl-pyridazine, 55 mg 1-(tert-butoxycarbonyl)indole-2-boronic acid, 53.5 mg potassium carbonate, and 18.5 mg triphenylphosphine in 0.8 ml DME and 0.7 ml water. 4 mg palladium (II) acetate is added, and the mixture is stirred under reflux for 3 h. The product is isolated by extraction with ethyl acetate and purified by chromatography on silica gel yielding 27.5 mg 2-(3-Methoxy-6-pyridin-4-yl-pyridazin-4-yl)-indole-1-carboxylic acid tert-butyl ester.
MS: (M+1)=403.15 f) 4-(1H-Indol-2-yl)-6-pyridin-4-yl-2H-pyridazin-3-one 25 mg of 2-(3-Methoxy-6-pyridin-4-yl-pyridazin-4-yl)-indole-1-carboxylic acid tert-butyl ester, 7.4 mg trimethylchlorosilane and 11.3 mg KI dissolved in 1 ml of acetonitrile are stirred for 2 h at 60° C. Subsequently, 0.5 ml of a 4N solution of hydrochloric acid in dioxane is added and stirred for 2 h at room temperature. The solution is diluted into DMF/water and directly purified by HPLC on a RP18 column giving 4.5 mg 4-(1H-Indol-2-yl)-6-pyridin-4-yl-2H-pyridazin-3-one.
MS: (M+1)=289.

EXAMPLE 2

6-(4-Hydroxy-phenyl)-4-(1H-indol-2-yl)-2H-pyridazin-3-one

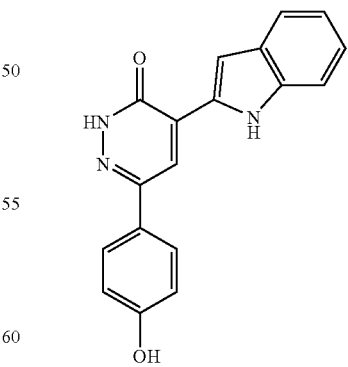

g) 6-Chloro-4-iodo-3-methoxy-pyridazine

6-Chloro-4-iodo-3-methoxy-pyridazine is synthesized following a procedure described in the literature (Mojovic, Ljubica; Turek, Alain; Ple, Nelly; Dorsy, Muriel; Ndzi, Bruno; Queguiner, Guy; Tetrahydron, 1995, 52, p 10417).

h) 2-(6-Chloro-3-methoxy-pyridazin-4-yl)-indole-1-carboxylic acid tert-butyl ester Argon is passed for 30 min through a suspension of 135 mg 6-Chloro-4-iodo-3-methoxy-pyridazine, 130.5 mg 1-(tert-butoxycarbonyl)indole-2-boronic acid, 152 mg potassium carbonate, and 52.5 mg triphenylphosphine in 2.2 ml DME and 1.1 ml water. 11.2 mg palladium (II) acetate is added, and the mixture is stirred under reflux for 3 h. The product is isolated by extraction with ethyl acetate and purified by chromatography on silica gel yielding 80 mg 2-(6-Chloro-3-methoxy-pyridazin-4-yl)-indole-1-carboxylic acid tert-butyl ester.

i) 2-[6-(4-Hydroxy-phenyl)-3-methoxy-pyridazin-4-yl]-indole-1-carboxylic acid tert-butyl ester Argon is passed for 30 min through a suspension of 70 mg 6-Chloro-4-iodo-3-methoxy-pyridazine, 53 mg 4-(4,4,5,5-Tetramethyl-1,3,2-dioxaborolan-2-yl)phenol, 59.4 mg potassium carbonate, and 20.1 mg triphenylphosphine in 0.8 ml DME and 0.7 ml water. 4.4 mg palladium (II) acetate is added, and the mixture is stirred under reflux for 3 h. The product is isolated by extraction with ethyl acetate and purified by chromatography on silica gel yielding 45.8 mg 2-[6-(4-Hydroxy-phenyl)-3-methoxy-pyridazin-4-yl]-indole-1-carboxylic acid tert-butyl ester.
MS: (M+1)=418 j) 6-(4-Hydroxy-phenyl)-4-(1H-indol-2-yl)-2H-pyridazin-3-one 25 mg of 2-[6-(4-Hydroxy-phenyl)-3-methoxy-pyridazin-4-yl]-indole-1-carboxylic acid tert-butyl ester, 8.6 mg trimethylchlorosilane and 13.5 mg KI dissolved in 1 ml of acetonitrile are stirred for 2 h at 60° C. Subsequently 0.75 ml of a 4N solution of hydrochloric acid in dioxane is added and stirred for 2 h at room temperature. The solvent is evaporated and the residue purified by HPLC on a RP18 column giving 14.4 mg 4-(1H-Indol-2-yl)-6-pyridin-4-yl-2H-pyridazin-3-one.
MS: (M+1)=304

EXAMPLE 3

4-(3-Methyl-1H-indol-2-yl)-6-pyridin-4-yl-2H-pyridazin-3-one

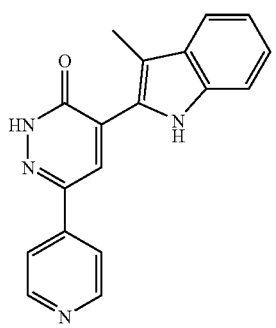

a) 3-Methyl-indole-1-carboxylic acid tert-butyl ester 1.88 g DMAP and 28.5 g di-tert-butyl dicarbonate are added to a solution of 10.3 g 3-methylindole in 300 ml dichloromethane and the solution is stirred for 4 h at room temperature. Evaporation of the solvent and purification of the crude product on silica gel gives 16.5 g 3-methyl-indole-1-carboxylic acid tert-butyl ester.
MS: (M+1)=232 b) 3-Methyl-2-(4,4,5,5-tetramethyl-[1,3,2]dioxaborolan-2-yl)-indole-1-carboxylic acid tert-butyl ester To a solution of 462 mg 3-Methyl-indole-1-carboxylic acid tert-butyl ester in 2.5 ml anhydrous tetrahydrofuran at −78° C. under argon is added 1.2 ml of a 2M LDA solution in THF/hexane and stirred at 0° C. for 30 min to complete the deprotonation. The reaction mixture is cooled to −78° C., 0.6 ml 2-Isopropoxy-4,4,5,5-tetramethyl-1,3,2-dioxaborolane are added, and stirred at 0° C. for 60 min. The reaction is quenched by the addition of 2 ml MeOH/water (1:1), diluted into water and extracted with ethylacetate. After evaporation of the solvent and purification on silica gel, 385 mg of 3-Methyl-2-(4,4,5,5-tetramethyl-[1,3,2]dioxaborolan-2-yl)-indole-1-carboxylic acid tert-butyl ester are obtained.
MS: (M+1)=358.6 c) 2-(3-Methoxy-6-pyridin-4-yl-pyridazin-4-yl)-3-methyl-indole-1-carboxylic acid tert-butyl ester Argon is passed for 30 min through a suspension of 333 mg 4-Iodo-3-methoxy-6-pyridin-4-yl-pyridazine, 380 mg 3-Methyl-2-(4,4,5,5-tetramethyl-[1,3,2]dioxaborolan-2-yl)-indole-1-carboxylic acid tert-butyl ester, 294 mg potassium carbonate, and 111.6 mg triphenylphosphine in 4.8 ml DME and 2.4 ml water. 24 mg palladium (II) acetate is added and the mixture stirred under reflux for 3 h. The product is isolated by extraction with ethyl acetate and purified by chromatography on silica gel yielding 52.1 mg 2-(3-Methoxy-6-pyridin-4-yl-pyridazin-4-yl)-3-methyl-indole-1-carboxylic acid tert-butyl ester.
MS: (M+1)=403.15 d) 4-(3-Methyl-1H-indol-2-yl)-6-pyridin-4-yl-2H-pyridazin-3-one 50 mg 2-(3-Methoxy-6-pyridin-4-yl-pyridazin-4-yl)-3-methyl-indole-1-carboxylic acid tert-butyl ester is dissolved in 0.75 ml ethanol and 0.75 ml 1N aqueous NaOH solution. The reaction mixture is stirred at 150° C. in microwave apparatus (200 W). The solution is neutralized by addition of 1N HCl, the solvent removed under reduced pressure and the crude product purified by HPLC chromatography (RP18 column, acetonitrile/water, 0.05% HCOOH) yielding 21.1 mg 4-(3-Methyl-1H-indol-2-yl)-6-pyridin-4-yl-2H-pyridazin-3-one.
MS: (M+1)=303

EXAMPLE 4

4-(6-Chloro-1H-indol-2-yl)-6-pyridin-4-yl-2H-pyridazin-3-one

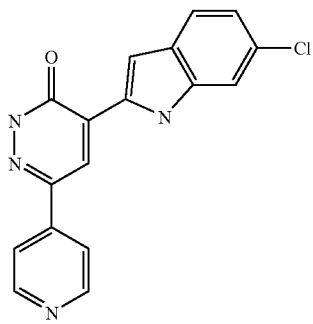

This compound is synthesized analogously to Example 3. MS: (M+1)=322

EXAMPLE 5

4-(5-Chloro-1H-indol-2-yl)-6-pyridin-4-yl-2H-pyridazin-3-one

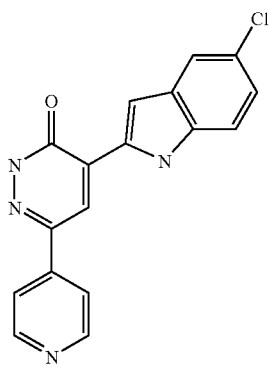

This compound is synthesized analogously to Example 3. MS: (M+1)=322

EXAMPLE 6

6-(4-Hydroxy-3,5-dimethyl-phenyl)-4-(1H-indol-2-yl)-2H-pyridazin-3-one

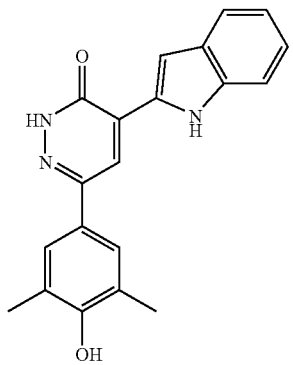

(a) 1-(6-Chloro-3-methoxy-pyridazin-4-yl)-ethanol 47.7 ml of a 1.6M solution of n-Butyl lithium in hexane is added dropwise at −75° C. to 100 ml tetrahydrofuran followed by 12.9 ml 2,2,6,6-tetramethylpiperidine and the resulting solution is allowed to warm to 0° C. and stirred for 30 min. The solution is cooled to −75° C. and a solution of 5 g 3-chloro-6-methoxypyridazine in 100 ml tetrahydrofuran is added at the same temperature. The reaction is stirred for 30 min at −75° C. A solution of 23.5 ml acetaldehyde in 50 ml tetrahydrofuran is cooled to −75° C. and added to the reaction. The solution is stirred at −75° C. for 90 min, then a mixture of 25 ml concentrated aqueous HCl, 100 ml ethanol and 125 ml tetrahydrofuran is added and the mixture is allowed to warm to room temperature. 60 ml of saturated aqueous sodium bicarbonate is slowly added, and the tetrahydrofuran is removed under reduced pressure. The resulting aqueous phase is extracted 3 times with dichloromethane. The organic phase is dried (MgSO$_4$), filtered and evaporated under reduced pressure. The product is purified by silica gel chromatography, eluting with a gradient of ethyl acetate in heptane. Yield 3.85 g. LC-MS (ES+) 189 (M+H)$^+$. NMR analysis indicates that the product contained approximately 15% of 1-(3-Chloro-6-methoxy-pyridazin-4-yl)-ethanol.

(b) 1-(6-Chloro-3-methoxy-pyridazin-4-yl)-ethanone 3.85 g 1-(6-Chloro-3-methoxy-pyridazin-4-yl)-ethanol is dissolved in 300 ml tetrahydrofuran and 35.5 g of manganese dioxide is added. The reaction is stirred for 48 h at RT. Solids are removed by filtration, and the solvent is removed under reduced pressure. The product is purified and separated from 1-(3-chloro-6-methoxy-pyridazin-4-yl)-ethanone by silica gel chromatography, eluting with a gradient of ethyl acetate in heptane. Yield 2.4 g. LC-MS (ES+) 187 (M+H)$^+$.

(c) 1-[6-(4-Hydroxy-3,5-dimethyl-phenyl)-3-methoxy-pyridazin-4-yl]-ethanone 250 mg of 1-(6-Chloro-3-methoxy-pyridazin-4-yl)-ethanone and 232 mg of tetrakis(triphenylphosphine) palladium (0) are dissolved in 5 ml DME and the solution is stirred for 5 min at RT under argon. 400 mg of 2,6-Dimethyl-4-(4,4,5,5-tetramethyl-[1,3,2]dioxaborolan-2-yl)-phenol and 1.4 ml of a 2M aqueous solution of sodium carbonate are added and the reaction solution is stirred at 95° C. for 4 h. The reaction solution is filtered through a silica gel cartridge, eluting with dichloromethane. The solvent is removed under reduced pressure. The product is purified by silica gel chromatography, eluting with a gradient of ethyl acetate in heptane. Yield 334 mg. LC-MS (ES+) 273 (M+H)$^+$.

(d) 4-[5-(1H-Indol-2-yl)-6-methoxy-pyridazin-3-yl]-2,6-dimethyl-phenol 205 mg of 2-bromoaniline and 72 mg of anhydrous magnesium sulfate are suspended in 7 ml dimethylacetamide. 325 mg of 1-[6-(4-Hydroxy-3,5-dimethyl-phenyl)-3-methoxy-pyridazin-4-yl]-ethanone and 86.6 µl acetic acid are added and the reaction is degassed with argon. 330 mg of tripotassium phosphate and 61 mg of bis(tri-tert-butylphosphine) palladium (0) are added and the reaction is degassed with argon. The reaction is heated to 140° C. for 5 h. The solution is poured into water and extracted with ethyl acetate. The solvent is removed under reduced pressure. The product is purified by silica gel chromatography, eluting with a gradient of ethyl acetate in heptane. Yield 105 mg. LC-MS (ES+) 346 (M+H)$^+$.

(e) 6-(4-Hydroxy-3,5-dimethyl-phenyl)-4-(1H-indol-2-yl)-2H-pyridazin-3-one 100 mg of 4-[5-(1H-Indol-2-yl)-6-methoxy-pyridazin-3-yl]-2,6-dimethyl-phenol is suspended in 2 ml acetonitrile and 40 μl of trimethylsilyl chloride and 53 mg of potassium iodide are added. The solution is heated to 80° C. for 3 h, then a further 120 μl of trimethylsilyl chloride and 159 mg of potassium iodide are added. The solution is heated to 80° C. for 3 h then stirred at RT for 16 h. The reaction solution is diluted with water and the product is purified by preparative RP-HPLC eluting with a gradient of 0-100% acetonitrile in water (+0.01% trifluoroacetic acid).

Yield 15 mg. LC-MS (ES+) 332 (M+H)+.

EXAMPLE 7

6-(4-Hydroxy-3,5-dimethyl-phenyl)-4-(5-trifluoromethyl-1H-indol-2-yl)-2H-pyridazin-3-one

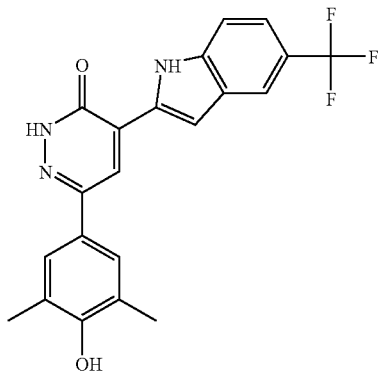

This compound is synthesized analogously to Example 6, whereby the 2-bromoaniline in step (d) is replaced by 2-bromo-4-trifluoromethyl-phenylamine. Yield 3.9 mg. LC-MS (ES+) 400 (M+H)+.

EXAMPLE 8

4-(4-Methyl-1H-indol-2-yl)-6-pyridin-4-yl-2H-pyridazin-3-one

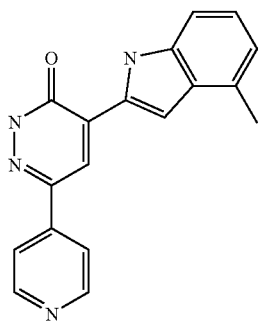

This compound is synthesized analogously to Example 3.
MS: (M+1)=303

EXAMPLE 9

4-(3-Phenyl-1H-indol-2-yl)-6-pyridin-4-yl-2H-pyridazin-3-one

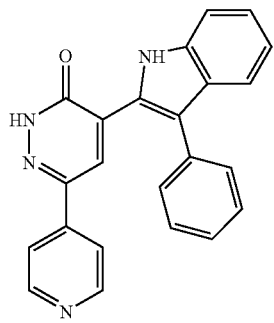

a) 2-(3-Methoxy-6-pyridin-4-yl-pyridazin-4-yl)-1H-indole trifluoroacetate

A solution of 5.5 g 2-(3-Methoxy-6-pyridin-4-yl-pyridazin-4-yl)-indole-1-carboxylic acid tert-butyl ester and 5 ml TFA in 10 ml dichloromethane stirred for 18 h at room temperature. The solvent is evaporated and the crude product purified by suspensing in water and collecting the precipitate.
Yield 5.4 g LC-MS (ES+) 303 (M+H)+.

b) 3-Iodo-2-(3-methoxy-6-pyridin-4-yl-pyridazin-4-yl)-1H-indole TFA salt c)

A suspension of 2 g 2-(3-Methoxy-6-pyridin-4-yl-pyridazin-4-yl)-1H-indole trifluoroacetate and 1.3 g N-Iodosuccinimide (NIS) in acetone is stirred for 4 h at ambient temperature. The product is isolated by filtration, washed with acetone and used without further purification.
Yield 2.2 g LC-MS (ES+) 429 (M+H)+.

d) 2-(3-Methoxy-6-pyridin-4-yl-pyridazin-4-yl)-3-phenyl-1H-indole

Argon is passed for 30 min through a suspension of 270 mg 3-Iodo-2-(3-methoxy-6-pyridin-4-yl-pyridazin-4-yl)-1H-indole TFA salt, 73 mg phenylboronic acid, 220 mg potassium carbonate and 52.4 mg triphenylphosphine in 2 ml DME and 1 ml water. 11.2 mg palladium (II) acetate is added and the mixture stirred under reflux for 5 h. The product is isolated by extraction with ethyl acetate and purified by chromatography on silica gel.
Yield 64 mg LC-MS (ES+) 379 (M+H)+.

e) 4-(3-Phenyl-1H-indol-2-yl)-6-pyridin-4-yl-2H-pyridazin-3-one 63 mg 2-(3-Methoxy-6-pyridin-4-yl-pyridazin-4-yl)-3-phenyl-1H-indole is dissolved in 0.75 ml ethanol and 0.75 ml 1N aqueous NaOH solution. The reaction mixture is stirred at 150° C. in microwave apparatus (200 W). The reaction mixture is directly applied to HPLC chromatography to isolate the product (RP18 column, acetonitrile/water, 0.05% HCOOH)
Yield 42 mg LC-MS (ES+) 365 (M+H)+.

EXAMPLE 10

4-(3-Ethyl-1H-indol-2-yl)-6-pyridin-4-yl-2H-pyridazin-3-one

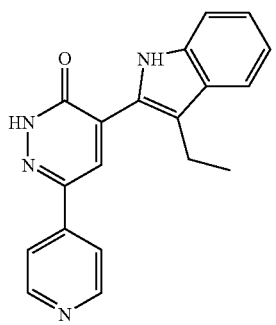

a) 2-(3-Methoxy-6-pyridin-4-yl-pyridazin-4-yl)-3-vinyl-1H-indole

A mixture of 430 mg 3-Iodo-2-(3-methoxy-6-pyridin-4-yl-pyridazin-4-yl)-1H-indole, 490 mg tributyl(vinyl)tin, 165 mg tetraethylammonium-chloride and 35 mg bis(triphenylphosphine)palladium(II) chloride in DMF is stirred at 80° C. for 40 min. After cooling to room temperature, 15 ml aqueous potassium fluoride solution (30%) are added, and the mixture is stirred for 30 min at room temperature before extraction with EtOAc. The organic layer is dried over MgSO$_4$ and the solvent evaporated prior to purification of the crude product by preparative RP-HPLC eluting with a gradient of 0-100% acetonitrile in water (+0.01% HCOOH).

Yield 233 mg. LC-MS (ES+) 329 (M+H)$^+$.

b) 3-Ethyl-2-(3-methoxy-6-pyridin-4-yl-pyridazin-4-yl)-1H-indole 12 mg Palladium, 10% on charcoal are added to a solution of 70 mg 2-(3-Methoxy-6-pyridin-4-yl-pyridazin-4-yl)-3-vinyl-1H-indole methanol, and the reaction mixture is stirred under an hydrogen atmosphere for 4 hours. The catalyst is removed by filtration and the solvent by evaporation yielding the product which was used without further purification.

Yield 61 mg. LC-MS (ES+) 331 (M+H)$^+$.

c) 4-(3-Ethyl-1H-indol-2-yl)-6-pyridin-4-yl-2H-pyridazin-3-one 60 mg 3-Ethyl-2-(3-methoxy-6-pyridin-4-yl-pyridazin-4-yl)-1H-indole is dissolved in 0.5 ml ethanol and 0.5 ml 1N aqueous NaOH solution. The reaction mixture is stirred at 150° C. in microwave apparatus (200 W). The reaction mixture is directly applied to HPLC chromatography to isolate the product (RP18 column, acetonitrile/water, 0.05% HCOOH)

Yield 19 mg. LC-MS (ES+) 317 (M+H)$^+$.

EXAMPLE 11

4-(3-Morpholin-4-ylmethyl-1H-indol-2-yl)-6-pyridin-4-yl-2H-pyridazin-3-one

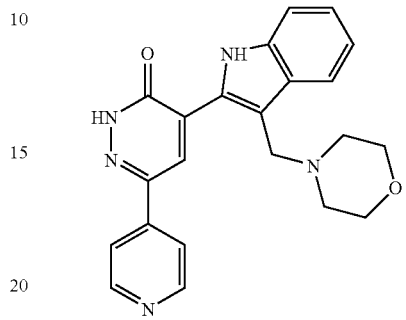

A solution of 14 ul formaldehyde (37% solution in water) and 17 ul morpholine in 0.5 ml glacial acetic acid is added dropwise at 0° C. to 50 mg 4-(1H-Indol-2-yl)-6-pyridin-4-yl-2H-pyridazin-3-one suspended in 2.24 ml glacial acetic acid and 2.6 ml 1,4-Dioxane. The resulting mixture is stirred for 3 h at room temperature, subsequently poured into ice/water and the pH is adjusted to 13.3 with 2N Sodium Hydroxide. The product is isolated by filtration.

Yield 15.4 mg. LC-MS (ES+) 388 (M+H)+.

The compounds 38-42 are synthesized analogously to example 11.

EXAMPLE 12

4-(3-Bromo-1H-indol-2-yl)-6-pyridin-4-yl-2H-pyridazin-3-one

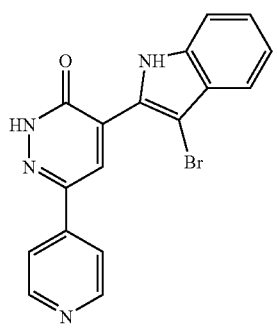

22 mg 4-(1H-Indol-2-yl)-6-pyridin-4-yl-2H-pyridazin-3-one is suspended in 30 mL acetone and 2 mg N-bromosuccinimide is added. The reaction mixture is stirred for 3 hours at room temperature, the precipitated product isolated by filtration and washed with acetone. The product is purified by preparative RP-HPLC eluting with a gradient of 0-100% acetonitrile in water (0.05% HCOOH). Yield 11.2 mg. LC-MS (ES+) 368 (M+H)$^+$.

EXAMPLE 13

4-(5-Isopropyl-1H-indol-2-yl)-6-pyridin-4-yl-2H-pyridazin-3-one

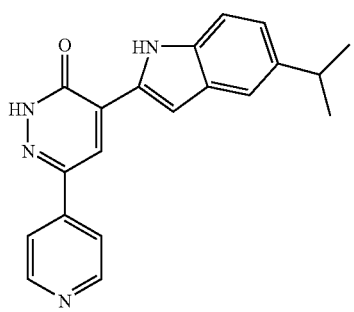

a) 1-(3-Methoxy-6-pyridin-4-yl-pyridazin-4-yl)-ethanol

To a solution of 0.93 g 2,2,6,6-tetramethylpiperidine in 30 ml THF is added 4.13 ml (15% solution in toluene) n-butyllithium at −30° C. After being stirred at 0° C. for 30 min, the reaction mixture is cooled to −78° C. and a solution of 1.12 g 3-methoxy-6-pyridin-4-yl-pyridazine in 30 ml THF is added and stirred at −78° C. for 30 min. At this temperature, 3.17 g acetaldehyde are added and stirred for another 2 h. The reaction is quenched by the addition of 24 ml MeOH/THF 1:1 and warmed to ambient temperature. Then, 30 ml saturated aq. NaHCO$_3$ are added and extracted with CH$_2$Cl$_2$. The combined organic layers are washed with water, dried over MgSO$_4$ and concentrated in vacuo. The residue is purified by flash chromatography (ethyl acetate 100%) to give 0.91 g (66%) of the desired product as a beige solid.
MS: (M+1)=232 b) 1-(3-Methoxy-6-pyridin-4-yl-pyridazin-4-yl)-ethanone

To a solution of 0.91 g 1-(3-methoxy-6-pyridin-4-yl-pyridazin-4-yl)-ethanol in 10 ml CH$_2$Cl$_2$ is added a suspension of 1.70 g Dess-Martin Periodane in 10 ml CH$_2$Cl$_2$ at room temperature. After being stirred for 3 h, the suspension is extracted with 5% aq. Na$_2$S$_2$O$_3$ solution. The organic layer is washed with water, dried over MgSO$_4$ and concentrated in vacuo. The residue is purified by chromatography to give 0.83 g (92%) of the desired product as a yellow solid.
MS: (M+1)=230 c) 5-Isopropyl-2-(3-methoxy-6-pyridin-4-yl-pyridazin-4-yl)-1H-indole

To a solution of 100 mg 1-(3-methoxy-6-pyridin-4-yl-pyridazin-4-yl)-ethanone, 120 mg K$_3$PO$_4$, 26.3 mg MgSO$_4$ and 22.3 mg palladium(0)-bis(tri-tert-butyl-phosphine) in 0.5 ml dry and degassed DMA are added 37 μl acetic acid and 93 mg 2-bromo-4-isopropylaniline at room temperature. The mixture is stirred at 140° C. for 36 h. The reaction is cooled to room temperature, diluted with ethyl acetate, washed with water, dried over MgSO$_4$ and concentrated in vacuo (3 h high-vacuum). The residue (139 mg) was used without purification for the next step.
MS: (M+1)=345 d) 4-(5-Isopropyl-1H-indol-2-yl)-6-pyridin-4-yl-2H-pyridazin-3-one

To a solution of 139 mg (crude material) 5-isopropyl-2-(3-methoxy-6-pyridin-4-yl-pyridazin-4-yl)-1H-indole in 2.5 ml EtOH is added 2.5 ml aq. NaOH (1 M). The mixture is heated for 10 min at 150° C. using microwave. After cooling to room temperature the mixture is filtered and purified by HPLC to give 14 mg (11%) of the desired product as yellow solid.
MS: (M+1)=331

The following compounds 14 to 16 are synthesized using the same procedures.

EXAMPLE 14

4-(5-Methyl-1H-indol-2-yl)-6-pyridin-4-yl-2H-pyridazin-3-one

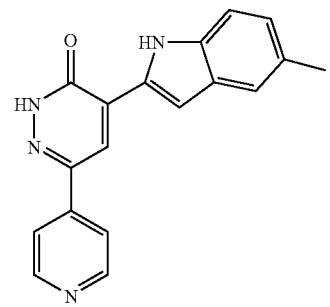

MS: (M+1)=303

EXAMPLE 15

4-(5-Fluoro-1H-indol-2-yl)-6-pyridin-4-yl-2H-pyridazin-3-one

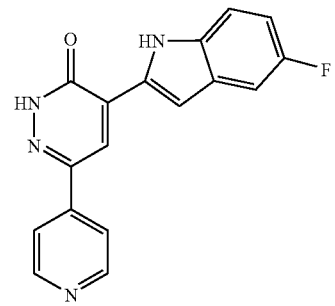

MS: (M+1)=307

EXAMPLE 16

6-Pyridin-4-yl-4-(5-trifluoromethoxy-1H-indol-2-yl)-2H-pyridazin-3-one

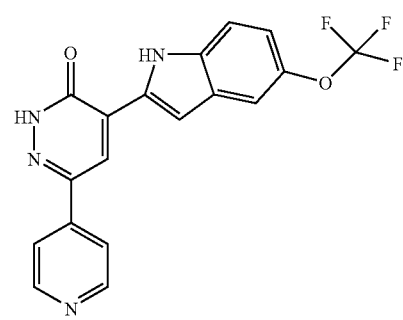

MS: (M+1)=373

EXAMPLE 17

6-Pyridin-4-yl-4-[3-((E)-styryl)-1H-indol-2-yl]-2H-pyridazin-3-one

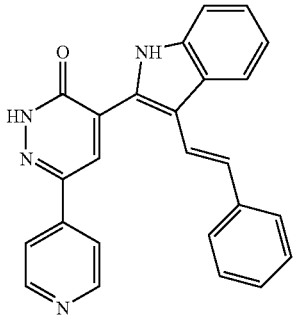

MS: (M+1)=391

This compound is synthesized analogously to example 9.

EXAMPLE 18

4-(3-Acetyl-1H-indol-2-yl)-6-pyridin-4-yl-2H-pyridazin-3-one

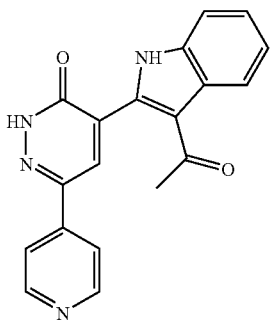

4 mg acetyl chloride are added at 0° C. to a suspension of 80 mg aluminum chloride 1,2-Dichloroethane, followed by 208 mg 2-(3-Methoxy-6-pyridin-4-yl-pyridazin-4-yl)-1H-indole Trifluoroacetate. The reaction mixture is stirred for 4 h at room temperature and for 3 h at 50° C. It is worked up pouring into an ice/water mixture and filtering. The layers are separated, the organic layer is washed with water, dried over $MgSO_4$ and the solvent removed. Reverse phase HPLC chromatography yielded 8.1 mg 4-(3-Acetyl-1H-indol-2-yl)-6-pyridin-4-yl-2H-pyridazin-3-one.

MS: (M+1)=331

EXAMPLE 19

4-[1H-Indol-6-(2-dimethylaminoethoxy)-2-yl]-6-pyridin-4-yl-2H-pyridazin-3-one

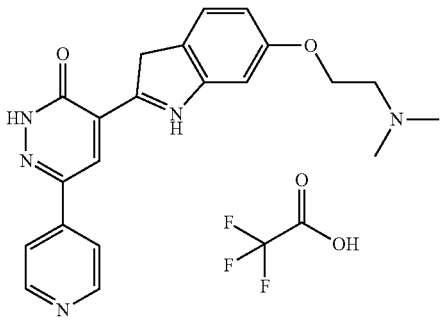

a) 1-(tert-Butoxycarbonyl)-6-(tert-butyldimethylsiloxy)indole

A mixture of 5.5 g 6-hydroxyindole, 7.47 g tert-butyldimethylsilyl chloride, 7.03 g imidazole, and 25 mL dimethylformamide is stirred at ambient temperature for 20 h. The reaction is diluted with ethyl acetate, washed with water (2×), dried ($MgSO_4$), and the solvent removed under reduced pressure to provide an oil. The oil is chromatographed, eluting with ethyl acetate/heptane, to afford 9.05 g (88%) of 6-(tert-butyldimethylsiloxy)-1H-indole as a white solid: TLC $R_f$ 0.4 (silica, 1:9 ethyl acetate/heptane).

To a solution of 9 g 6-(tert-butyldimethylsiloxy)-1H-indole in 90 mL dichloromethane is added 0.89 g 4-(dimethylamino)pyridine and 12.7 g di-tert-butyl dicarbonate and the reaction stirred at ambient temperature for 4 h. The solvent is removed to give an oil. The oil is chromatographed on silica, eluting with 5:95 ethyl acetate/heptane, to provide 11.5 g (91%) of 1-(tert-butoxycarbonyl)-6-(tert-butyldimethylsiloxy)indole as a slightly yellow oil.

MS: (M+1)=348.20.

b) 1-(tert-Butoxycarbonyl)-6-(tert-butyldimethylsiloxy)indole-2-boronic acid

To a solution of 1 g 1-(tert-butoxycarbonyl)-6-(tert-butyldimethylsiloxy)indole in 15 mL anhydrous tetrahydrofuran at −78° C. under nitrogen is added tert-butyllithium (2.30 mL of a 1.5 M solution in pentane) over 3 min, and the reaction is stirred at −78° C. After 32 min, 0.66 mL trimethylborate are added in one portion, and the reaction is stirred at 0° C. After 2 h, 9 mL saturated aqueous ammonium chloride are added, the mixture diluted with 25 mL ether, and stirred at ambient temperature. The reaction is acidified with 4 mL of a solution made from 10% aqueous $KHSO_4$ (60 mL) and concentrated $H_2SO_4$ (2 mL). After stirring for 15 min, the layers are separated and the organics are washed with water (15 mL) and brine (15 mL) successively, dried ($Na_2SO_4$), and the solvent is removed under reduced pressure to yield a partially solidified material. The material is washed with hot hexanes (5 mL) and filtered. The collected solid is washed with hexanes (2×5 mL) to give 635 mg (56%) of 1-(tert-butoxycarbonyl)-6-(tert-butyldimethylsiloxy)indole-2-boronic acid as a white powder.

MS: M=392.20.

c) 6-Hydroxy-2-(3-methoxy-6-pyridin-4-yl-pyridazin-4-yl)-indole-1-carboxylic acid tert-butyl ester 600 mg 4-iodo-3-methoxy-6-pyridin-4-yl-pyridazine, 974 mg 1-(tert-butoxycarbonyl)-6-(tert-butyldimethylsiloxy)indole-2-boronic acid, 2.5 g cesium carbonate, and 78 mg [1,1'-bis(diphenylphosphino)ferrocene]dichloropalladium(II) complex with dichloromethane (1:1) are dissolved in a mixture of 18 mL dioxane and 5.4 mL water. Argon is bubbled through the solution for 5 minutes. The mixtures is heated to reflux for 2 hours. After diluting with EtOAc, the organic phase is washed with water and brine, dried with $MgSO_4$ and concentrated in vacuo.

The crude product is dissolved in 30 mL THF. After addition of 1.51 g tetrabutylammonium fluoride trihydrate, the red solution is stirred for 2 hours. The reaction mixture is diluted with EtOAc, washed with saturated aqueous ammonium chloride, water, and brine, dried with $MgSO_4$ and concentrated in vacuo. Purification by HPLC afforded 760 mg (95%) 6-Hydroxy-2-(3-methoxy-6-pyridin-4-yl-pyridazin-4-yl)-indole-1-carboxylic acid tert-butyl ester.

MS: (M+1)=419.21 d) 6-(2-Dimethylaminoethoxy)-2-(3-methoxy-6-pyridin-4-yl-pyridazin-4-yl)-indole-1-carboxylic acid tert-butyl ester 100 mg 6-hydroxy-2-(3-methoxy-6-pyridin-4-yl-pyridazin-4-yl)-indole-1-carboxylic acid tert-butyl ester and 175 mg triphenylphosphine are dissolved in 7 mL toluene and 2 mL THF. After dropwise addition of 84 µL 2-dimethylaminoethanol and 123 µL diethyl azodicarboxylate, the reaction mixture is stirred at room temperature for 5 hours. The solvent is removed in vacuo and the residue is dissolved in dichloromethane. The organic phase is washed with water and the aqueous phase is extracted twice with dichloromethane. The combined organic phases are dried over MgSO$_4$ and concentrated in vacuo. Purification by HPLC afforded 35 mg (43%) 6-(2-dimethylaminoethoxy)-2-(3-methoxy-6-pyridin-4-yl-pyridazin-4-yl)-indole-1-carboxylic acid tert-butyl ester.

MS: (M+1)=490.31 e) 4-[1H-Indol-6-(2-dimethylaminoethoxy)-2-yl]-6-pyridin-4-yl-2H-pyridazin-3-one 32 mg 6-(2-dimethylaminoethoxy)-2-(3-methoxy-6-pyridin-4-yl-pyridazin-4-yl)-indole-1-carboxylic acid tert-butyl ester is dissolved in 0.5 ml ethanol. 0.5 ml 1 N aqueous sodium hydroxide are added. The reaction mixture is heated to 150° C. in a microwave oven for 30 minutes. Purification by HPLC afforded 9 mg (28%) 4-[1H-indol-6-(2-dimethylaminoethoxy)-2-yl]-6-pyridin-4-yl-2H-pyridazin-3-one as its trifluoroacetate salt.

MS: (M+1)=376.29

The following examples 20-23, 28-33, 44, 45, 49, 52 and 55 are synthesized analogously to example 19.

EXAMPLE 20

4-[6-(2-Diethylamino-ethoxy)-1H-indol-2-yl]-6-pyridin-4-yl-2H-pyridazin-3-one

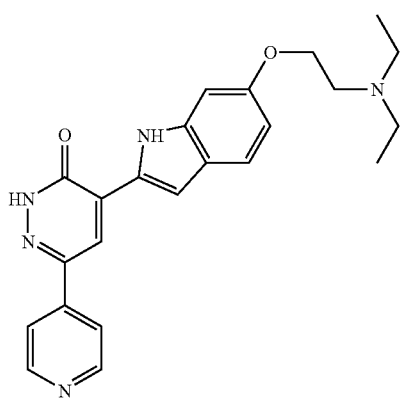

MS: (M+1)=404

EXAMPLE 21

4-[6-(3-Diethylamino-propoxy)-1H-indol-2-yl]-6-pyridin-4-yl-2H-pyridazin-3-one

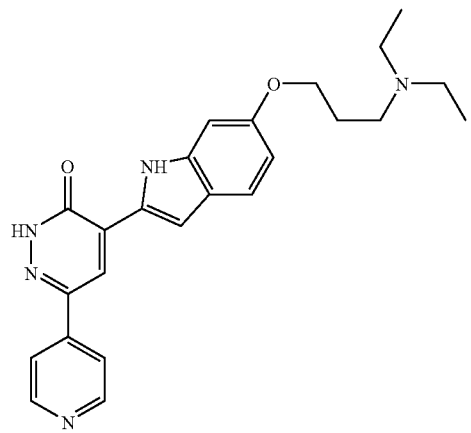

MS: (M+1)=419

EXAMPLE 22

4-[6-(3-Dimethylamino-propoxy)-1H-indol-2-yl]-6-pyridin-4-yl-2H-pyridazin-3-one

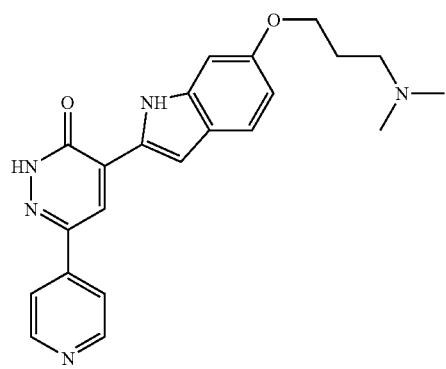

MS: (M+1)=390

EXAMPLE 23

4-(6-Benzyloxy-1H-indol-2-yl)-6-pyridin-4-yl-2H-pyridazin-3-one

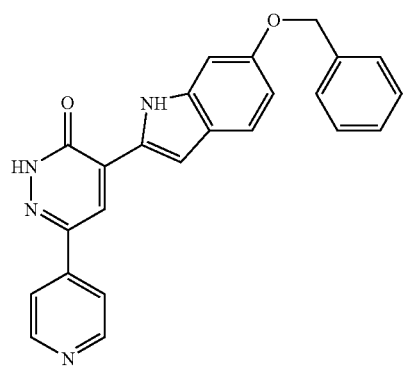

MS: (M+1)=395

EXAMPLE 24

6-(4-Hydroxy-3,5-dimethyl-phenyl)-4-(3-methyl-1H-indol-2-yl)-2H-pyridazin-3-one

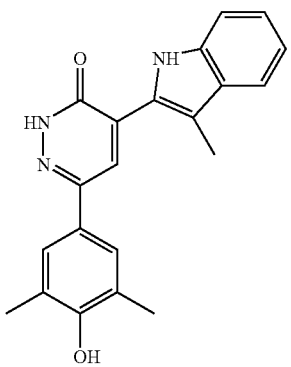

(a) 1-(6-Chloro-3-methoxy-pyridazin-4-yl)-propan-1-ol 104.6 ml of a 1.6M solution of n-Butyl lithium in hexane is added dropwise at −75° C. to 200 ml tetrahydrofuran followed by 28.3 ml 2,2,6,6-tetramethylpiperidine and the resulting solution is allowed to warm to 0° C. and stirred for 30 min. The solution is cooled to −75° C. and a solution of 11 g 3-chloro-6-methoxypyridazine in 100 ml tetrahydrofuran is added at the same temperature. The reaction is stirred for 30 min at −75° C. A solution of 65.9 ml propionaldehyde in 200 ml tetrahydrofuran is cooled to −75° C. and added to the reaction. The solution is stirred at −75° C. for 90 min, then a mixture of 55 ml concentrated aqueous HCl, 220 ml ethanol and 275 ml tetrahydrofuran is added and the mixture is allowed to warm to room temperature. 150 ml of saturated aqueous sodium bicarbonate is slowly added, and the tetrahydrofuran is removed under reduced pressure. The resulting aqueous phase is extracted 3 times with dichloromethane. The organic phase is dried (MgSO$_4$), filtered and evaporated under reduced pressure. The product is purified by silica gel chromatography, eluting with a gradient of ethyl acetate in heptane. Yield 12.25 g. LC-MS (ES+) 203 (M+H)$^+$. NMR analysis indicated that the product contained approximately 15% of 1-(3-Chloro-6-methoxy-pyridazin-4-yl)-propan-1-ol.

(b) 1-(6-Chloro-3-methoxy-pyridazin-4-yl)-propan-1-one 12.25 g 1-(6-Chloro-3-methoxy-pyridazin-4-yl)-propan-1-ol is dissolved in 410 ml tetrahydrofuran and 105 g of manganese dioxide is added. The reaction is stirred for 24 h at RT. Solids are removed by filtration, and the solution is treated with a further 105 g of manganese dioxide for 16 h at RT. Solids are removed by filtration, and the solvent is removed under reduced pressure. The product is purified by silica gel chromatography, eluting with a gradient of ethyl acetate in heptane. Yield 3.25 g. LC-MS (ES+) 201 (M+H)$^+$.

(c) 1-[6-(4-Hydroxy-3,5-dimethyl-phenyl)-3-methoxy-pyridazin-4-yl]-propan-1-one 2 g of 1-(6-Chloro-3-methoxy-pyridazin-4-yl)-propan-1-one and 1.73 g of tetrakis(triphenylphosphine) palladium (0) are dissolved in 10 ml DME and the solution is stirred for 5 min at RT under argon. 3 g of 2,6-Dimethyl-4-(4,4,5,5-tetramethyl-[1,3,2]dioxaborolan-2-yl)-phenol and 10 ml of a 2M aqueous solution of sodium carbonate are added and the reaction solution is stirred at 95° C. for 4 h. The reaction solution is poured into ethyl acetate and washed with saturated aqueous sodium bicarbonate. The organic phase is dried (MgSO$_4$), filtered and evaporated under reduced pressure. The product is purified by silica gel chromatography, eluting with a gradient of ethyl acetate in heptane, followed by purification by preparative RP-HPLC eluting with a gradient of 0-100% acetonitrile in water (+0.01% trifluoroacetic acid). Yield 1.69 g. LC-MS (ES+) 287 (M+H)$^+$.

(d) 4-[6-Methoxy-5-(3-methyl-1H-indol-2-yl)-pyridazin-3-yl]-2,6-dimethyl-phenol 73.4 μl of 2-chloroaniline and 21 mg of anhydrous magnesium sulfate are suspended in 3 ml dimethylacetamide. 100 mg of 1-[6-(4-Hydroxy-3,5-dimethyl-phenyl)-3-methoxy-pyridazin-4-yl]-propan-1-one and 31.4 mg acetic acid are added and the reaction is degassed with argon. 96 mg of tripotassium phosphate and 35.7 mg of bis(tri-tert-butylphosphine) palladium (0) are added and the reaction is degassed with argon. The reaction is heated to 140° C. for 16 h. The solution is filtered. The product is purified by preparative RP-HPLC eluting with a gradient of 0-100% acetonitrile in water (+0.01% trifluoroacetic acid). Yield 35 mg.

(e) 6-(4-Hydroxy-3,5-dimethyl-phenyl)-4-(3-methyl-1H-indol-2-yl)-2H-pyridazin-3-one 6 mg of 4-[6-Methoxy-5-(3-methyl-1H-indol-2-yl)-pyridazin-3-yl]-2,6-dimethyl-phenol is suspended in 2 ml acetonitrile and 6.5 mg of trimethylsilyl chloride and 9.96 mg of potassium iodide are added. The solution is heated to 80° C. for 3 h. The reaction solution is diluted with water and the product is purified by preparative RP-HPLC eluting with a gradient of 0-100% acetonitrile in water (+0.01% trifluoroacetic acid). Yield 3.8 mg. LC-MS (ES+) 346 (M+H)$^+$.

EXAMPLE 25

4-(3-Iodo-1H-indol-2-yl)-6-pyridin-4-yl-2H-pyridazin-3-one

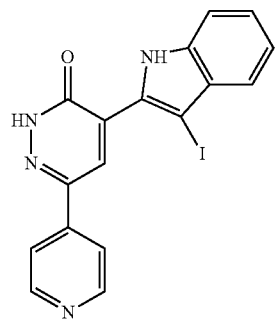

577 mg 4-(1H-Indol-2-yl)-6-pyridin-4-yl-2H-pyridazin-3-one is suspended in 30 mL acetone and 550 mg NIS is added. The reaction mixture is stirred for 3 hours at room temperature, the precipitated product isolated by filtration and washed with acetone. The material product is used without further purification Yield 670 mg. LC-MS (ES+) 415 (M+H)$^+$.

EXAMPLE 26

4-(3-Chloro-1H-indol-2-yl)-6-pyridin-4-yl-2H-pyridazin-3-one

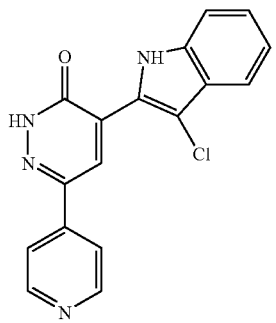

EXAMPLE 26 is synthesized similarly to example 25 by using NCS instead of NIS.
Yield 42 mg. LC-MS (ES+) 324 (M+H)+.

EXAMPLE 27

6-Pyridin-4-yl-4-(3-vinyl-1H-indol-2-yl)-2H-pyridazin-3-one

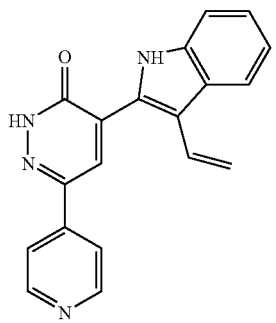

A mixture of 104 mg 4-(3-Iodo-1H-indol-2-yl)-6-pyridin-4-yl-2H-pyridazin-3-one (example 25), 123 mg tributyl(vinyl)tin, 41 mg tetraethylammonium-chloride and 9 mg bis(triphenylphosphine)palladium(II) chloride in DMF is stirred at 80° C. for 40 min. After cooling to room temperature, 4 ml aqueous potassium fluoride solution (30%) are added and the mixture stirred for 30 min at room temperature before extraction with EtOAc. The organic layer is dried over MgSO4 and the solvent evaporated prior to purification of the crude product by preparative RP-HPLC eluting with a gradient of 0-100% acetonitrile in water (+0.01% HCOOH).
Yield 28 mg. LC-MS (ES+) 315 (M+H)+.

EXAMPLE 28

4-(6-Methoxy-1H-indol-2-yl)-6-pyridin-4-yl-2H-pyridazin-3-one

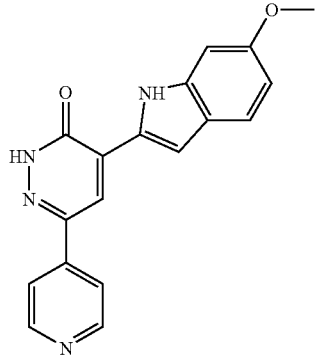

MS: (M+1)=319

EXAMPLE 29

4-(5-Methoxy-1H-indol-2-yl)-6-pyridin-4-yl-2H-pyridazin-3-one

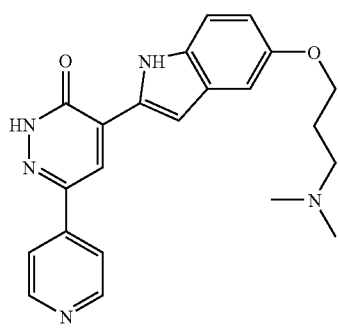

MS: (M+1)=319

EXAMPLE 30

4-[5-(3-Dimethylamino-propoxy)-1H-indol-2-yl]-6-pyridin-4-yl-2H-pyridazin-3-one

MS: (M+1)=390

EXAMPLE 31

4-[6-(2-Piperidin-1-yl-ethoxy)-1H-indol-2-yl]-6-pyridin-4-yl-2H-pyridazin-3-one

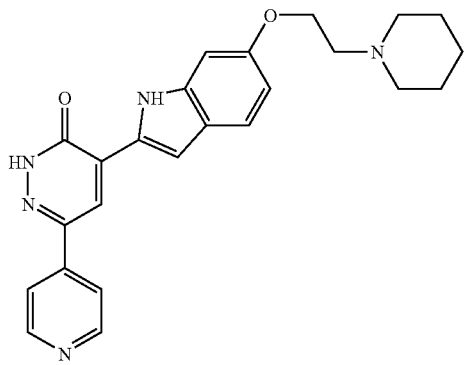

MS: (M+1)=416

EXAMPLE 32

6-Pyridin-4-yl-4-[6-(2-pyrrolidin-1-yl-ethoxy)-1H-indol-2-yl]-2H-pyridazin-3-one

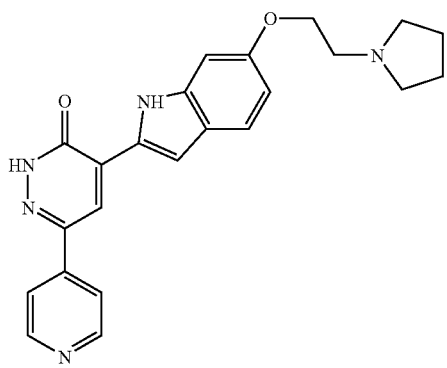

MS: (M+1)=402

EXAMPLE 33

4-(5-Benzyloxy-1H-indol-2-yl)-6-pyridin-4-yl-2H-pyridazin-3-one

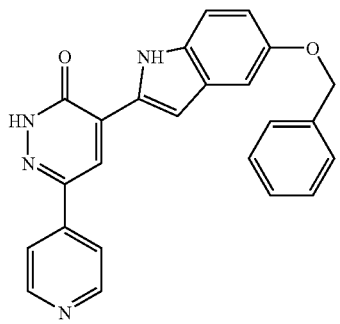

MS: (M+1)=395

EXAMPLE 34

4-(3-Phenethyl-1H-indol-2-yl)-6-pyridin-4-yl-2H-pyridazin-3-one

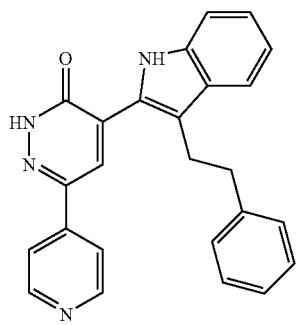

This compound is synthesized analogously to example 10.
MS: (M+1)=393

EXAMPLE 35

6-(2,6-Dimethyl-pyridin-4-yl)-4-(1H-indol-2-yl)-2H-pyridazin-3-one

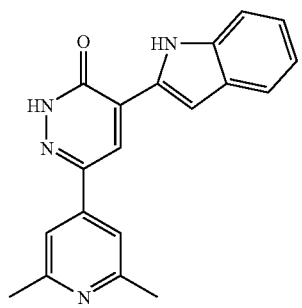

This compound is synthesized analogously to example 2.
MS: (M+1)=317

EXAMPLE 36

4-(5-Chloro-1H-indol-2-yl)-6-(2,6-dimethyl-pyridin-4-yl)-2H-pyridazin-3-one

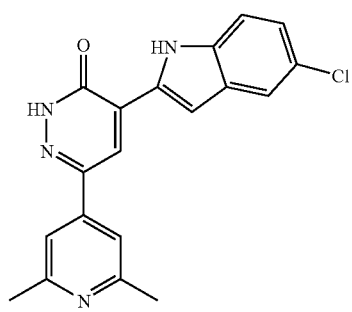

This compound is synthesized analogously to example 2.
MS: (M+1)=351

EXAMPLE 37

4-(6-Piperidin-1-ylmethyl-1H-indol-2-yl)-6-pyridin-4-yl-2H-pyridazin-3-one

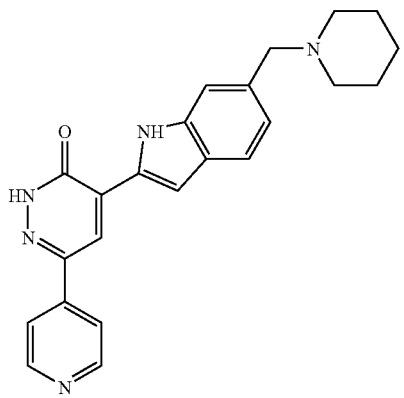

a) 2-[1-(tert-Butoxycarbonyl)-6-(tert-butyldimethylsiloxymethyl)indole-2-yl]-4,4,5,5-tetramethyl, 1,3,2-dioxaborolane 5 g 1-(tert-butoxycarbonyl)-6-(tert-butyldimethylsiloxymethyl)indole (prepared as described in WO03020276) is dissolved in 45 mL anhydrous THF and cooled to 0° C. A solution of LDA in 10 mL THF (prepared at 0° C. from 2.61 mL diisopropylamine and 10.86 mL butyllithium (1.6M in hexanes)) is added dropwise by cannula over 30 minutes. After stirring for 1 hour at 0° C., water and 1N aqueous HCl are added. After stirring for 5 min, the reaction mixture is diluted with EtOAc and the aqueous layer reextracted with EtOAc. Drying (MgSO$_4$) and concentration in vacuo affords 7.76 g crude product as a beige solid, which is directly used in the next step.

b) 6-Hydroxymethyl-2-(3-methoxy-6-pyridin-4-yl-pyridazin-4-yl)-indole-1-carboxylic acid tert-butyl ester 3.94 g 4-Iodo-3-methoxy-6-pyridin-4-yl-pyridazine, 6.74 g 2-[1-(tert-butoxycarbonyl)-6-(tert-butyldimethylsiloxymethyl)indole-2-yl]-4,4,5,5-tetramethyl, 1,3,2-dioxaborolane, 12.29 g cesium carbonate, and 513 mg [1,1'-bis(diphenylphosphino)ferrocene]dichloropalladium(II) complex with dichloromethane (1:1) are dissolved in a mixture of 100 mL dioxane and 30.4 mL water. Argon is bubbled through the solution for 5 minutes. The mixture is heated to reflux for 2 hours. After diluting with EtOAc, the organic phase is washed with water and brine, dried with MgSO$_4$ and concentrated in vacuo.

The crude product is dissolved in 95 mL THF. After addition of 9.91 g tetrabutylammonium fluoride trihydrate, the red solution is stirred for 2 hours. The reaction mixture is diluted with EtOAc, washed with saturated aqueous ammonium chloride, water, and brine, dried with MgSO$_4$ and concentrated in vacuo. Purification on silica affords 3.9 g (72%) 6-hydroxymethyl-2-(3-methoxy-6-pyridin-4-yl-pyridazin-4-yl)-indole-1-carboxylic acid tert-butyl ester.

MS: (M+1)=433.26 c) 6-Formyl-2-(3-methoxy-6-pyridin-4-yl-pyridazin-4-yl)-indole-1-carboxylic acid tert-butyl ester 2 g 6-Hydroxymethyl-2-(3-methoxy-6-pyridin-4-yl-pyridazin-4-yl)-indole-1-carboxylic acid tert-butyl ester is dissolved in 46 mL dichloromethane. After addition of 1.61 g activated manganese (IV) oxide the reaction mixture is heated to reflux for 1 hour. Then every two hours additional manganese (IV) oxide is added until the conversion is complete. The reaction mixture is diluted with dichloromethane and filtered over celite. 1.63 g (82%) crude product is obtained, which is directly used in the next reaction.

d) 6-(Piperidin-1-ylmethyl)-2-(3-methoxy-6-pyridin-4-yl-pyridazin-4-yl)-indole-1-carboxylic acid tert-butyl ester 79 mg 6-formyl-2-(3-methoxy-6-pyridin-4-yl-pyridazin-4-yl)-indole-1-carboxylic acid tert-butyl ester is dissolved in 14 mL dichloroethane. 182 µL piperidine and then 0.7 mL acetic acid are added. 334 mg sodium triacetoxyborohydride is added in several portions over 6 hours. Sat. aq. NaHCO$_3$-solution is added and the reaction mixture is stirred until the CO$_2$-evolution stopped. The reaction mixture is diluted with dichloromethane, the aq. phase washed with dichloromethane, the combined org. phases dried (MgSO$_4$) and concentrated in vacuo. 76 mg (83%) crude product is obtained, which is directly used in the next step.

e) 4-[1H-Indole-6-(piperidin-1-ylmethyl)-2-yl]-6-pyridin-4-yl-2H-pyridazin-3-one 76 mg 6-(piperidin-1-ylmethyl)-2-(3-methoxy-6-pyridin-4-yl-pyridazin-4-yl)-indole-1-carboxylic acid tert-butyl ester is dissolved in 0.6 mL ethanol. 0.5 mL 1 N aqueous sodium hydroxide are added. The reaction mixture is heated to 150° C. in a microwave oven for 15 minutes. Purification by HPLC affords 25 mg (36%) 4-[1H-indole-6-(piperidin-1-ylmethyl)-2-yl]-6-pyridin-4-yl-2H-pyridazin-3-one as its trifluoroacetate salt.

MS: (M+1)=386.27

The compounds 43, 46-48, 50, 53 and 54 are synthesized analogously to example 37.

EXAMPLE 38

4-[3-(4-Acetyl-piperazin-1-ylmethyl)-1H-indol-2-yl]-6-pyridin-4-yl-2H-pyridazin-3-one

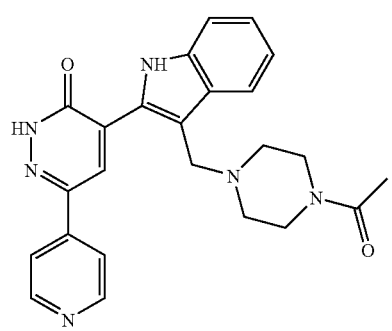

MS: (M+1)=429

EXAMPLE 39

4-(3-Diethylaminomethyl-1H-indol-2-yl)-6-pyridin-4-yl-2H-pyridazin-3-one

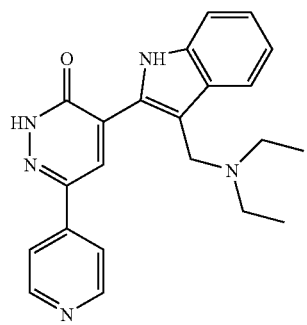

MS: (M+1)=374

EXAMPLE 40

4-(3-Dimethylaminomethyl-1H-indol-2-yl)-6-pyridin-4-yl-2H-pyridazin-3-one

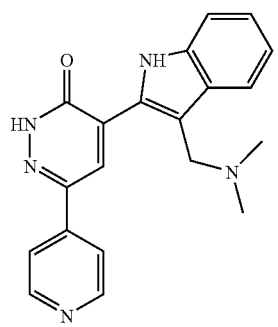

MS: (M+1)=346

EXAMPLE 41

4-(3-Azetidin-1-ylmethyl-1H-indol-2-yl)-6-pyridin-4-yl-2H-pyridazin-3-one

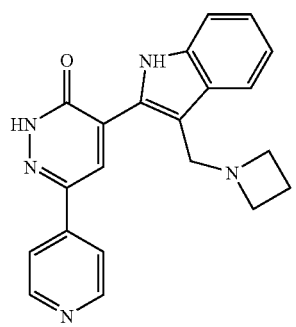

MS: (M+1)=358

EXAMPLE 42

4-(5-Chloro-3-morpholin-4-ylmethyl-1H-indol-2-yl)-6-pyridin-4-yl-2H-pyridazin-3-one

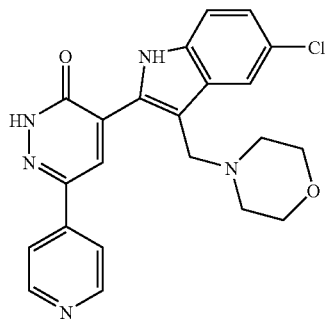

MS: (M+1)=422

EXAMPLE 43

4-(6-Morpholin-4-ylmethyl-1H-indol-2-yl)-pyridin-4-yl-2H-pyridazin-3-one

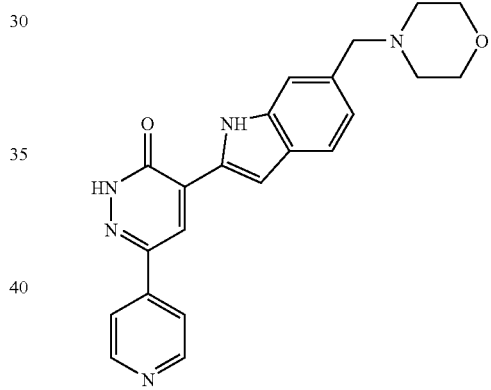

MS: (M+1)=388

EXAMPLE 44

4-[5-(2-Piperidin-1-yl-ethoxy)-1H-indol-2-yl]-6-pyridin-4-yl-2H-pyridazin-3-one

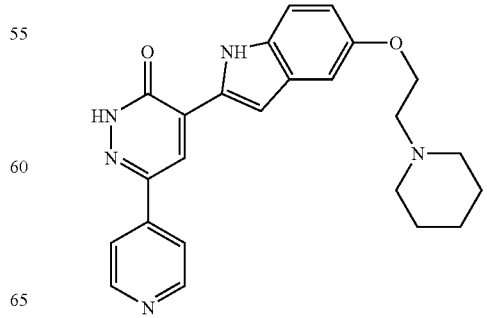

MS: (M+1)=416

EXAMPLE 45

4-[5-(2-Dimethylamino-ethoxy)-1H-indol-2-yl]-6-pyridin-4-yl-2H-pyridazin-3-one

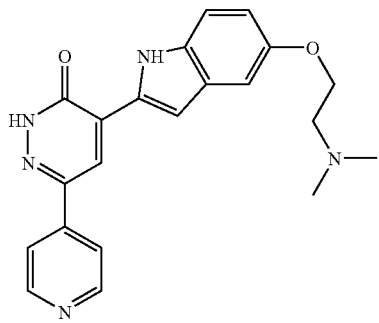

MS: (M+1)=376

EXAMPLE 46

4-[6-(4-Methyl-piperazin-1-ylmethyl)-1H-indol-2-yl]-6-pyridin-4-yl-2H-pyridazin-3-one

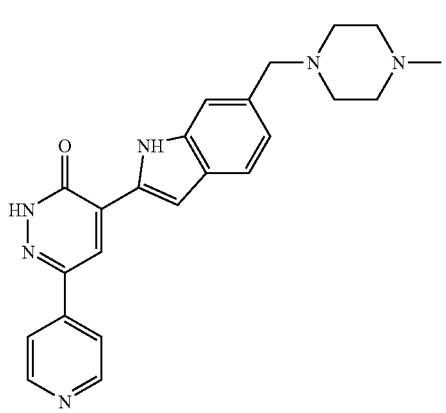

MS: (M+1)=401

EXAMPLE 47

4-(6-Dimethylaminomethyl-1H-indol-2-yl)-6-pyridin-4-yl-2H-pyridazin-3-one

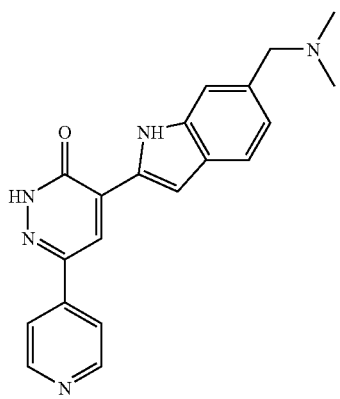

MS: (M+1)=346

EXAMPLE 48

4-(6-Diethylaminomethyl-1H-indol-2-yl)-6-pyridin-4-yl-2H-pyridazin-3-one

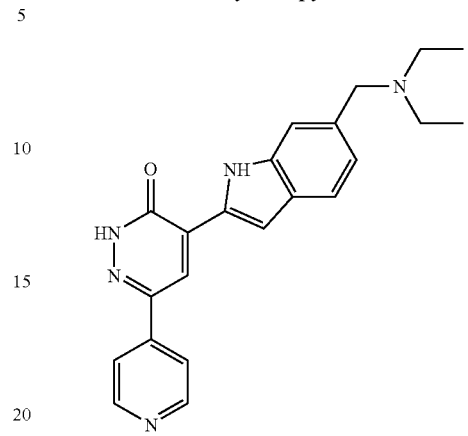

MS: (M+1)=374

EXAMPLE 49

4-[6-(2-Morpholin-4-yl-ethoxy)-1H-indol-2-yl]-6-pyridin-4-yl-2H-pyridazin-3-one

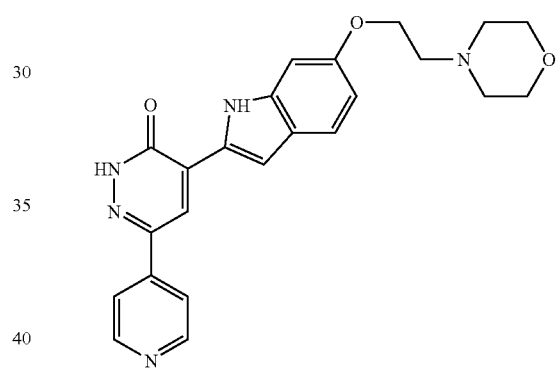

MS: (M+1)=418

EXAMPLE 50

6-Pyridin-4-yl-4-(6-pyrrolidin-1-ylmethyl-1H-indol-2-yl)-2H-pyridazin-3-one

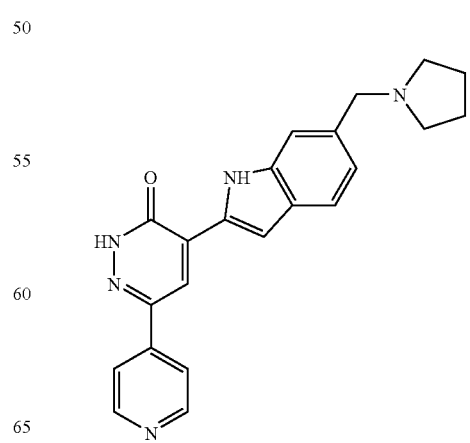

MS: (M+1)=372

EXAMPLE 51

4-[3-Bromo-6-(2-piperidin-1-yl-ethoxy)-1H-indol-2-yl]-6-pyridin-4-yl-2H-pyridazin-3-one

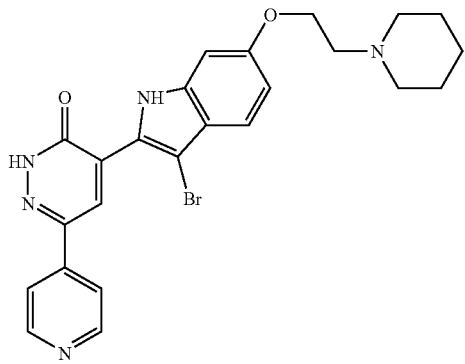

24 mg 4-[1H-indole-6-(2-dimethylaminoethoxy)-2-yl]-6-pyridin-4-yl-2H-pyridazin-3-one was suspended in 1 mL acetone and 10 mg NBS was added. After stirring for 2 hours at rt, the solvent was removed in vacuo. HPLC purification afforded 8 mg (29%) of 4-[1H-indole-3-bromo-6-(2-piperidylethoxy)-2-yl]-6-pyridin-4-yl-2H-pyridazin-3-one as its trifluoroacetate salt.

MS: (M+1)=494.03

EXAMPLE 52

4-{6-[2-(4-Methyl-piperazin-1-yl)-ethoxy]-1H-indol-2-yl}-6-pyridin-4-yl-2H-pyridazin-3-one

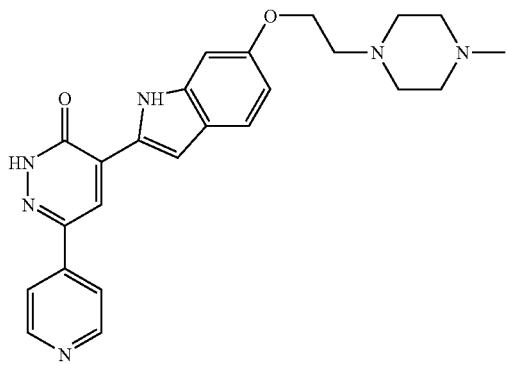

MS: (M+1)=431

EXAMPLE 53

4-[5-(4-Methyl-piperazin-1-ylmethyl)-1H-indol-2-yl]-6-pyridin-4-yl-2H-pyridazin-3-one

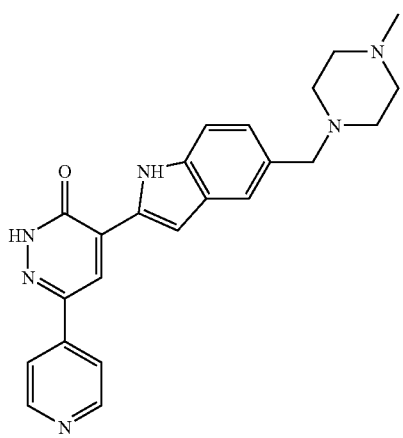

MS: (M+1)=401

EXAMPLE 54

4-(5-Morpholin-4-ylmethyl-1H-indol-2-yl)-6-pyridin-4-yl-2H-pyridazin-3-one

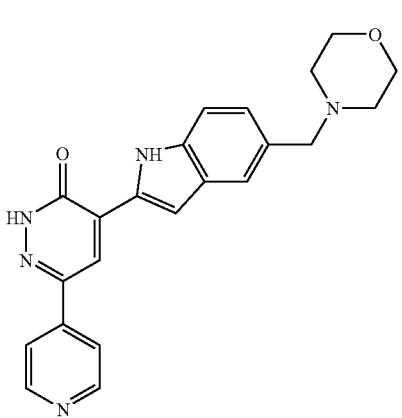

MS: (M+1)=388

EXAMPLE 55

4-{5-[2-(4-Methyl-piperazin-1-yl)-ethoxy]-1H-indol-2-yl}-6-pyridin-4-yl-2H-pyridazin-3-one

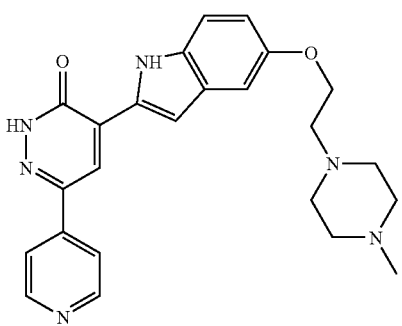

MS: (M+1)=431

EXAMPLE 56

4-(3-Bromo-6-piperidin-1-ylmethyl-1H-indol-2-yl)-6-pyridin-4-yl-2H-pyridazin-3-one

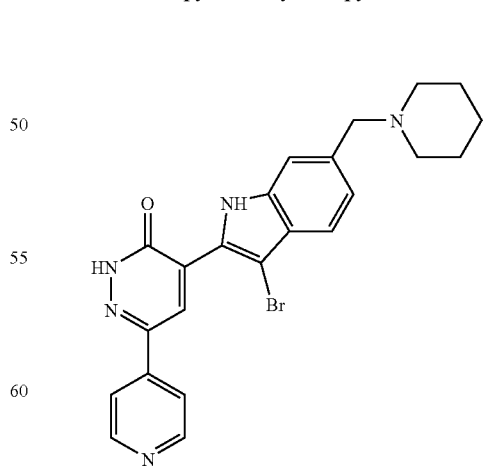

33 mg 4-[1H-indole-6-(2-dimethylaminoethoxy)-2-yl]-6-pyridin-4-yl-2H-pyridazin-3-one is suspended in 1.2 mL acetone and 14 mg NBS is added. After stirring for 2 hours at rt, the solvent is removed in vacuo. HPLC purification affords 12 mg (31%) of 4-[1H-indole-3-bromo-6-(piperidyl methyl)-2-yl]-6-pyridin-4-yl-2H-pyridazin-3-one as its trifluoroacetate salt.

MS: (M+1)=464.

EXAMPLE 57

4-(3-Chloro-6-piperidin-1-ylmethyl-1H-indol-2-yl)-6-pyridin-4-yl-2H-pyridazin-3-one

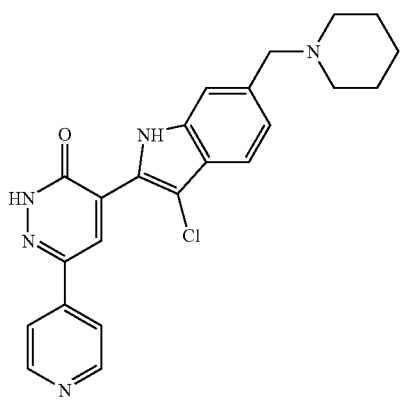

33 mg 4-[1H-indole-6-(2-dimethylaminoethoxy)-2-yl]-6-pyridin-4-yl-2H-pyridazin-3-one is suspended in 1.2 mL acetone and 10.5 mg NCS is added. The reaction mixture is stirred for 24 hours at room temperature and then heated to 50° C. for 2 hours. After addition of 5 mg NCS, the reaction mixture was heated to 50° C. for an additional hour. Then the solvent was removed in vacuo. HPLC purification afforded 8 mg (23%) of 4-[1H-indole-3-chloro-6-(piperidylmethyl)-2-yl]-6-pyridin-4-yl-2H-pyridazin-3-one as its trifluoroacetate salt.

MS: (M+1)=420.17

The following compounds 60 and 61 are synthesized analogously to example 57.

EXAMPLE 58

6-Pyridin-4-yl-4-(1H-pyrrol-2-yl)-2H-pyridazin-3-one

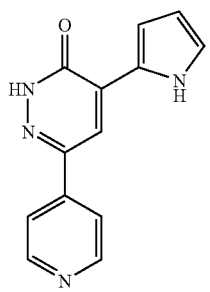

This compound is synthesized analogously to example 1.
MS: (M+1)=239

EXAMPLE 59

4-(5-Methyl-4H-[1,2,4]triazol-3-yl)-6-pyridin-4-yl-2H-pyridazin-3-one

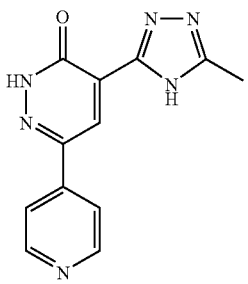

a) 3-Oxo-6-pyridin-4-yl-2,3-dihydro-pyridazine-4-carboxylic acid hydrazide 10 g of 3-oxo-6-pyridin-4-yl-2,3-dihydro-pyridazine-4-carboxylic acid ethyl ester are dissolved in 150 ml of ethanol, 4.2 ml of hydrazine hydrate is added and the mixture is refluxed for 5 hours. After cooling to room temperature, the solid is collected by filtration and dried in vacuo at 40° C.

Yield: 6 g, MS: (M+1)=232 b) 4-(5-Methyl-4H-[1,2,4]triazol-3-yl)-6-pyridin-4-yl-2H-pyridazin-3-one

A mixture of 100 mg of 3-oxo-6-pyridin-4-yl-2,3-dihydro-pyridazine-4-carboxylic acid hydrazide, 130 mg thioacetamide, 87 mg triethylamine, 1 ml of pyridine and 5 ml of butanol is refluxed for 15 hours. After cooling and stirring at room temperature, a solid precipitated is collected by filtration, washed with cold isopropanol and dried in vacuo.

Yield: 26 mg, MS: (M+1)=255

This compound is synthesized analogously to example 1.
MS: (M+1)=239

EXAMPLE 60

4-[5-(4-Chloro-phenyl)-4H-[1,2,4]triazol-3-yl]-6-pyridin-4-yl-2H-pyridazin-3-one

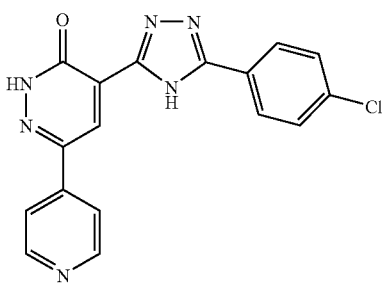

A mixture of 0.5 g 2-(4-fluoro-phenyl)-acetimidic acid methyl ester, 0.24 g of 3-oxo-6-pyridin-4-yl-2,3-dihydro-pyridazine-4-carboxylic acid hydrazide and 3 ml of N-methylpyrrolidone is heated at 130° C. for 2 hours. After cooling to room temperature, 10 ml of water are added and the product extracted with ethyl acetate and purified by chromatography (silicagel, dichloromethane/methanol).

Yield: 35 mg, MS: (M+1)=349

EXAMPLE 61

4-[5-(4-Fluoro-benzyl)-4H-[1,2,4]triazol-3-yl]-6-pyridin-4-yl-2H-pyridazin-3-one

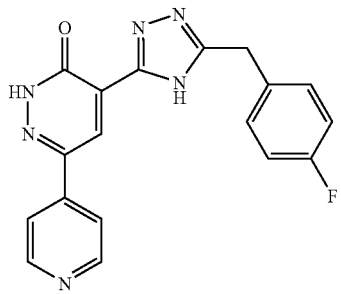

This compound is synthesized analogously to example 60.
MS: (M+1)=349

EXAMPLE 62

4-[6-(2-Morpholin-4-yl-ethyl)-1H-indol-2-yl]-6-pyridin-4-yl-2H-pyridazin-3-one

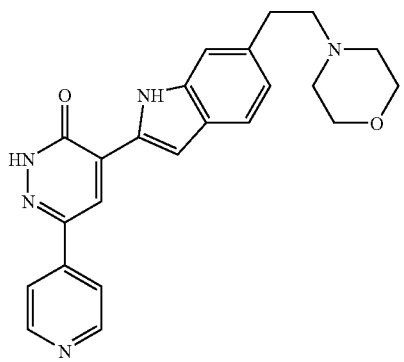

MS: (M+1)=363 a) 6-(2-methoxyvinyl)-2-(3-methoxy-6-pyridin-4-yl-pyridazin-4-yl)-indole-1-carboxylic Acid Tert-Butyl Ester 1.23 g methoxymethyltriphenylphoshonium chloride is suspended in 10 mL THF and cooled to −78° C. 2.20 mL butyllithium (1.6 M in hexanes) is added dropwise and the resulting mixture is stirred for 30 min at −78° C. and then warmed in an ice bath to 0° C. After addition of a solution of 734 mg 6-formyl-2-(3-methoxy-6-pyridin-4-yl-pyridazin-4-yl)-indole-1-carboxylic acid tert-butyl ester (see above) in 5 mL THF, the reaction mixture is heated to reflux for 5 hours. After cooling to rt, the reaction mixture is diluted with heptanes, washed with water, dried (MgSO$_4$) and concentrated in vacuo. The resulting 280 mg crude enol ether is directly used in the next step.

b) 6-(2-Oxoethyl)-2-(3-methoxy-6-pyridin-4-yl-pyridazin-4-yl)-indole-1-carboxylic Acid Tert-Butyl Ester 180 mg 6-(2-methoxyvinyl)-2-(3-methoxy-6-pyridin-4-yl-pyridazin-4-yl)-indole-1-carboxylic acid tert-butyl ester are dissolved in 10 mL acetonitrile. Then 196 mg potassium iodide and 125 µL chlorotrimethylsilane are added. The reaction mixture is stirred for 2 hours at rt. The solvent is removed in vacuo and the obtained solid is dissolved in dichloromethane/water. The aqueous phase is extracted five times with dichloromethane, the combined org. phases are dried (MgSO$_4$) and the solvent removed in vacuo. 200 mg crude product are obtained as a mixture of 6-(2-Oxoethyl)-2-(3-methoxy-6-pyridin-4-yl-pyridazin-4-yl)-indole-1-carboxylic acid tert-butyl ester and 6-(2-oxoethyl)-2-(3-oxo-6-pyridin-4-yl-2,3-dihydro-pyridazin-4-yl)indole-1-carboxylic acid tert-butyl ester. The mixture is directly used in the next step.

c) 6-(2-Piperidylethyl)-2-(3-methoxy-6-pyridin-4-yl-pyridazin-4-yl)-indole-1-carboxylic Acid Tert-Butyl Ester 54 mg of a mixture of 6-(2-oxoethyl)-2-(3-methoxy-6-pyridin-4-yl-pyridazin-4-yl)-indole-1-carboxylic acid tert-butyl ester and 6-(2-oxoethyl)-2-(3-Oxo-6-pyridin-4-yl-2,3-dihydro-pyridazin-4-yl)indole-1-carboxylic acid tert-butyl ester are dissolved in 9 mL dichloroethane. 160 µL morpholine and then 0.46 mL acetic acid are added. 129 mg sodium triacetoxyborohydride are added in several portions over 4 hours. Sat. aq. NaHCO$_3$-solution is added and the reaction mixture is stirred until the CO$_2$-evolution stopped. The reaction mixture is diluted with dichloromethane, the aq. phase washed with dichloromethane, the combined org. phases dried (MgSO$_4$) and concentrated in vacuo. 8 mg (13%) crude product (mixture of 6-(2-piperidylethyl)-2-(3-methoxy-6-pyridin-4-yl-pyridazin-4-yl)-indole-1-carboxylic acid tert-butyl ester and 2-(3-oxo-6-pyridin-4-yl-2,3-dihydro-pyridazin-4-yl)-6-(2-piperidyl-ethyl)-indole-1-carboxylic acid tert-butyl ester is obtained, which is directly used in the next step.

e) 4-[1H-Indole-6-(piperidylethyl)-2-yl]-6-pyridin-4-yl-2H-pyridazin-3-one 8 mg of a mixture of 6-(2-Piperidylethyl)-2-(3-methoxy-6-pyridin-4-yl-pyridazin-4-yl)-indole-1-carboxylic acid tert-butyl ester and 2-(3-oxo-6-pyridin-4-yl-2,3-dihydro-pyridazin-4-yl)-6-(2-piperidyl-ethyl))-indole-1-carboxylic acid tert-butyl ester is dissolved in 0.4 mL ethanol. 0.56 ml 1 N aqueous sodium hydroxide are added. The reaction mixture is heated to 150° C. in a microwave oven for 15 minutes. Purification by HPLC afforded 5 mg (61%) 4-[1H-indole-6-(piperidylethyl)-2-yl]-6-pyridin-4-yl-2H-pyridazin-3-one as its trifluoroacetate salt.

MS: (M+1)=402.20

Functional Measurements for Determination of IC$_{50}$-Values CDK2/Cyclin E Flashplate Assay: 96-Well Format A 96-well streptavidin-coated flashplate is used to assay potency of compounds according formula (I) against CDK2/Cyclin E kinase. To carry out the assay, biotinylated-Rb peptide substrate (Biotin-SACPLNLPLQNNHTAADMYL-SPVRSPKKKGSTTR-OH) is solubilized at 1 mM in kinase buffer (Hepes 50 mM, NaCl 1 mM, MgCl$_2$ 5 mM pH 7.5) as a stock solution conserved at −20° C. in aliquots of 110 µl. The day of the experiment, an aliquot of this solution is thawed and diluted to 14.3 µM in kinase buffer, containing 1 mM dithithreitol (DTT) added in the buffer extemporarily.

70 µl of this solution is added in each well of the flashplate in order to achieve a final concentration of 10 µM (100 µl reactionnal volume). Serial dilutions of inhibitors are prepared in DMSO from 10 mM stock solutions in order to achieve 1000 μM, 333.3 μM, 111.1 μM, 37.03 μM, 12.35 μM, 4.11 μM and 1.37 μM and all rediluted in kinase buffer+DTT in order to achieve 100 μM, 33.3 μM, 11.1 μM, 3.7 μM, 1.24 μM, 0.41 μM and 0.14 μM in DMSO 10% buffer (vol/vol). 10 μl of each of these solutions (or 10 μl of buffer+DTT for controls) are transferred to the testplate wells in order to achieve 10 μM, 3.33 μM, 1.11 μM, 0.37 μM, 0.12 μM, 0.04 μM and 0.01 μM as final concentrations, 1% DMSO (vol/vol). In each well, 10 μl of a solution of a mix of $^{33}P\gamma ATP/ATP$ are added in order to achieve 1 μM final concentration and a total of 1 μCi. The kinase reaction is initiated by addition of 10 μl of a solution at 200 nM of CDK2/Cyclin E in kinase buffer+ DTT (or buffer+DTT for blanks) in order to achieve 20 nM final concentration. After addition of each reagent, the testplate is shaken. The plates are incubated 30 minute at 30° C. with a shaking at 650 rpm. At the end of the incubation, the plates are washed 3 times with 300 μl of PBS (without calcium and magnesium) per well. The incorporation of $^{33}P$ to the peptide is measured by scintillation counting.

| Example | IC$_{50}$[μM] |
|---|---|
| 2 | 0.033 |
| 14 | 0.026 |
| 20 | 0.020 |
| 23 | 0.048 |
| 30 | 0.035 |

What is claimed is:
1. A compound of formula (I)

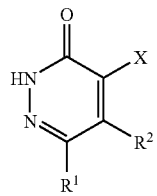

(I)

wherein:
X is a residue selected from the group consisting of:

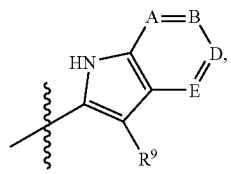

(II)

tetrazolyl and unsubstituted and at least monosubstituted triazolyl, imidazolyl, pyrrolyl and pyrazolyl,
where the substituents of triazolyl, imidazolyl, pyrrolyl and pyrazolyl of X are selected from the group consisting of: halogen, CN, —NO$_2$, R$^{10}$, —OR$^8$, —C(O)R$^8$, —C(O)OR$^8$, —O—C(O)R$^8$, —NR$^7$R$^8$, —NR$^7$C(O)R$^8$, —C(O)NR$^7$R$^8$, —NR$^7$C(S)R$^8$, —C(S)NR$^7$, R$^8$, —SR$^8$, —S(O)R$^8$, —SO$_2$R$^8$, —NR$^7$SO$_2$R$^8$, —SO$_2$NR$^7$R$^8$, —O—SO$_2$R$^8$, —SO$_2$—O—R$^8$, aryl, heteroaryl, heterocyclyl, trifluoromethyl and trifluoromethoxy,
and when said substituents are aryl, heterocyclyl or heteroaryl, each may in turn be at least monosubstituted with C$_1$-C$_6$-alkyl, C$_1$-C$_6$-alkoxy, oxo, halogen, trifluoromethyl, trifluoromethoxy or —OH;
and said X residue bound to the pyridazinone is via the carbon atom being in α-position to the carbon atom of said X residue attached to R$^9$;
A is CR$^3$ or N;
B is CR$^4$ or N;
D is CR$^5$ or N;
E is CR$^6$ or N;
where not more than three of the ring members A, B, D and E may be N;
and at least one of A, B, D and E is N;
R$^1$ is halogen;
unsubstituted or at least monosubstituted C$_1$-C$_{10}$-alkyl, where the substituents of said C$_1$-C$_{10}$-alkyl of R$^1$ are selected from the group consisting of: halogen, —CN, —NO$_2$, —OR$^7$, —C(O)R$^7$, —C(O)OR$^7$, —O—C(O)R$^7$, —NR$^7$R$^8$, —NR$^8$C(O)R$^7$, —C(O)NR$^7$R$^8$, —NR$^8$C(S)R$^7$, —C(S)NR$^7$R$^8$, —SR$^7$, —S(O)R$^7$, —SO$_2$R$^7$, —NR$^8$SO$_2$R$^7$, —SO$_2$NR$^7$R$^8$, —O—SO$_2$R$^7$, —SO$_2$—O—R$^7$, aryl, heteroaryl, heterocyclyl, trifluoromethyl and trifluoromethoxy,
and when said substituents of said C$_1$-C$_{10}$ alkyl are aryl, heterocyclyl and heteroaryl, each may in turn be at least monosubstituted with C$_1$-C$_6$-alkyl, C$_1$-C$_6$-alkoxy, halogen, trifluoromethyl, trifluoromethoxy or OH;
or unsubstituted or at least monosubstituted aromatic or heteroaromatic chosen from the group consisting of phenyl, pyridinyl, pyrimidinyl, pyrazolyl, thienyl, oxazolyl, isoxazolyl, 1H-pyrrolo[2,3-b]pyridinyl, benzo[b]thienyl, benzodioxolyl or thiazolo[3,2-b][1,2,4]-triazolyl,
where the substituents of said aromatic or heteroaromatic of R$^1$ are selected from the group consisting of: halogen, —CN, —NO$_2$, R$^{10}$, —OR$^7$, —C(O)R$^7$, —C(O)OR$^7$, —O—C(O)R$^7$, —NR$^7$R$^8$, —NR$^8$C(O)R$^7$, —C(O)NR$^7$R$^8$, —NR$^8$C(S)R$^7$, —C(S)NR$^7$R$^8$, —SR$^7$, —S(O)R$^7$, —SO$_2$R$^7$, —NR$^8$SO$_2$R$^7$, —SO$_2$NR$^7$R$^8$, —O—SO$_2$R$^7$, —SO$_2$—O—R$^7$, aryl, heteroaryl, trifluoromethyl and trifluoromethoxy,
and when said substituents of said aromatic or heteroaromatic of R$^1$ are themselves aryl or heteroaryl, each of these aryl and heteroaryl substituents on said aryl or heteroaryl of R$^1$ may in turn be at least monosubstituted with C$_1$-C$_6$-alkyl, C$_1$-C$_6$-alkoxy, halogen, trifluoromethyl, trifluoromethoxy or OH;
R$^2$ is hydrogen or C$_1$-C$_{10}$-alkyl;
R$^3$, R$^4$, R$^5$ and R$^6$ are independently from each other selected from the group consisting of:
hydrogen, halogen, —CN, NO$_2$, R$^{10}$, —OR$^8$, —C(O)R$^8$, —C(O)OR$^8$, —O—C(O)R$^8$, —NR$^7$R$^8$, —NR$^7$C(O)R$^8$, —C(O)NR$^7$R$^8$, —NR$^7$C(S)R$^8$, —C(S)NR$^7$R$^8$, —SR$^8$, —S(O)R$^8$, —SO$_2$R$^8$, —NR$^7$SO$_2$R$^8$, —SO$_2$NR$^7$R$^8$, —O—SO$_2$R$^8$, —SO$_2$—O—R$^8$, aryl, heteroaryl, heterocyclyl, difluoromethyl, trifluoromethyl and trifluoromethoxy,
and when said substituents of R$^3$, R$^4$, R$^5$ or R$^6$ are aryl, heterocyclyl or heteroaryl, each may in turn be at least monosubstituted with C$_1$-C$_6$-alkyl, C$_1$-C$_6$-alkoxy, oxo, halogen, trifluoromethyl, trifluoromethoxy or —OH;
R$^7$ and R$^8$ are independently from each other:
H;
or unsubstituted or at least monosubstituted C$_1$-C$_{10}$-alkyl, C$_2$-C$_{10}$-alkenyl, C$_2$-C$_{10}$-alkynyl, heterocyclyl, aryl or heteroaryl, where the substituents of said $C_1$-$C_{10}$-alkyl, $C_2$-$C_{10}$-alkenyl, $C_2$-$C_{10}$-alkynyl, heterocyclyl, aryl or heteroaryl of $R^7$ or $R^8$ are selected from the group consisting of: heteroaryl, heterocyclyl, aryl, oxo, halogen, —OH, $C_1$-$C_{10}$-alkyl, $C_1$-$C_{10}$-alkoxy, ($C_1$-$C_{10}$-alkyl)thio-, C(O)OH, —C(O)O—($C_1$-$C_6$-alkyl), —C(O)NH$_2$, trifluoromethyl, trifluoromethoxy, —CN, —NH$_2$, —NH($C_1$-$C_{10}$-alkyl) and —N($C_1$-$C_{10}$-alkyl)$_2$, and when said substituents of $R^7$ or $R^8$ are aryl, heterocyclyl or heteroaryl, each may in turn be at least monosubstituted with $C_1$-$C_6$-alkyl, $C_1$-$C_6$-alkoxy, oxo, halogen, trifluoromethyl, trifluoromethoxy or —OH;

$R^9$ is selected from the group consisting of:
hydrogen, halogen, —CN, —NO$_2$, $R^{10}$, —OR$^8$, —C(O)R$^8$, —C(O)OR$^8$, —O—C(O)R$^8$, —NR$^7$R$^8$, —NR$^7$C(O)R$^8$, —C(O)NR$^7$R$^8$, —NR$^7$C(S)R$^8$, —C(S)NR$^7$R$^8$, —SR$^8$, —S(O)R$^8$, —SO$_2$R$^8$, —NR$^7$SO$_2$R$^8$, —SO$_2$NR$^7$R$^8$, —O—SO$_2$R$^8$, —SO$_2$—O—R$^8$, aryl, heteroaryl, heterocyclyl, trifluoromethyl and trifluoromethoxy, and when $R^9$ is aryl, heterocyclyl or heteroaryl, each may in turn be at least monosubstituted with $C_1$-$C_6$-alkyl, $C_1$-$C_6$-alkoxy, oxo, halogen, trifluoromethyl, trifluoromethoxy or —OH;

$R^{10}$ is unsubstituted or at least monosubstituted $C_1$-$C_{10}$-alkyl, $C_2$-$C_{10}$-alkenyl or $C_2$-$C_{10}$-alkynyl, where the substituents of said alkyl, alkenyl or alkynyl of $R^{10}$ are selected from the group consisting of: heteroaryl, heterocyclyl, aryl, halogen, —OH, oxo, $C_1$-$C_{10}$-alkoxy, ($C_1$-$C_{10}$-alkyl)thio-, —C(O)OH, —C(O)O—($C_1$-$C_6$-alkyl), —C(O)NH$_2$, trifluoromethyl, trifluoromethoxy; —CN, —NH$_2$, —NH($C_1$-$C_{10}$-alkyl) and —N($C_1$-$C_{10}$-alkyl)$_2$, and when said substituents of said alkyl, alkenyl, or alkynyl of $R^{10}$ are aryl, heterocyclyl or heteroaryl, each may in turn be at least monosubstituted with $C_1$-$C_6$-alkyl, $C_1$-$C_6$-alkoxy, —C(O)—($C_1$-$C_6$-alkyl), oxo, halogen, trifluoromethyl, trifluoromethoxy or —OH;

Heteroaryl is a 5 to 10-membered, aromatic, mono- or bicyclic heterocycle containing one or more heteroatoms selected from the group consisting of N, O and S;

Aryl is a 6 to 10-membered, mono- or bicyclic aromatic ring; and

Heterocyclyl is a 4- to 10-membered, non-aromatic, mono- or bicyclic heterocycle containing one or more heteroatoms selected from the group consisting of N, O and S;

or a physiologically acceptable salt thereof.

2. The compound according to claim 1, wherein in formula (I),

X is a residue selected from the group consisting of:

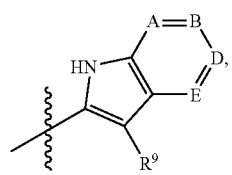

(II)

and unsubstituted and at least monosubstituted pyrrolyl,
where the substituents of pyrrolyl are selected from the group consisting of: halogen, —CN, $R^{10}$, —OR$^8$, C(O)R$^8$, —C(O)OR$^8$, —NR$^8$H, —NR$^8$($C_1$-$C_6$-alkyl), —C(O)NR$^8$H, —SR$^8$, —SO$_2$NR$^8$H, —SO$_2$R$^8$, aryl, heteroaryl, heterocyclyl, difluoromethyl, trifluoromethyl and trifluoromethoxy, and when said substituents of pyrolyl are aryl, heterocyclyl or heteroaryl, each may in turn be at least monosubstituted with $C_1$-$C_6$-alkyl, $C_1$-$C_6$-alkoxy, oxo, halogen, trifluoromethyl, trifluoromethoxy or —OH;

and each of said X residues bound to the pyridazinone is via the carbon atom in α-position to the carbon atom of said X residue attached to $R^9$;

A is CR$^3$ or N;
B is CR$^4$ or N;
D is CR$^5$ or N;
E is CR$^6$ or N;
where not more than two of the substituents A, B, D and E may be N;

$R^1$ is: unsubstituted or at least monosubstituted $C_1$-$C_6$-alkyl,
where the substituents of said alkyl of $R^1$ are selected from the group consisting of: fluoro, chloro, —OH, $C_1$-$C_6$-alkoxy, —NH$_2$, —NH($C_1$-$C_6$-alkyl), —N($C_1$-$C_6$-alkyl)$_2$, heterocyclyl-($C_1$-$C_6$-alkyl)-NH—, aryl-($C_1$-$C_6$-alkyl)-NH—, heterocyclyl, aryl and heteroaryl, and the aryl-, heterocyclyl- and heteroaryl-fragments of said substituents of $R^1$ may in turn be at least monosubstituted with $C_1$-$C_4$-alkyl, $C_1$-$C_4$-alkoxy, fluoro, chloro, trifluoromethyl, trifluoromethoxy or —OH;

or unsubstituted or at least monosubstituted aryl or heteroaryl,
where the substituents of said aryl or heteroaryl of $R^1$ are selected from the group consisting of: halogen, $R^{10}$, —OR$^7$, —C(O)R$^7$, —C(O)OR$^7$, —NR$^7$H, —NR$^7$($C_1$-$C_6$-alkyl), —C(O)NR$^7$H, —SR$^7$, aryl, heteroaryl, trifluoromethyl and trifluoromethoxy, and each of said aryl and heteroaryl substituents substituted on $R^1$ may in turn be at least monosubstituted with $C_1$-$C_6$-alkyl, $C_1$-$C_6$-alkoxy, halogen, trifluoromethyl, trifluoromethoxy or —OH;

$R^2$ is hydrogen or $C_1$-$C_6$-alkyl;

$R^3$, $R^4$, $R^5$ and $R^6$ are independently from each other selected from the group consisting of:
hydrogen, halogen, —CN, $R^{10}$, —OR$^8$, —C(O)R$^8$, —C(O)OR$^8$, —NR$^8$H, —NR$^8$($C_1$-$C_6$-alkyl), —C(O)NR$^8$H, —SR$^8$, —SO$_2$NR$^8$H, —SO$_2$R$^8$, aryl, heteroaryl, heterocyclyl, difluoromethyl, trifluoromethyl and trifluoromethoxy, and each of said aryl, heterocyclyl and heteroaryl of $R^3$, $R^4$, $R^5$ or $R^6$ may in turn be at least monosubstituted with $C_1$-$C_6$-alkyl, $C_1$-$C_6$-alkoxy, oxo, halogen, trifluoromethyl, trifluoromethoxy or —OH;

$R^7$ and $R^8$ are independently from each other:
H;
or unsubstituted or at least monosubstituted $C_1$-$C_6$-alkyl, heterocyclyl, phenyl or heteroaryl,
where the substituents of said alkyl, heterocyclyl, phenyl or heteroaryl of $R^7$ or $R^8$ are selected from the group consisting of: heteroaryl, heterocyclyl, phenyl, fluoro, chloro, —OH, $C_1$-$C_6$-alkyl, $C_1$-$C_6$-alkoxy, trifluoromethyl, trifluoromethoxy, —NH$_2$, —NH($C_1$-$C_6$-alkyl) and —N($C_1$-$C_6$-alkyl)$_2$, and each of said heterocyclyl, phenyl and heteroaryl substituents of said alkyl, heterocyclyl, phenyl, heteroaryl, of $R^7$ or $R^8$ may in turn be at least monosubstituted with $C_1$-$C_3$-alkyl, $C_1$-$C_3$-alkoxy, oxo, trifluoromethyl, trifluoromethoxy, fluoro, chloro or —OH;

$R^9$ is selected from the group consisting of:
hydrogen, halogen, —CN, $R^{10}$, —$OR^8$, —C(O)O—($C_1$-$C_6$-alkyl), —C(O)—($C_1$-$C_6$-alkyl), —$SR^8$, —C(O)$NR^8$H, aryl, heteroaryl, heterocyclyl, trifluoromethyl and trifluoromethoxy, and each of said aryl, heterocyclyl and heteroaryl may in turn be at least monosubstituted with $C_1$-$C_6$-alkyl, $C_1$-$C_6$-alkoxy, oxo, halogen, trifluoromethyl, trifluoromethoxy or —OH;

$R^{10}$ is unsubstituted or at least monosubstituted $C_1$-$C_6$-alkyl or $C_2$-$C_6$-alkenyl, where the substituents of said alkyl or alkenyl of $R^{10}$ are selected from the group consisting of: phenyl, heteroaryl, heterocyclyl, —OH, —$NH_2$, —NH($C_1$-$C_6$-alkyl) and —N($C_1$-$C_6$-alkyl)$_2$, and each of said phenyl, heterocyclyl and heteroaryl of said alkyl or alkeny of $R^{10}$ may in turn be at least monosubstituted with $C_1$-$C_3$-alkyl, $C_1$-$C_3$-alkoxy, —CO—($C_1$-$C_3$-alkyl), trifluoromethyl, trifluoromethoxy, fluoro, chloro or —OH;

Heteroaryl is imidazolyl, thienyl, furanyl, oxazolyl, isoxazolyl, pyridinyl, pyrimidinyl, pyrazolyl, benzo[b]thienyl, thiazolo[3,2-b][1,2,4]-triazolyl, pyrrolyl, quinolinyl, isoquinolinyl, 1,2,3,4-tetrahydroquinolinyl, benzoimidazolyl, indolyl or 1,3-benzo-dioxolyl;

Aryl is naphthyl, indanyl or phenyl;

Heterocyclyl is azetidinyl, azepanyl, 4-oxo-azepanyl, 1,4-diazepanyl, tetrahydrofuranyl, 1,3-dioxolanyl, morpholinyl, pyrrolidinyl, piperazinyl or piperidinyl;

or a physiologically acceptable salt thereof.

3. The compound according to claim 1, wherein:

$R^1$ is an unsubstituted or at least monosubstituted phenyl, pyridinyl, pyrimidinyl, pyrazolyl, thienyl, oxazolyl, isoxazolyl, 1H-pyrrolo[2,3-b]pyridinyl, benzo[b]thienyl, benzodioxolyl or thiazolo[3,2-b][1,2,4]-triazolyl, where the substituents of $R^1$ are selected from the group consisting of: halogen, $C_1$-$C_6$-alkyl, phenyl-($C_1$-$C_6$-alkyl)-, —OH, $C_1$-$C_6$-alkoxy, ($C_1$-$C_6$-alkyl)thio-, —O-phenyl, —$NH_2$, —N($C_1$-$C_6$-alkyl)$_2$, —NH($C_1$-$C_6$-alkyl), $H_2$N—($C_1$-$C_6$-alkyl)-NH—, ($C_1$-$C_6$-alkyl)HN—($C_1$-$C_6$-alkyl)-NH—, ($C_1$-$C_6$-alkyl)$_2$N—($C_1$-$C_6$-alkyl)-NH—, heterocyclyl-($C_1$-$C_6$-alkyl)-NH—, heteroaryl-($C_1$-$C_6$-alkyl)-NH—, phenyl-($C_1$-$C_6$-alkyl)-NH—, trifluoromethyl, trifluoromethoxy, phenyl and heteroaryl, and the phenyl-, heterocyclyl- and heteroaryl of said substituents on $R^1$ may in turn be at least monosubstituted with $C_1$-$C_3$-alkyl, $C_1$-$C_3$-alkoxy, fluoro, chloro, trifluoromethyl, trifluoromethoxy or —OH;

or a physiologically acceptable salt thereof.

4. The compound according to claim 1, wherein:

$R^1$ is an unsubstituted or at least monosubstituted phenyl, thienyl, pyrazolyl, pyridinyl or pyrimidinyl, where said substituents of the phenyl, thienyl, pyrazolyl, pyridinyl or pyrimidinyl of $R^1$ are selected from the group consisting of: $C_1$-$C_4$-alkyl, —OH, $C_1$-$C_4$-alkoxy, ($C_1$-$C_4$-alkyl)thio-, trifluoromethyl, trifluoromethoxy and —NH($C_1$-$C_4$-alkyl), and —NH($C_1$-$C_4$-alkyl) and each of these substituents may in turn be at least monosubstituted with phenyl, piperazinyl, piperidinyl or morpholinyl;

or a physiologically acceptable salt thereof.

5. The compound according to claim 1, wherein:

$R^2$ is hydrogen; or a physiologically acceptable salt thereof.

6. A compound selected from the group consisting of:
6-pyridin-4-yl-4-(1H-pyrrol-2-yl)-2H-pyridazin-3-one;
4-(5-methyl-4H-[1,2,4]triazol-3-yl)-6-pyridin-4-yl-2H-pyridazin-3-one;
4-[5-(4-chloro-phenyl)-4H-[1,2,4]triazol-3-yl]-6-pyridin-4-yl-2H-pyridazin-3-one; and
4-[5-(4-fluoro-benzyl)-4H-[1,2,4]triazol-3-yl]-6-pyridin-4-yl-2H-pyridazin-3-one;

or a physiologically acceptable salt thereof.

7. A pharmaceutical composition comprising an effective dose of at least one compound according to claim 1, or a physiologically acceptable salt thereof, and a physiologically acceptable carrier.

8. The pharmaceutical composition according to claim 7, which pharmaceutical composition is in the form of a pill, tablet, lozenge, coated tablet, granule, capsule, hard or soft gelatin capsule, aqueous solution, alcoholic solution, oily solution, syrup, emulsion suspension, pastille, suppository, solution for injection or infusion, ointment, tincture, cream, lotion, powder, spray, transdermal therapeutic systems, nasal spray, aerosol mixture, microcapsule, implant, rod or plaster.

9. A pharmaceutical composition comprising an effective dose of at least one compound according to claim 6, or a physiologically acceptable salt thereof, and a physiologically acceptable carrier.

10. The pharmaceutical composition according to claim 9, which pharmaceutical composition is in the form of a pill, tablet, lozenge, coated tablet, granule, capsule, hard or soft gelatin capsule, aqueous solution, alcoholic solution, oily solution, syrup, emulsion suspension, pastille, suppository, solution for injection or infusion, ointment, tincture, cream, lotion, powder, spray, transdermal therapeutic systems, nasal spray, aerosol mixture, microcapsule, implant, rod or plaster.

* * * * *